US009809845B2

(12) United States Patent
Narayanan et al.

(10) Patent No.: US 9,809,845 B2
(45) Date of Patent: Nov. 7, 2017

(54) METHODS AND REAGENTS FOR AMPLIFYING NUCLEIC ACIDS

(75) Inventors: Jothikumar Narayanan, Atlanta, GA (US); Prithiviraj Jothikumar, Atlanta, GA (US); Vincent Hill, Decatur, GA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 161 days.

(21) Appl. No.: 14/419,641

(22) PCT Filed: Aug. 6, 2012

(86) PCT No.: PCT/US2012/049784
§ 371 (c)(1),
(2), (4) Date: Feb. 4, 2015

(87) PCT Pub. No.: WO2014/025337
PCT Pub. Date: Feb. 13, 2014

(65) Prior Publication Data
US 2015/0159205 A1    Jun. 11, 2015

(51) Int. Cl.
*C12P 19/34* (2006.01)
*C12Q 1/68* (2006.01)
*C12Q 1/70* (2006.01)

(52) U.S. Cl.
CPC ......... *C12Q 1/6844* (2013.01); *C12Q 1/6806* (2013.01); *C12Q 1/689* (2013.01); *C12Q 1/6888* (2013.01); *C12Q 1/701* (2013.01); *C12Q 2600/158* (2013.01)

(58) Field of Classification Search
CPC ............ C12C 1/6844; C12C 2521/101; C12C 2525/301; C12C 2527/101; C12C 2531/119; C12C 1/6806; C12C 1/6888; C12C 1/689; C12C 1/701; C12C 2600/158
USPC ..................................................... 435/91.2
See application file for complete search history.

(56) References Cited

U.S. PATENT DOCUMENTS 7,638,280 B2    12/2009  Kanda et al.
8,017,357 B2     9/2011  Notomi et al.

2008/0044921 A1    2/2008  Iwaki et al.
2009/0142752 A1*   6/2009  Hall ..................... C12Q 1/6813
                                                    435/5
2011/0165568 A1*   7/2011  Vatta ................... C07K 14/245
                                                    435/6.11

FOREIGN PATENT DOCUMENTS

WO    WO 2011030145    *  3/2011

OTHER PUBLICATIONS

Kimura et al., Nucleic Acids Research, 2011, vol. 39, No. 9, e59, pp. 1-8.*
Prithiviraj et al. "Rapid detection of microbial DNA by a novel isothermal genome exponential amplification reaction (GEAR) assay." *Biochemical and Biophysical Research Communications* 420:738-742, 2012.
Fang et al. "Cross-priming amplification for rapid detection of *Mycobacterium tuberculosis* in sputum specimens." *J. Clin. Microbiol.* 47: 845-847, 2009.
Jothikumar et al. "Visual endpoint detection of *Escherichia coli* O157: H7 using isothermal Genome Exponential Amplification Reaction (GEAR) assay and malachite green." *Journal of Microbiological Methods* 98:122-127, 2014.
Mitani et al. "Rapid SNP diagnostics using asymmetric isothermal amplification and a new mismatch-suppression technology." *Nature Methods* 4:257-262, 2007.
Mori et al. "Detection of loop-mediated isothermal amplification reaction by turbidity derived from magnesium pyrophosphate formation." *Biochemical and Biophysical Research Communications* 289:150-154, 2001.
Nagamine et al. "Accelerated reaction by loop-mediated isothermal amplification using loop primers." *Molecular and Cellular Probes* 16 (2002): 223-229.
Notomi et al. "Loop-mediated isothermal amplification of DNA." *Nucleic Acids Research* 28: e63, 2000.
Van Ness et al. "Isothermal reactions for the amplification of oligonucleotides." *Proc. Natl. Acad. Sci.* 100: 4504-4509, 2003.

* cited by examiner

*Primary Examiner* — Cynthia B Wilder
(74) *Attorney, Agent, or Firm* — Klarquist Sparkman, LLP

(57) ABSTRACT

This disclosure related to methods and reagents for isothermal amplification of nucleic acid molecules. In some embodiments, methods are provided for amplification of a nucleic acid molecule from a biological sample. Additional embodiments include identification of a target nucleic acid molecule in a biological sample using the disclosed amplification methods.

29 Claims, 17 Drawing Sheets

FIG. 2A

CTCCATGAAGTCGGAATCGCTA GTAATCGTGGATCAGAATGCCAC GGTGAATACGTTCCCGGGC
FT> IR <T>

CTGTACACACCGCCCGTCACACCA TGGGAGTGGGTTGCAAAAGA
IF <BT

FIG. 2B

FT: 5'-gcccgggaacgtattcaccCTCCATGAAGTCGGAATCGCTA-3'
         Tc                  F BT: 5'-ggtgaatacgttcccgggcTCTTTTGCAACCCACTCCCA-3'
         T                   Bc

IR: 5'-GTGGCATTCTGATCCACGATTA-3'
IF: 5'-TACACACCGCCCGTCACA-3'

FIG. 3    I. Starting material producing step
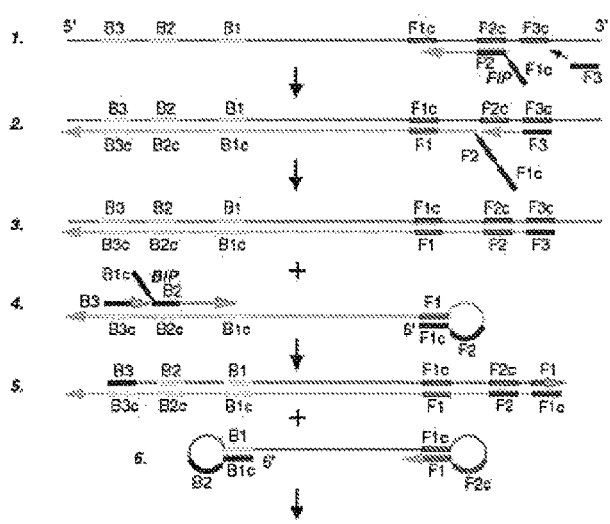
Prior Art
II. Cycling amplification step
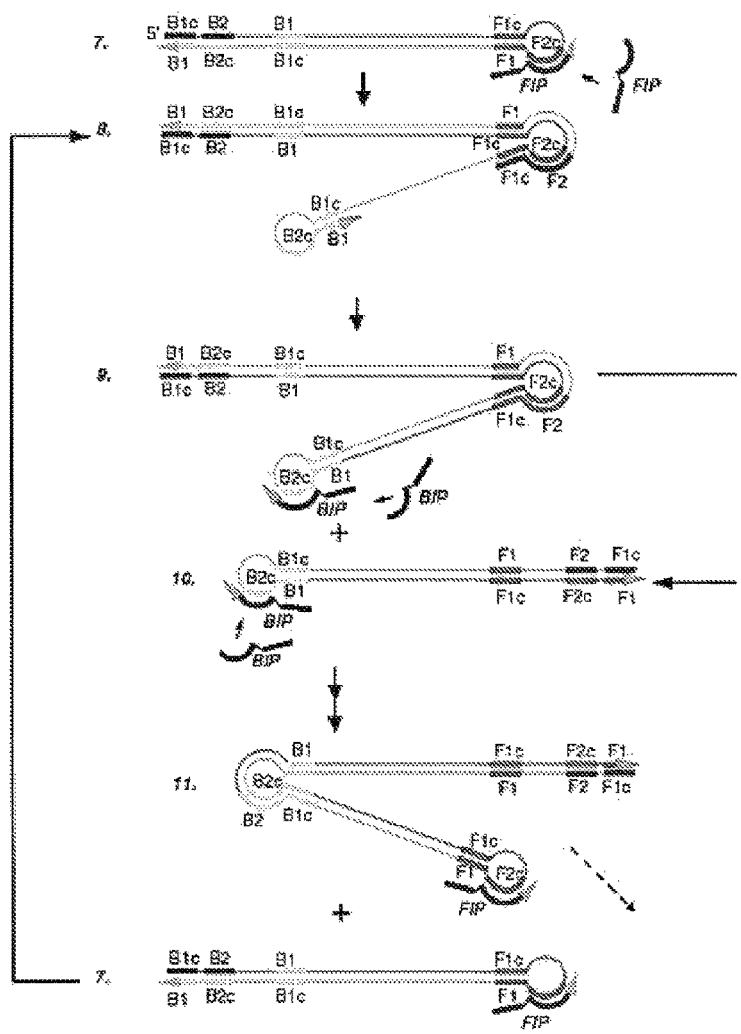

FIG. 3 cont.    III. Elongation and recycling step
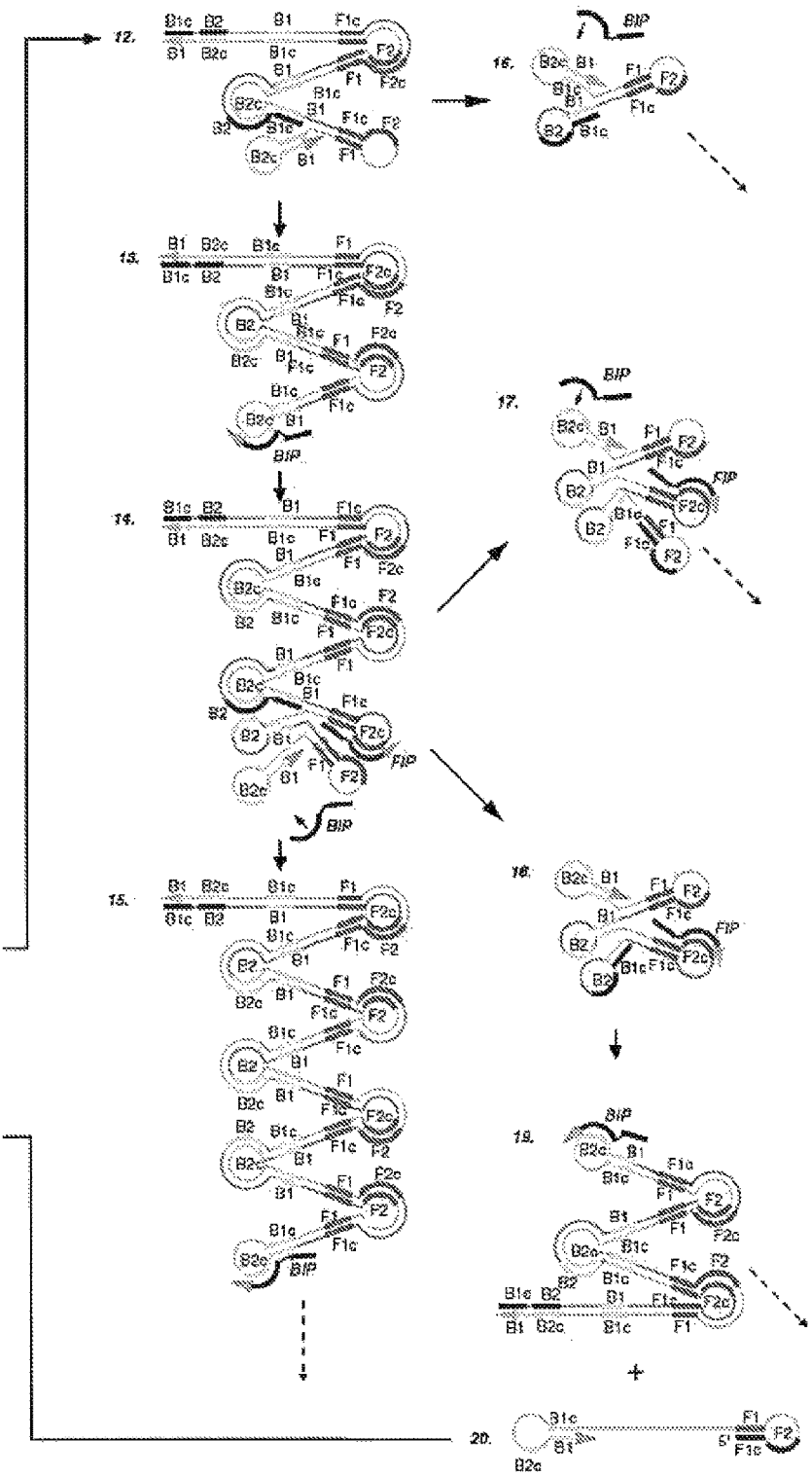
Prior Art

METHODS AND REAGENTS FOR AMPLIFYING NUCLEIC ACIDS

CROSS REFERENCE TO RELATED APPLICATION

This is the U.S. National Stage of International Application No. PCT/US2012/049784, filed Aug. 6, 2012, which was published in English under PCT Article 21(2).

FIELD

This application relates to the field of nucleic acid amplification, particularly to methods and reagents for isothermal amplification of nucleic acids.

BACKGROUND

Amplification of nucleic acids is widely used in research, forensics, medicine and agriculture. Polymerase chain reaction (PCR) is the most widely used method for in vitro DNA amplification. A PCR reaction typically utilizes two oligonucleotide primers that are hybridized to the 5' and 3' borders of the target nucleic acid molecule and a DNA polymerase that extends the annealed primers by polymerizing deoxyribonucleotide-triphosphates (dNTPs) to generate double-stranded products. By cycling the temperature of the reaction mixture (known as thermocycling), the two strands of the DNA product are separated and can serve as templates for the next round of annealing and extension, and the process is repeated, resulting in exponential amplification of the template DNA.

Other nucleic acid amplification methods have also been developed that do not rely on thermocycling. These methods are broadly categorized as isothermal amplification methods due to the fact that they do not rely on repeated cycles of temperature change to operate. However, current isothermal amplification methods require multiple enzymes, lack the specificity of PCR reactions or require four or more primers targeting six or more regions of the template nucleic acid for efficient amplification. A new isothermal amplification technique would be useful that combines simple design (e.g., at most four primers targeting at most five template regions), cost-efficiency (e.g., using a single enzyme), and robustness (e.g., amplification at temperatures ≥60° C.) for the development of, for example, field and point of care testing.

SUMMARY

This disclosure provides a simple, rapid, and useful method for amplifying and identifying target nucleic acid molecules in a sample, termed Genome Exponential Amplification Reaction (GEAR). The provided method includes the use of a single enzyme (a strand displacement polymerase), use of two or four primers targeting three or five regions of the template, respectively, and can be performed at amplification temperatures of ≥60° C. to allow for a robust and specific amplification reaction.

Several embodiments include a method of amplifying a target nucleic acid molecule comprising from 5' to 3', a 5'-end region, a center region, and a 3'-end region, wherein each region is non-overlapping and comprises at least 10 consecutive nucleotides, wherein the target nucleic acid molecule is at most 250 nucleotides in length. Amplifying the target nucleic acid molecule comprises contacting the target nucleic acid molecule with an effective amount of a forward turn-back primer comprising a first segment comprising at least 10 consecutive nucleotides capable of hybridizing to the center region and a second segment comprising at least 10 consecutive nucleotides capable of hybridizing to the complement of the 5'-end region, wherein the first segment is 5' to the second segment. Amplifying the target nucleic acid molecule also includes contacting the target nucleic acid molecule with a reverse turn-back primer comprising a first segment comprising at least 10 consecutive nucleotides capable of hybridizing to the complement of the center region and a second segment comprising at least 10 consecutive nucleotides capable of hybridizing to the 3'-end region, wherein the first segment is 5' to the second segment. Amplifying the target nucleic acid molecule is performed under conditions sufficient for isothermal amplification, thereby amplifying the target nucleic acid molecule.

In some embodiments, the first segment of the forward turn-back primer comprises at least 10 consecutive nucleotides of the complement of the center region, the second segment of the forward turn-back primer comprises at least 10 consecutive nucleotides of the 5'-end region, the first segment of the reverse turn-back primer comprises at least 10 consecutive nucleotides of the center region, the second segment of the reverse turn-back primer comprises at least 10 consecutive nucleotides complementary to the 3'-end region, the internal forward primer comprises at least 10 consecutive nucleotides of the internal forward region, the internal reverse primer comprises at least 10 consecutive nucleotides complementary to the internal reverse region; or two or more thereof.

In several embodiments, the forward turn-back primer, the reverse turn-back primer or both, are from 20-50 nucleotides in length. In additional embodiments, the internal forward primer, the internal reverse primer or both, are from 10-50 nucleotides in length. In further embodiments, the first segment of the forward turn-back primer comprises at least 10 consecutive nucleotides complementary to the first segment of the reverse turn-back primer. In other embodiments, the first segment of the forward turn-back primer consists of the nucleotide sequence complementary to the center region and the first segment of the reverse turn-back primer consists of the nucleotide sequence of the center region.

Several embodiments include detecting the amplified target nucleic acid molecule. In some embodiments, detecting the target nucleic acid molecule comprises real-time isothermal amplification. In additional embodiments, detecting the amplified target nucleic acid molecule comprises contacting the amplified target nucleic acid molecule with a DNA intercalating dye.

In some embodiments, amplifying the target nucleic acid molecule under conditions sufficient for isothermal amplification includes amplification at about 50 to 75° C. In other embodiments, amplifying the target nucleic acid molecule does not include the use of an outer strand displacement primer.

In some embodiments, amplifying the target nucleic acid molecule includes use of a strand-displacement polymerase.

Several embodiments include a method of identifying a target nucleic acid molecule in a biological sample, which includes amplifying the target nucleic from the biological sample according to the method described above and detecting the amplified target nucleic acid molecule, thereby identifying the target nucleic acid molecule in a biological sample.

The disclosure also provides methods of using malachite green (MG) to detect amplicons following an amplification reaction, such as isothermal amplification (e.g., GEAR or LAMP). The presence of MG in the amplification produces a visible color in following amplification if the target is present, while an absence of the visible color following amplification indicates the target nucleic acid molecule was not present.

The foregoing and other objects and features of the disclosure will become more apparent from the following detailed description, which proceeds with reference to the accompanying figures.

BRIEF DESCRIPTION OF THE DRAWINGS

FIGS. 2A-2C show a series of nucleic acid sequences and a schematic diagram concerning an embodiment of the isothermal amplification assay provided (GEAR). FIG. 2A shows a portion of the 16S *Escherichia coli* nucleotide sequence (SEQ ID NO: 1; nucleotides 1308-1415 of GEN-BANK™ Accession No. GU594309, incorporated by reference herein as present in the database on Jul. 6, 2012); the locations of primers used for the amplification of this sequence using the GEAR assay are underlined. FIG. 2B shows the sequence of turn-back primers FT (SEQ ID NO: 2) and BT (SEQ ID NO: 3), as well as the internal reverse primer (IR; SEQ ID NO: 4) and internal forward primer (IF; SEQ ID NO: 5) for the GEAR assay for the detection of *Escherichia coli*. Turn-back sequence regions of the forward and reverse primers self-hybridize in the absence of amplification. FIG. 2C shows a schematic diagram illustrating isothermal amplification using the GEAR assay based on the pair of turn-back primers. The primer FT (left panel) anneals to the anti-sense strand and the primer BT (right panel) anneals to the sense strand of the target DNA. The amplification step ultimately produces C-clamp like DNA structure in series of cycling stages of F1 through F6 and B1 through B6 respectively for primers FT and BT.

FIG. 3 is a schematic diagram illustrating the prior art method of Loop mediated isothermal amplification of DNA (LAMP) (FIG. 3 is FIG. 1A of Notami et al., *Nucleic Acids Res.*, 28:e63, 2000).

FIG. 13A illustrates results of GEAR assay containing MG added to all 6 tubes prior to reaction. Three replicates of positive controls (R1, R2 and R3) containing *E. coli* DNA and three negative controls (R1, R2 and R3) with no template DNA are shown. FIG. 13B illustrates results of GEAR assay containing MG added to all 6 tubes. Color changes observed after reaction performed at 60° C. No color change indicates a positive reaction in positive controls (R1, R2 and R3) while blue to colorless change indicates negative reaction in negative controls (R1, R2 and R3).

SEQUENCE LISTING

Figure 1A:
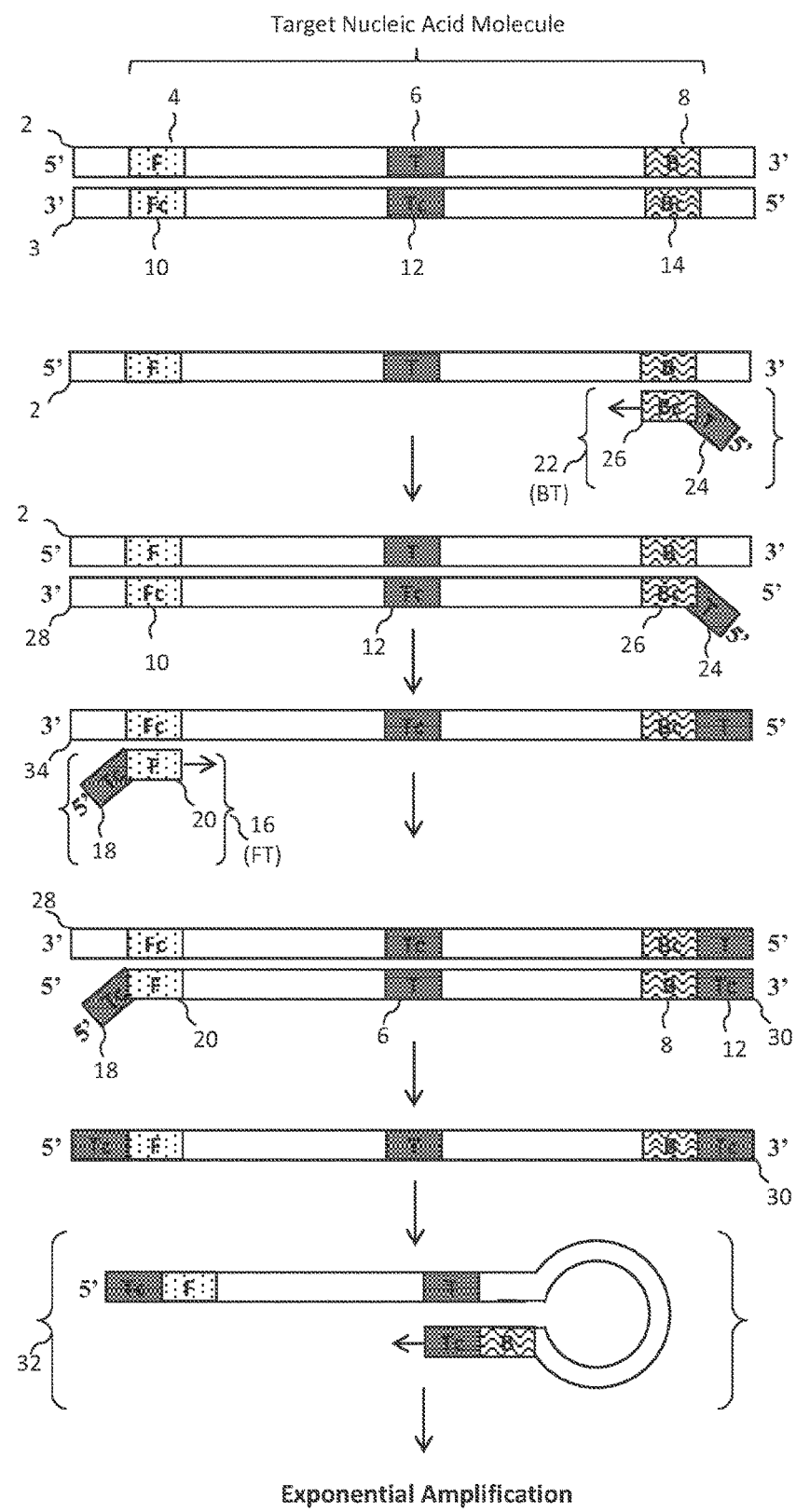
FIGS. 1A-1C are a series of schematic diagrams illustrating an embodiment of the disclosed Genome Exponential Amplification Reaction (GEAR) assay using a set of two primers: a forward turn-back primer 22 and a reverse turn-back primer 16 (FIGS. 1A-1B). Additional primers for use in the GEAR assay (internal forward primer 54 and internal reverse primer 52) are illustrated in FIG. 1C.

Any nucleic acid and amino acid sequences listed herein or in the accompanying sequence listing are shown using standard letter abbreviations for nucleotide bases, and three letter code for amino acids, as defined in 37 C.F.R. §1.822. In at least some cases, only one strand of each nucleic acid sequence is shown, but the complementary strand is understood as included by any reference to the displayed strand.

The Sequence Listing is submitted as an ASCII text file in the form of the file named "Sequence.txt" (~8 kb), which was created on Jan. 28, 2015, which is incorporated by reference herein. In the provided sequences:

SEQ ID NO: 1 is nucleotides 1308-1415 of GEN-BANK™ Accession No. GU594309, incorporated by reference herein as present in the database on Jul. 6, 2012.

SEQ ID NOs: 2-11 are the nucleotide sequences of oligonucleotide primers.

SEQ ID NO: 12 is the nucleotide sequence of the ctxA gene of *V. cholerae* (GenBank Accession# K02679, incorporated by reference herein as present in the database on Mar. 6, 2012).

SEQ ID NOs: 13-30 are the nucleotide sequences of oligonucleotide primers.

DETAILED DESCRIPTION

A wide variety of isothermal amplification techniques have been reported, including Strand Displacement Amplification (SDA; Walker et al., *Nucleic Acids Res.,* 20:1691-1696, 1992), Rolling Circle Amplification (RCA; Lizardi et al., *Nat. Genet.,* 19:225-232, 1998), Loop-Mediated Isothermal Amplification (LAMP; Notomi et al., *Nucleic Acids Res.,* 28:E63, 2000), Multiple Displacement Amplification (MDA; Dean et al., *Proc. Natl. Acad. Sci. U.S.A.,* 99:5261-5266, 2002), Helicase-Dependent Amplification (tHDA; Vincent et al., *EMBO Rep.,* 5:795-800, 2004; Goldmeyer et al., *J. Mol. Diagn.,* 9:639-644, 2007), Isothermal and Chimeric primer-initiated Amplification of Nucleic acids (ICAN; Uemori, et al., *J. Biochem.,* 142:283-292, 2007), self-sustained sequence replication reaction (3SR; Guatelli et al., *Proc. Natl. Acad. Sci. U.S.A.,* 87:1874-1878, 1990), nucleic acid sequence-based amplification (NASBA; Compton, *Nature,* 350:91-92, 1991), Transcription Mediated Amplification (TMA; Pasternack et al., *J. Clin. Microbiol.,* 35:676-678, 1997), Exponential Amplification Reaction (EXPAR; Nagamine et al., *Mol. Cell. Probes,* 16:223-229, 2002), Single Primer Isothermal Amplification (SPIA; Kurn et al., *Clin. Chem.,* 51:1973-1981, 2005), Smart Amplification Process (SmartAmp; Mitani et al., *Nat. Methods,* 4:257-262, 2007), and cross-priming amplification (CPA; Fang et al., *J. Clin. Microbiol.,* 47:845-847, 2009; Yulong et al., *Mol. Cell Probes,* 24:396-400, 2010).

SDA, SPIA, NASBA, TMA, ICAN and tHDA require multiple enzymes (two or more) and require rigorous optimization. LAMP and SmartAmp can be efficiently performed at temperatures of ≥60° C. to increase the specificity of amplification, but these techniques require outer strand displacement primers (SmartAmp and LAMP), five primers (SmartAmp) or at least four primers targeting six regions of the template nucleic acid (LAMP) for efficient results.

The new Genome Exponential Amplification Reaction (GEAR) method provided herein includes the use of a single enzyme (a strand displacement polymerase), use of two or four primers targeting three or five regions of the template, respectively, does not require outer strand displacement primers, and can be performed at amplification temperatures of ≥60° C. to allow for a robust and specific amplification reaction.

I. Terms

Unless otherwise noted, technical terms are used according to conventional usage. Definitions of common terms in molecular biology may be found in Benjamin Lewin, Genes X, published by Jones & Bartlett Publishers, 2009; and Meyers et al. (eds.), *The Encyclopedia of Cell Biology and Molecular Medicine,* published by Wiley-VCH in 16 volumes, 2008.

As used herein, the singular forms "a," "an," and "the," refer to both the singular as well as plural, unless the context clearly indicates otherwise. Similarly, the word "or" is intended to include "and" unless the context clearly indicates otherwise. Also, as used herein, the term "comprises" means "includes." Hence "comprising A or B" means including A, B, or A and B. In addition, the materials, methods, and examples are illustrative only and not intended to be limiting.

All GenBank Accession numbers are incorporated herein for the sequence present on Jul. 23, 2012, unless specifically noted otherwise.

In order to facilitate review of the various embodiments of the disclosure, the following explanations of specific terms are provided:

3' end: The end of a nucleic acid molecule that does not have a nucleotide bound to it 3' of the terminal residue.

5' end: The end of a nucleic acid sequence where the 5' position of the terminal residue is not bound by a nucleotide.

Amplification of a nucleic acid molecule: Refers to use of a technique that increases the number of copies of a nucleic acid molecule (e.g., a DNA or RNA molecule, such as cDNA) in a sample. Several embodiments include isothermal amplification of a nucleic acid molecule.

An example of amplification is polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. PCR reactions typically include a series of 20-40 repeated temperature changes, called cycles, with each cycle commonly consisting of 2-3 discrete temperature steps. For example, each cycle typically includes at least a denaturation step at a temperature of about 95° C. and a annealing/extension step at a temperature of about 60° C. The product of amplification can be characterized by electrophoresis, restriction endonuclease cleavage patterns, oligonucleotide hybridization or ligation, and/or nucleic acid sequencing using standard techniques.

Isothermal amplification of nucleic acid molecules refers to nucleic acid amplification methods that do not require temperature cycling for the denaturation, annealing or extension steps (though a single initial denaturation step may be included in isothermal amplification assays, for example, prior to addition of the polymerase to the assay). Thus, in contrast to PCR methods, these steps are performed at a single temperature in isothermal amplification assays, whereas multiple temperatures are used in PCR assays. Several isothermal amplification methods are known to the person of ordinary skill in the art (see, for example, Gill and Ghaemi, *Nucleosides Nucleotides Nucleic Acids,* 27:224-243, 2008) and are further discussed herein.

Biological sample: A sample including biological material, for example a sample obtained from a subject, or an environmental sample containing biological material. For example, biological samples include all clinical samples useful for detection of disease or infection in subjects. Appropriate samples include any conventional biological samples, including clinical samples obtained from a human or veterinary subject. Exemplary samples include, without limitation, cells, cell lysates, blood smears, cytocentrifuge preparations, cytology smears, bodily fluids (e.g., blood, plasma, serum, saliva, sputum, urine, bronchoalveolar lavage, semen, cerebrospinal fluid (CSF), etc.), tissue biopsies or autopsies, fine-needle aspirates, and/or tissue sections. A sample may also include environmental samples, for example, food, soil, air, or water (such as water from cooling towers, swimming pools, domestic water systems, fountains, or freshwater creeks or ponds). In one example the biological sample is a plant sample.

Conservative variant: A "conservative variant" of a probe or primer includes sequences that have altered nucleic acid sequences, but retain their ability to bind to the target sequences (and identify or amplify the target sequence) with sufficient specificity. In some particular examples, no more than about 1, 2, 5, or 10 nucleic acids are changed, or the probe or primer retains at least 80%, 85%, 90%, or 95% sequence identity to the original sequence. Conservative variants also include probe or primer sequences to which additional sequence has been added, while still retaining the noted specificity of the probe or primer.

Change: To become different in some way, for example to be altered, such as increased or decreased. A detectable change is one that can be detected, such as a change in the intensity, frequency or presence of an electromagnetic signal, such as fluorescence. In particular examples, the detectable change is an increase in fluorescence intensity.

Consists of: With regard to a polynucleotide (such as a probe or primer), a polynucleotide consists essentially of a specified nucleotide sequence if it does not include any additional nucleotides. However, the polynucleotide can include additional non-nucleic acid components, such as labels (for example, fluorescent, radioactive, or solid particle labels), sugars or lipids. With regard to a polynucleotide, a polynucleotide that consists of a specified nucleotide sequence does not include any additional nucleotides, nor does it include additional non-nucleic acid components, such as lipids, sugars or labels.

Control: A sample or standard used for comparison with an experimental sample. In some embodiments, the control is a sample obtained from a healthy subject (or a plurality of healthy subjects), such as a subject not expected to have the target nucleic acid sequence. In additional embodiments, the control is a historical control or standard reference value or range of values (such as a previously tested control sample or plurality of such samples), or group of samples that represent baseline or normal values.

Contacting: Placement in direct physical association, for example solid, liquid or gaseous forms. Contacting includes, for example, direct physical association of fully- and partially-solvated molecules.

Detecting: To identify the existence, presence, or fact of something. General methods of detecting are known to the skilled artisan and may be supplemented with the protocols and reagents disclosed herein. For example, included herein are methods of detecting a nucleic acid molecule in sample. Detection can include a physical readout, such as fluorescence or a reaction output.

Diagnosis: The process of identifying a disease by its signs, symptoms and results of various tests. The conclusion reached through that process is also called "a diagnosis." Forms of testing commonly performed include blood tests, medical imaging, urinalysis, and biopsy.

Hybridization: The terms "annealing" and "hybridization" refer to the formation of base pairs between complementary regions of DNA, RNA, or between DNA and RNA of nucleic acids. Examples of annealing and hybridization include formation of base pairs between two separate nucleic acid molecules, as well as formation of base pairs between nucleic acids on a single nucleic acid molecule.

In some examples, hybridization is between two complementary nucleic acid sequences, for example nucleic acid sequences that are at least 90% complementary to each other, such as at least 91%, 92%, 93%, 94%, 95%, 96%, 97%, 98%, 99%, or 100% complementary to each other.

In additional embodiments, hybridization conditions resulting in particular degrees of stringency and specificity will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) *Molecular Cloning*, second edition, Cold Spring Harbor Laboratory, Plainview, N.Y. (chapters 9 and 11). The following is an exemplary set of hybridization conditions and is not limiting:

Very High Stringency (detects sequences that share at least 90% identity)
Hybridization: 5×SSC at 65° C. for 16 hours
Wash twice: 2×SSC at room temperature (RT) for 15 minutes each
Wash twice: 0.5×SSC at 65° C. for 20 minutes each
High Stringency (detects sequences that share at least 80% identity)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each
Low Stringency (detects sequences that share at least 50% identity)
Hybridization: 6×SSC at RT to 55° C. for 16-20 hours
Wash at least twice: 2×-3×SSC at RT to 55° C. for 20-30 minutes each.

In some embodiments, the probes and primers disclosed herein can hybridize to nucleic acid molecules under low stringency, high stringency, and very high stringency conditions.

Isolated: An "isolated" biological component (such as a nucleic acid molecule or protein) has been substantially separated or purified away from other biological components in the cell of the organism in which the component naturally occurs. The term "isolated" does not require absolute purity. Nucleic acids and proteins that have been "isolated" include nucleic acids and proteins purified by standard purification methods. The term also embraces nucleic acids and proteins prepared by recombinant expression in a host cell, as well as chemically synthesized nucleic acids.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. It will be understood that when a nucleotide sequence is represented by a DNA sequence (i.e., A, T, G, C), this also includes an RNA sequence (i.e., A, U, G, C) in which "U" replaces "T."

"Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (for example, rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns. In some examples, a nucleic acid encodes a disclosed antigen.

Oligonucleotide: A linear polynucleotide sequence of between 5 and 100 nucleotide bases in length.

Primers: Primers are short nucleic acid molecules, usually DNA oligonucleotides, of about 10-50 nucleotides in length. Primers can be annealed to a complementary target DNA strand by nucleic acid hybridization to form a hybrid between the primer and the target DNA strand. A primer can be extended along the target nucleic acid molecule by a polymerase enzyme. Therefore, primers can be used to amplify a target nucleic acid molecule, wherein the sequence of the primer is specific for the target nucleic acid molecule, for example so that the primer will hybridize to the target nucleic acid molecule under very high stringency hybridization conditions.

Typically, primers are at least about 10 nucleotides in length, such as at least about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or about 50 nucleotides in length. For example, a primer can be about 10-50 nucleotides in length, such as, 12-15, 12-20, 12-25, 12-30, 12-35, 12-40, 12-45, 12-50, 14-15, 14-16, 14-18, 14-20, 14-25, 14-30, 15-16, 15-18, 15-20, 15-25, 15-30, 15-35, 15-40, 15-45, 15-50, 16-17, 16-18, 16-20, 16-22, 16-25, 16-30, 16-40, 16-50, 17-18, 17-20, 17-22, 17-25, 17-30, 18-19, 18-20, 18-22, 18-25, 18-30, 19-20, 19-22, 19-25, 19-30, 20-21, 20-22, 20-25, 20-30, 20-35, 20-40, 20-45, 20-50, 21-22, 21-25, 21-30, 22-25, 22-30, 22-40, 22-50, 23-24, 23-25, 23-30, 24-25, 24-30, 25-30, 25-35, 25-40 or 25-45, 25-50 nucleotides in length. Primers can also be of a maximum length, for example no more than 15, 25, 25, 40, 50, 75 or 100 nucleotides in length.

Primer pairs can be used for amplification of a nucleic acid sequence, for example, using the isothermal amplification methods described herein, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence.

Methods for preparing and using nucleic acid primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). Primers can be derived from a known sequence, for example, by using computer programs intended for that purpose such as Primer (Version 0.5, 1991, Whitehead Institute for Biomedical Research, Cambridge, Mass.). One of ordinary skill in the art will appreciate that the specificity of a particular primer increases with its length. Thus, in order to obtain greater specificity, primers can be selected that include at least 10, at least 15, at least 20, at least 25, at least 30, at least 35, at least 40, at least 45, at least 50 or more consecutive nucleotides of a target sequence.

In some embodiments, probes and primers are used in combination in a real-time amplification assay.

A turn-back primer is a primer having a first segment and a second segment, the first segment is 5' to the second segment. The second segment is capable of hybridizing to a target nucleic acid sequence and initiating synthesis of a complementary strand to the target nucleic acid sequence. The first segment "turns-back" and is capable of hybridizing to the complementary strand. Synthesis of an additional complementary strand (complementary to the first complementary strand) is initiated from the first segment of the turn-back primer.

A strand displacement primer is a primer used in a nucleic acid amplification assay for enhancing separation of sense and anti-sense strands of a double stranded nucleic acid molecule. An outer strand displacement primer is a primer that anneals to a region of a nucleic acid molecule that is not part of the target nucleic acid molecule on the nucleic acid molecule; strand synthesis initiated from the outer strand displacement primer enhances separation of the sense and anti-sense nucleic acid molecules of the target nucleic acid molecule. Examples of outer strand displacement primers include the F3 and B3 primers for use with the LAMP assay (see Notami et al., *Nucl. Acid. Res.*, 28:e63, 2000 and U.S. Pat. No. 8,017,357). An inner strand displacement primer is a primer that anneals to a region of a nucleic acid molecule that is part of the target nucleic acid molecule on the nucleic acid molecule; strand synthesis initiated from the inner strand displacement primer enhances separation of the sense and anti-sense nucleic acid molecules of the target nucleic acid molecule. Several embodiments include and amplification methods that does not include use of outer strand displacement primers.

Probe: A short sequence of nucleotides, such as at least 8, at least 10, at least 15, at least 20, at least 25, or at least 30 nucleotides in length, used to detect the presence of a complementary sequence by molecular hybridization. In particular examples, probes include a label that permits detection of probe:target sequence hybridization complexes. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al., *Molecular Cloning: A Laboratory Manual*, Cold Spring Harbor Laboratory Press (1989) and Ausubel et al., *Current Protocols in Molecular Biology*, Greene Publishing Associates and Wiley-Intersciences (1987).

In a particular example, a probe includes at least one fluorophore, such as an acceptor fluorophore or donor fluorophore. For example, a fluorophore can be attached at the 5'- or 3'-end of the probe. In specific examples, the fluorophore is attached to the base at the 5'-end of the probe, the base at its 3'-end, the phosphate group at its 5'-end or a modified base, such as a T internal to the probe.

Probes are generally at least 10 nucleotides in length, such as at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 51, 52, 53, 54, 55, 56, 57, 58, 59, 60, or more contiguous nucleotides complementary to the target nucleic acid molecule, such as 10-60 nucleotides, 30-60 nucleotides, 20-50 nucleotides, 30-50 nucleotides, 20-40 nucleotides, or 10-40 nucleotides. Probes can also be of a maximum length, for example no more than 15, 25, 25, 40, 50, 75 or 100 nucleotides in length.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Sequence identity: The similarity between two nucleic acid sequences is expressed in terms of the similarity between the sequences, otherwise referred to as sequence identity. Sequence identity is frequently measured in terms of percentage identity, similarity, or homology; a higher percentage identity indicates a higher degree of sequence similarity.

The NCBI Basic Local Alignment Search Tool (BLAST), Altschul et al., *J. Mol. Biol.* 215:403-10, 1990, is available from several sources, including the National Center for Biotechnology Information (NCBI, Bethesda, Md.), for use in connection with the sequence analysis programs blastp, blastn, blastx, tblastn and tblastx. It can be accessed through the NCBI website. A description of how to determine sequence identity using this program is also available on the website.

When less than the entire sequence is being compared for sequence identity, homologs will typically possess at least 75% sequence identity over short windows of 10-20 amino acids, and can possess sequence identities of at least 85% or at least 90% or 95% depending on their similarity to the reference sequence. Methods for determining sequence identity over such short windows are described, for example on the NCBI website.

These sequence identity ranges are provided for guidance only; it is entirely possible that strongly significant homologs could be obtained that fall outside of the ranges provided.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Conditions for nucleic acid hybridization and calculation of stringencies can be found in Sambrook et al.; and Tijssen, *Hybridization With Nucleic Acid Probes, Part I: Theory and Nucleic Acid Preparation*, Laboratory Techniques in Biochemistry and Molecular Biology, Elsevier Science Ltd., 1993.

Sensitivity and specificity: Statistical measurements of the performance of a binary classification test. Sensitivity measures the proportion of actual positives which are correctly identified (e.g., the percentage of samples that are identified as including nucleic acid from a particular virus). Specificity measures the proportion of negatives which are correctly identified (e.g., the percentage of samples that are identified as not including a target nucleic acid, such as a nucleic acid from a particular virus or bacteria).

Signal: A detectable change or impulse in a physical property that provides information. In the context of the disclosed methods, examples include electromagnetic signals such as light, for example light of a particular quantity or wavelength. In certain examples, the signal is the disappearance of a physical event, such as quenching of light.

Strand-displacement DNA polymerase: A polymerase enzyme with strand displacement activity. Non-limiting examples of strand-displacement polymerases include Bst DNA polymerase (large fragment), Bca(exo-) DNA polymerase, Klenow fragment of DNA polymerase I, VENT™ DNA polymerase, Vent(Exo-) DNA polymerase (exonuclease activity-free Vent DNA polymerase, DEEPVENT™ DNA polymerase, DEEPVENT™ (Exo-) DNA polymerase (exonuclease activity-free DeepVent DNA polymerase). These polymerases are known to the person of ordinary skill in the art and are commercially available, for example, from New England Biolabs, Ipswich, Mass. In several examples, Bst DNA polymerase (large fragment) is used as a strand-displacement DNA polymerase.

Subject: Any mammal, such as humans, non-human primates, pigs, sheep, cows, rodents and the like. In two non-limiting examples, a subject is a human subject or a murine subject. Thus, the term "subject" includes both human and veterinary subjects.

Target nucleic acid molecule: A nucleic acid molecule whose amplification, detection, quantitation, qualitative detection, or a combination thereof, is intended. For example, the target can be a defined region or particular portion of a nucleic acid molecule, for example a portion of a genome (such as a gene or a region of DNA or RNA containing a gene (or portion thereof) of interest). The nucleic acid molecule need not be in a purified form. Various other nucleic acid molecules can also be present with the target nucleic acid molecule. For example, the target nucleic acid molecule can be a specific nucleic acid molecule (which can include RNA or DNA), the amplification of at least a portion thereof (such as a portion of a genomic sequence or cDNA sequence) is intended. In some examples, a target nucleic acid includes a viral nucleic acid molecule, or a bacterial nucleic acid molecule, such as a nucleic acid molecule from *Escherichia coli* or *Vibrio cholera*. Purification or isolation of the target nucleic acid molecule, if needed, can be conducted by methods known to those in the art, such as by using a commercially available purification kit or the like.

Under conditions sufficient for: A phrase that is used to describe any environment that permits a desired activity. In one example the desired activity is amplification of a nucleic acid molecule.

II. GEAR Assays for Amplifying and Identifying Target Nucleic Acid Molecules

Several embodiments include methods for amplification and/or identification of a target nucleic molecule in a sample using the GEAR method disclosed herein. The provided methods can be used for any purpose wherein isothermal amplification of nucleic acid molecules from a sample is desirable, including diagnostic and prognostic applications, such as in laboratory and clinical settings. The provided GEAR method includes strand displacement DNA synthesis that is performed by a polymerase with strand displacement activity and a set of either two or four primers designed for isothermal amplification of a specific target nucleic acid molecule (see also, Prithiviraj et al., *Biochem. Biophys. Res. Commun.*, 420:738-742, 2012, incorporated by reference herein in its entirety). In embodiments using two primers, the primers hybridize to three regions of the target nucleic acid molecule. In embodiments using four primers, the primers hybridize to five regions of the target nucleic acid molecule.

The GEAR assay is useful for amplification and/or identification of a target nucleic acid molecule from a sample. Typically, the target nucleic acid molecule for GEAR assays includes, from 5' to 3', a 5'-end region (F), a center region (T) and a 3'-end region (B). In additional embodiments, the target nucleic acid molecule includes an internal forward region and an internal reverse region, and the regions are positioned, from 5' to 3', as follows: the 5'-end region (F), the internal reverse region (IR), the center region (T), the internal forward region (IF) and the 3'-end region (B).

GEAR assays include use of a forward turn-back primer (FT) and a reverse turn-back primer (BT), which each include a first segment and a second segment. The first segment is 5' to the second segment. The second segment of the forward turn-back primer includes a nucleotide sequence that hybridizes to the complement of the 5'-end region (Fc), and the first segment of the forward turn-back primer includes a nucleotide sequence that hybridizes to the sequence of the center region (T). The second segment of the reverse turn-back primer includes a nucleotide sequence that hybridizes to the 3'-end region (B) and the first segment of the reverse turn-back primer includes a nucleotide sequence that hybridizes to the complementary sequence of the center region (Tc). Thus, the forward and reverse turn-back primers target three regions of the target nucleic acid molecule: the 5'-end region (F), the center region (T) and the 3'-end region (B).

With reference to FIG. 1A, in several embodiments, the disclosed GEAR method includes amplification and/or detection of target nucleic acid molecule 2. Target nucleic acid molecule 2 includes, from 5' to 3', 5'-end region 4 (F), center region 6 (T) and 3'-end region 8 (B). The complement of target nucleic acid molecule 2 includes complementary sequence 3 that includes, from 5' to 3', complement of 3'-end region 14 (Bc) complement of center region 12 (Tc) and complement of 5'-end region 10 (Fc). The GEAR method includes use of forward turn-back primer 16 (FT) and reverse turn-back primer 22 (BT). Both the forward and reverse turn-back primers include a first segment 5' to a second segment. First segment 18 of forward turn-back primer 16 includes the nucleotide sequence of complement of center region 12 (Tc) and second segment 20 of forward turn-back primer 16 includes the nucleotide sequence of 5'-end region 4 (F). First segment 24 of reverse turn-back primer 22 includes the nucleotide sequence of center region 6 (T), and second segment 26 of reverse turn-back primer 22 includes the nucleotide sequence of complement of 3'-end region 14 (Bc).

The person of ordinary skill in the art will understand that, in some embodiments, primers for use in the GEAR assay do not need to be 100% identical or 100% complementary to the corresponding region of the target nucleic acid molecule. For example, in some embodiments, the primers can be substantially identical to or complementary to the corresponding region of the target nucleic acid molecule, such as at least 90% identical to the corresponding region of the target nucleic acid molecule (for example at least 91%, 92%, 93%, 94%, 95%, 96%, 97%, 98% or 99% identical to complementary to the corresponding region of the target nucleic acid molecule. In one example, the primers can be substantially identical to or complementary to the corresponding region of the target nucleic acid molecule, such as having no more than 5 nucleotide substitutions, deletions and/or insertions, such as 5, 4, 3, 2 or 1, such as 1-5, 1-4, 1-3, 2-4, or 1-2 nucleotide substitutions, deletions and/or insertions. Additional description of primers for the GEAR assay is provided below.

With reference to FIG. 1A, in some embodiments, initiation of the GEAR method proceeds as follows: second segment 26 of reverse turn-back primer 22 hybridizes to 3'-end region 8 (B) of target nucleic acid molecule 2. The strand displacement polymerase catalyzes complementary strand synthesis to form complementary strand 28, which includes, from 5' to 3', first segment 24 of reverse turn-back primer 22, second segment 26 of reverse turn-back primer 22, complement of center region 12 (Tc) and complement of 5' region 10 (Fc).

Complementary strand 28 serves as the template nucleic acid for the next step of the GEAR method, which includes hybridization of second segment 20 of forward turn-back primer 16 to complement of 5'-end region 10 (Fc) of complementary strand 28. The strand displacement polymerase catalyzes complementary strand synthesis to form complementary strand 30, which includes, from 5' to 3', first segment 18 of forward turn-back primer 16, second segment 20 of forward turn-back primer 16, center region 6 (T), 3' region 8 and complement of center region 12. As shown in FIG. 1A, complementary strand 30 forms C-clamp like nucleic acid structures 32 in a series of cycling stages, which serve as starting material for exponential nucleic acid amplification of the GEAR assay.

The person of ordinary skill in the art will understand that initiation of the GEAR assay can also begin from hybridization of the forward turn-back primer to the target nucleic acid molecule. Thus, in embodiments where the target nucleic acid molecule is a double-stranded nucleic acid molecule the GEAR assay can proceed from each strand (sense and anti-sense, e.g., 2 and 3 of FIG. 1A) of the target nucleic acid molecule, for example, as illustrated in FIG. 1B.

Figure 1B:
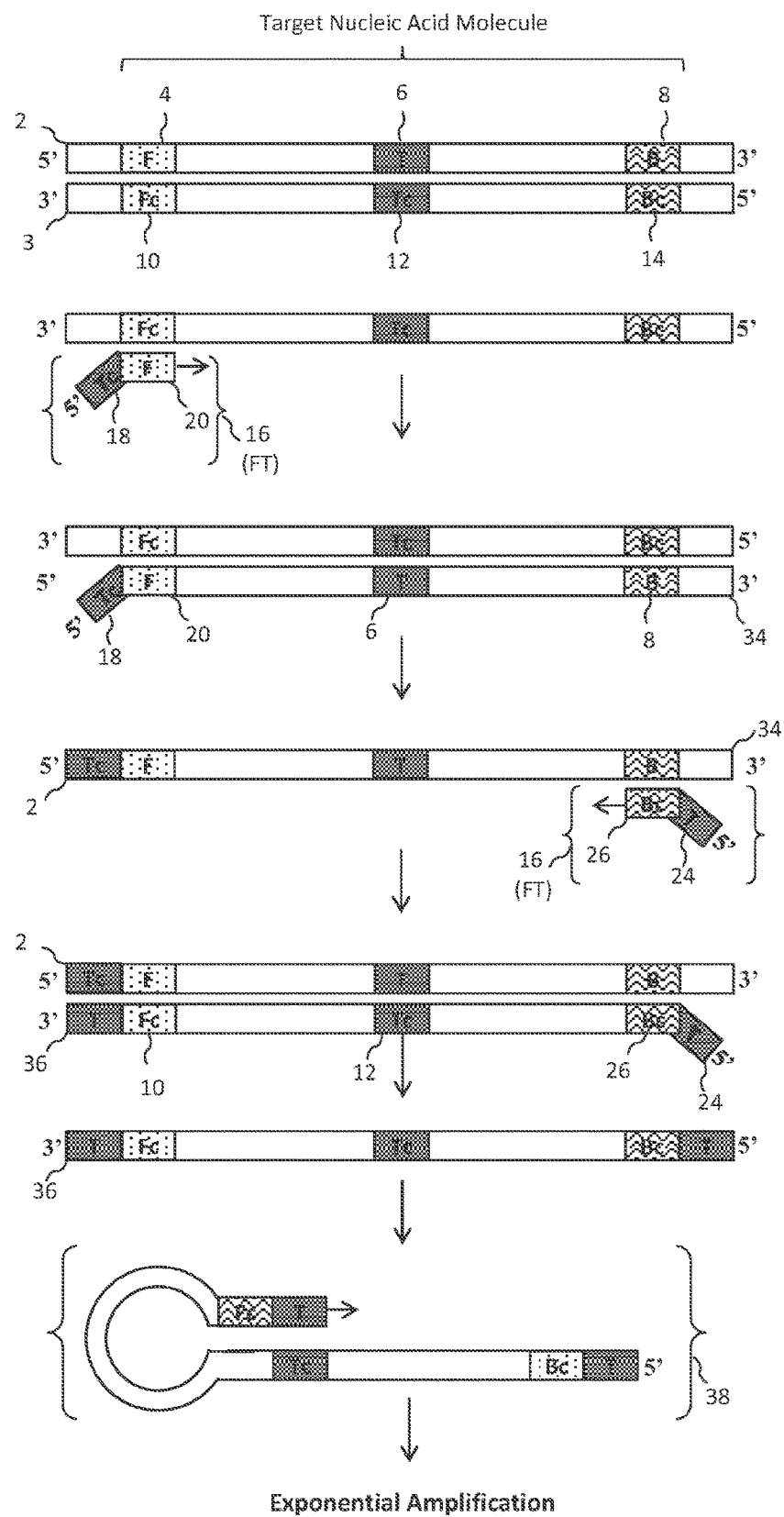

Thus, in parallel to the amplification procedure illustrated in FIG. 1A, in several embodiments, the GEAR method proceeds as illustrated in FIG. 1B: second segment 20 of forward turn-back primer 16 hybridizes to complement of 5'-end region 10 (Fc) of complementary sequence 3 of target nucleic acid molecule 2. The strand displacement polymerase catalyzes complementary strand synthesis to form complementary strand 34, which includes, from 5' to 3', first segment 18 of forward turn-back primer 16, second segment 20 of forward turn-back primer 16 center region 6 (T) and 3' region 8 (Fc).

Complementary strand 34 serves as the template nucleic acid for the next step of the GEAR method, which includes hybridization of second segment 26 of reverse turn-back primer 22 to the 5'-end region 8 (B) of complementary strand 28. The strand displacement polymerase catalyzes complementary strand synthesis to form complementary strand 36, which includes, from 5' to 3', first segment 24 of reverse turn-back primer 22, second segment 26 of reverse turn-back primer 22, complement of center region 12 (Tc), complement of 5' region 12 (Tc) and center region 6 (T). As shown in FIG. 1B, complementary strand 36 forms C-clamp like nucleic acid structures 38 in a series of cycling stages, which serve as starting material for exponential nucleic acid amplification of the GEAR assay.

In additional embodiments, the GEAR assay further includes use of an internal forward primer (IF), which hybridizes to the complement of the internal forward region, and an internal reverse primer (IR) which hybridizes to the internal reverse region of the target nucleic acid molecule. For example, with reference to FIG. 1C, in several embodiments, the disclosed GEAR method includes amplification and/or detection of target nucleic acid molecule 40. Target nucleic acid molecule 40 includes, from 5' to 3', 5'-end region 4 (F), internal reverse region 42 (IR), center region 6 (T), internal forward region 44 (IF), and 3'-end region 8 (B). The complement of target nucleic acid molecule 40 includes complementary sequence 46 that includes, from 5' to 3', complement of 3'-end region 14 (Bc), complement of internal forward region 50, complement of center region 12 (Tc), complement of internal reverse region 48 and complement of 5'-end region 10 (Fc). In such embodiments, internal reverse primer 52 hybridizes to the internal reverse region 42, and internal forward primer 54 hybridizes to complement of internal forward region 50. Complementary strand synthesis is initiated from the internal forward and internal reverse primers. The use of the IR and IF primers in combination with the FT and BT primers is optional, but can be used to, for example, increase the speed and sensitivity of the GEAR assay. In some embodiments, the IF and IR primers are added to the reaction at the same time as the FT and BT primers. In other embodiments, the IF and IR primers are added to the reaction after the FT and BT primers are added to the reaction.

Figure 1C:
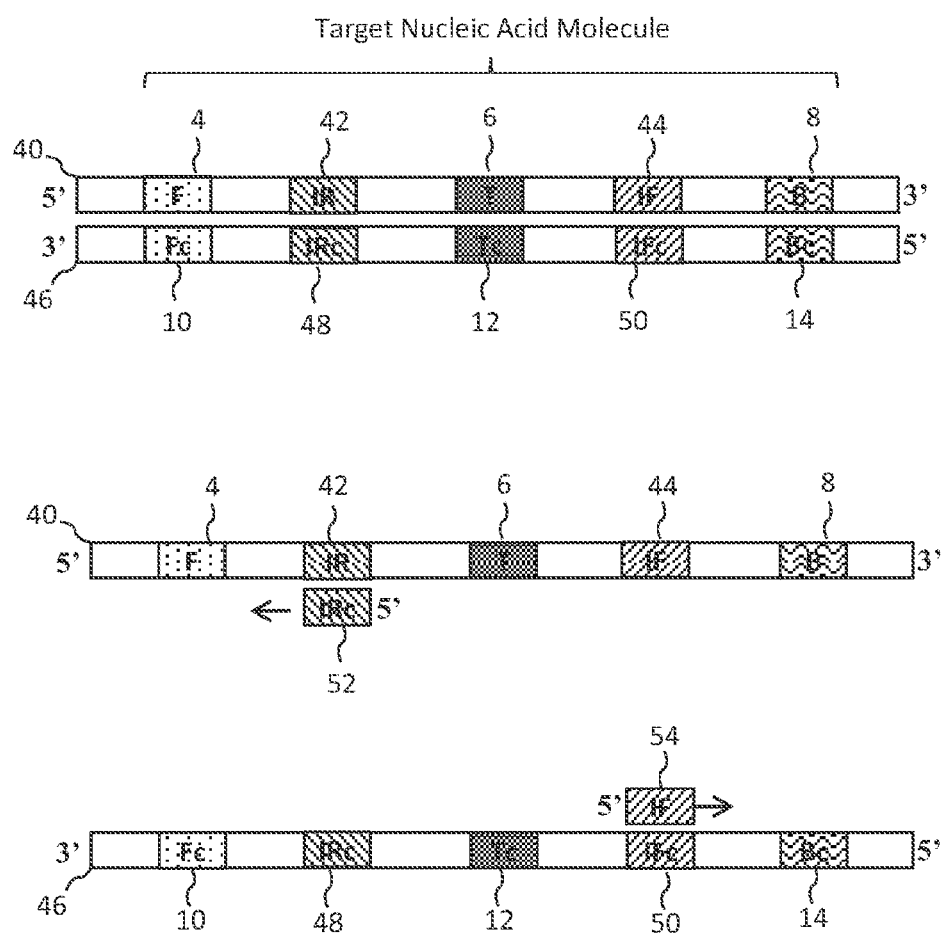
Figure 2C:
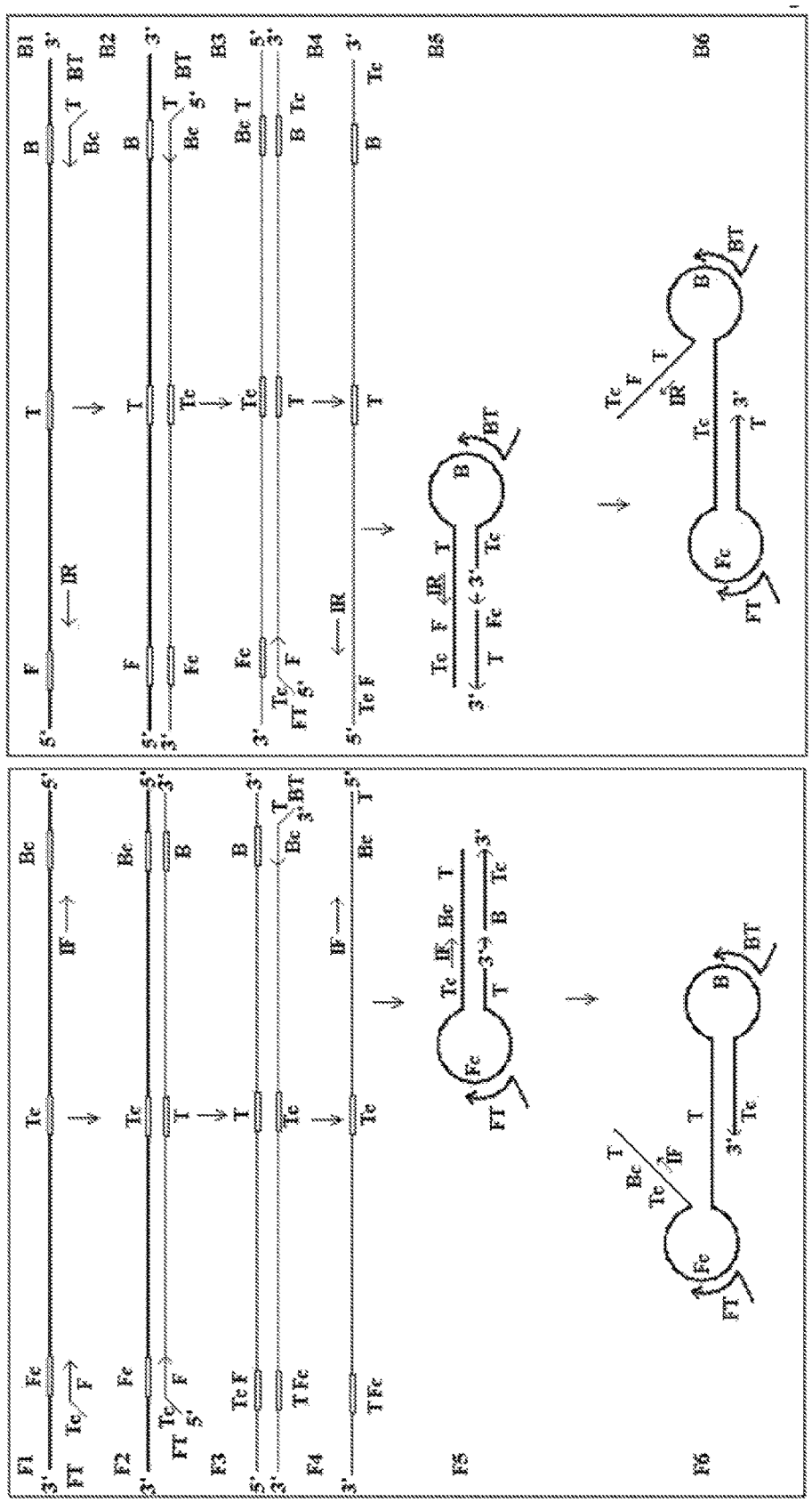

The embodiments illustrated in FIGS. 1A-1C are further illustrated in FIG. 2C. With reference to the left panel of FIG. 2C, the second segment of the forward turn-back primer hybridizes to the complement of the 5'-end region (Fc) in the target DNA (step F1) and initiates complementary strand synthesis (step F2). The second segment of the reverse turn-back primer hybridizes to the complementary sequence corresponding to the 3'-end region (B) of the amplicon generated in step F2 and initiates complementary strand synthesis (step F3) to form the amplicon shown in step F4. This amplicon includes, from 5' to 3', the sequence of the reverse turn-back primer, the sequence of the complement of the center region, and the sequence of the complement of the forward turn-back primer. The amplification reaction then produces C-clamp like DNA structures in a series of cycling stages (F5 and F6), which serve as the starting material for the exponential nucleic acid amplification phase of the GEAR assay.

With reference to the right panel of FIG. 2C, the second segment of the reverse turn-back primer hybridizes to the 3'-end region (B) in the target DNA (step B1) and initiates complementary strand synthesis (step B2). The second segment of the forward turn-back primer then hybridizes to the complementary sequence corresponding to the 5'-end region (Fc) of the amplicon generated in step B2 and initiates complementary strand synthesis (step B3) to form the amplicon shown in step B4. This amplicon includes, from 5' to 3', the sequence of the forward turn-back primer, the sequence of the center region, and the sequence of the complement of the reverse turn-back primer. The amplification step produces C-clamp like DNA structures in a series of cycling stages (B5 and B6), which serve as the starting material for exponential nucleic acid amplification of the GEAR assay.

Several embodiments include amplification according the provided methods using a set of either two or four primers designed for isothermal amplification of a specific target nucleic acid molecule. The methods include contacting the target nucleic acid molecule (or a sample containing the target nucleic acid molecule) with the set of two (forward and reverse turn-back primers) or four (forward and reverse turn-back primers and internal forward and reverse primers) primers designed for isothermal amplification of a specific target nucleic acid molecule under conditions sufficient for isothermal amplification using a strand-displacement polymerase.

Conditions sufficient for isothermal amplification of nucleic acid molecules using a strand displacement polymerase are familiar to the person of ordinary skill in the art. For example, buffer conditions are disclosed in Notami et al., Nucl. Acid. Res., 28:e63, 2000 and U.S. Pat. No. 8,017,357. In one example, the amplification reaction is performed in 20 mM Tris-HCl, pH 8.8, 10 mM KCl, 10 mM (NH4)SO4, 4 mM MgSO4, 0.1 Triton X-100 with 400 µM each dNTP. In one embodiment, the amplification reaction is carried our using the LOOPAMP™ DNA amplification kit (Eiken Chemical, Japan) and the primers described herein for the GEAR assay.

The amplification reaction is typically carried out at about 55-75° C., such as about 55-70, 55-65, 55-60, 60-77, 60-70, 60-65 or 65-70° C. In some embodiments, the amplification reaction is carried out at about 55-75° C., such as about 55, 56, 57, 58, 59, 60, 61, 62, 63, 64, 65, 66, 67, 68, 69, 70, 71, 72, 73, 74 or 75° C.

In some embodiments, the amplification method includes an initial denaturation step, for example, wherein the reaction mixture is heated to 95° C. for five minutes before addition of the strand displacement polymerase to the reaction mixture.

The period of time that the isothermal amplification reaction is allowed to proceed can vary according to the particular conditions of the reaction. For example, in some embodiments, amplifying a target nucleic acid molecule includes contacting the target nucleic acid molecule with a GEAR primer set and a strand displacement polymerase under conditions sufficient for isothermal amplification for a period of at least 10 minutes such as about 11, 12, 13, 14, 15, 16, 17, 18, 19, 20, 21, 22, 23, 24, 25, 26, 27, 28, 29, 30, 35, 40, 45, 50, 55, 60, 75, 90 or about 120 minutes. In additional examples, the period of time can be from about 10-60 minutes, such as about 10-15, 10-20, 10-30, 15-20, 15-30, 20-30 or 30-60 minutes. In several examples, the isothermal amplification reaction is allowed to proceed for a maximum period of time, such as no more than 90 minutes, for example about 10, 15, 20, 25, 30, 45, 60, 75 or 90 minutes.

The provided methods of amplification of nucleic acid molecules include use of a polymerase with strand displacement activity. Non-limiting examples of such polymerases include Bst DNA polymerase (large fragment), Bst 2.0 DNA polymerase (NEB), Bst 2.0 WarmStart DNA Polymerase (NEB), Bst (exo-) DNA Polymerase, Bca(exo-) DNA polymerase, Klenow fragment of DNA polymerase I, VENT™ DNA polymerase, Vent(Exo-) DNA polymerase (exonuclease activity-free Vent DNA polymerase, DEEPVENT™ DNA polymerase, DEEPVENT™ (Exo-) DNA polymerase (exonuclease activity-free DEEPVENT™ DNA polymerase). These polymerases are known to the person of ordinary skill in the art and are commercially available, for example, from New England BioLabs, Ipswich, Mass. In one example, Bst DNA polymerase (large fragment; available commercially from several sources including New England BioLabs, Cat. No. M0275L) is used as a strand-displacement DNA polymerase. The person of skill in the art will understand the amount of strand displacement polymerase to use for the methods of amplification and identification. In one embodiment, at least 1 unit/20 µl assay volume Bst polymerase (large fragment) is used for the amplification, such as at least 2 units/20 µl assay volume Bst polymerase, at least 5 units/20 µl assay volume Bst polymerase, at least 8 units/20 µl assay volume Bst polymerase, or at least 10 units/20 µl assay volume Bst polymerase, for example about 8 units/20 µl assay volume Bst polymerase.

A. Target Nucleic Acid Molecules

Target nucleic acid molecules include single and/or double stranded nucleic acid molecules. The target nucleic acid can be a portion of a longer nucleic acid molecule from a target organism (such as a target pathogen) or target cell (such as a cancer cell), such as a pathogenic genomic, DNA, cDNA, RNA, or mRNA sequence or a tumor-associated genomic, DNA, cDNA, RNA, or mRNA sequence. In some embodiments, the region of the target nucleic acid molecule selected for amplification is based on a gene unique to the organism that provides very high specificity. The design of target-specific primers uses information on genomic function of specific target and DNA sequence template that can be obtained from public databases (e.g., NCBI) for construction of primer design. The designed primers are confirmed for their specificity by aligning against the genome sequence through for example, the NCBI BLAST search engine. If the aligned results show cross-reactivity with non-target genome then redesign the primers from another new template until specific primers obtained.

In several embodiments, the target nucleic acid molecule is at least 30 nucleotides in length, such as at least 35, 40, 45, 50, 55, 60, 65, 70, 75, 80, 85, 90, 95, 100, 110, 120, 130, 140, 150, 160, 170, 180, 190, or 200 nucleotides in length. In some embodiments, the target nucleic acid includes a maximum length of at most 300 nucleotides, such as at most 290, 280, 270, 260, 250, 240, 230, 22, 210, 200, 190, 180, 170, 160, 150, 140, 130, 120, 100, 95, 90, 85, 80, 75, 70, 65, 60, 55, 50 45, 40, 35, or at most 30 nucleotides in length. In some embodiments, the target nucleic acid molecule is from 90 to 250 nucleotides in length, such as from 110 to 160 nucleotides in length.

In some embodiments, the target nucleic acid molecule includes, from 5' to 3', a 5'-end region, a center region, and a 3'-end region, wherein each region includes at least 10 consecutive nucleotides of the target nucleic acid molecule and is non-overlapping. In additional embodiments, the target nucleic acid molecule includes from 5' to 3', a 5'-end region, an internal reverse region, a center region, an internal forward region and a 3'-end region, wherein each region includes at least 10 consecutive nucleotides of the target nucleic acid molecule and is non-overlapping. These regions are at least 10 consecutive nucleotides in length, such as at least 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length. The regions can also include a maximum length, such as at most 50, at most 45, at most 40, at most 35, at most 30, at most 25, at most 20 or at most 15 nucleic acids in length.

In several embodiments, the 5'-end region, the internal reverse region, the center region, the internal forward region and the 3'-end region include a length and a Tm as shown in Table 1. In additional embodiments, the 5'-end region, the internal reverse region, the center region, the internal forward region and the 3'-end region include a length and a Tm as shown in Table 1.

TABLE 1

Non-limiting examples of length and Tm for the 5'-end region, the internal reverse region, the center region, the internal forward region and the 3'-end region of the target nucleic acid molecule.

| Primer | Base pair (length) | Tm (° C.) |
|---|---|---|
| 5' Region | 18-25 | 58-64 |
| 3' Region | 18-25 | 58-64 |
| Center Region | 20-26 | 60-70 |
| Internal Reverse Region | 18-26 | 58-63 |
| Internal Forward Region | 18-26 | 58-63 |

In some embodiments, the length between 5' region and the center region is 18-26 bases and the length between the 3' region and the center region is 18-26 bases In some examples, the target nucleic acid molecule is a nucleic acid from *Escherichia coli*, such as a 16S nucleic acid. For example, in some embodiments, the target nucleic acid molecule includes the nucleotide sequence set forth as SEQ ID NO: 1. In some such embodiments, the target nucleic acid molecule includes, from 5' to 3', a 5'-end region, center region and a 3'-end region, wherein the 5'-end region includes the nucleic acid sequence set forth as nucleotides 1-22 of SEQ ID NO: 1, the center region includes the nucleic acid sequence set forth as nucleotides 46-64 of SEQ ID NO: 1 and the 3'-end region includes the nucleotide sequence set forth as nucleotides 89-108 of SEQ ID NO: 1. In additional embodiments, the target nucleic acid molecule further includes an internal forward region and an internal reverse region, wherein the internal forward region includes the nucleotide sequence set forth as nucleotides 68-85 of SEQ ID NO: 1 and the internal reverse nucleotide region includes the nucleotide sequence set forth as nucleotides 24-45 of SEQ ID NO: 1.

In some examples, the target nucleic acid molecule is a nucleic acid from *Vibrio cholerae*. For example, in some embodiments, the target nucleic acid molecule includes the nucleotide sequence set forth as nucleotides 193-395 of SEQ ID NO: 12. In some such embodiments, the target nucleic acid molecule includes, from 5' to 3', a 5'-end region, and center region and a 3'-end region, wherein the 5'-end region includes the nucleic acid sequence set forth as nucleotides 193-218 of SEQ ID NO: 12, the center region includes a nucleic acid sequence set forth as nucleotides 245-267 of SEQ ID NO: 12 and the 3'-end region includes a nucleotide sequence set forth as nucleotides 292-319 of SEQ ID NO: 12. In additional embodiments, the target nucleic acid molecule further includes an internal forward region and an internal reverse region, wherein the internal forward region includes the nucleotide sequence set forth as nucleotides 269-290 of SEQ ID NO: 12 and the internal reverse nucleotide region includes the nucleotide sequence set forth as nucleotides 220-243 of SEQ ID NO: 12.

In some examples, the target nucleic acid molecule is a nucleic acid from *Homo sapiens*. For example, in some embodiments, the target nucleic acid molecule includes the nucleotide sequence set forth as nucleotides 558-659 of SEQ ID NO: 31. In some such embodiments, the target nucleic acid molecule includes, from 5' to 3', a 5'-end region, and center region and a 3'-end region, wherein the 5'-end region includes the nucleic acid sequence set forth as nucleotides 558-575 of SEQ ID NO: 31, the center region includes a nucleic acid sequence set forth as nucleotides 596-622 of SEQ ID NO: 31 and the 3'-end region includes a nucleotide sequence set forth as nucleotides 642-659 of SEQ ID NO: 31. In additional embodiments, the target nucleic acid molecule further includes an internal forward region and an internal reverse region, wherein the internal forward region includes the nucleotide sequence set forth as nucleotides 624-640 of SEQ ID NO: 31 and the internal reverse nucleotide region includes the nucleotide sequence set forth as nucleotides 578-594 of SEQ ID NO: 31.

In some examples, the target nucleic acid molecule is a nucleic acid from Enterobacterio phage MS2. For example, in some embodiments, the target nucleic acid molecule includes the nucleotide sequence set forth as nucleotides 937-1052 of SEQ ID NO: 32. In some such embodiments, the target nucleic acid molecule includes, from 5' to 3', a 5'-end region, and center region and a 3'-end region, wherein the 5'-end region includes the nucleic acid sequence set forth as nucleotides 937-956 of SEQ ID NO: 32, the center region includes a nucleic acid sequence set forth as nucleotides 982-1004 of SEQ ID NO: 32 and the 3'-end region includes a nucleotide sequence set forth as nucleotides 1032-1052 of SEQ ID NO: 32. In additional embodiments, the target nucleic acid molecule further includes an internal forward region and an internal reverse region, wherein the internal forward region includes the nucleotide sequence set forth as nucleotides 1009-1029 of SEQ ID NO: 32 and the internal reverse nucleotide region includes the nucleotide sequence set forth as nucleotides 959-980 of SEQ ID NO: 32.

In some embodiments, the target nucleic acid molecule is a nucleic acid molecule from a target virus, which can be detected by amplifying a particular region (target) of a viral genome. Non-limiting examples of target viruses include those in the following virus families: Retroviridae (for example, human immunodeficiency virus (HIV), human T-cell leukemia viruses; Picornaviridae (for example, poliovirus, hepatitis A virus, enteroviruses, human coxsackie viruses, rhinoviruses, echoviruses, foot-and-mouth disease virus); Caliciviridae (such as strains that cause gastroenteritis, including Norwalk virus); Togaviridae (for example, alphaviruses (including chikungunya virus, equine encephalitis viruses, Simliki Forest virus, Sindbis virus, Ross River virus, *rubella* viruses); Flaviridae (for example, hepatitis C virus, dengue viruses, yellow fever viruses, West Nile virus, St. Louis encephalitis virus, Japanese encephalitis virus, Powassan virus and other encephalitis viruses); Coronaviridae (for example, coronaviruses, severe acute respiratory syndrome (SARS) virus; Rhabdoviridae (for example, vesicular stomatitis viruses, rabies viruses); Filoviridae (for example, Ebola virus, Marburg virus); Paramyxoviridae (for example, parainfluenza viruses, mumps virus, measles virus, respiratory syncytial virus); Orthomyxoviridae (for example, influenza viruses); Bunyaviridae (for example, Hantaan viruses, Sin Nombre virus, Rift Valley fever virus, bunya viruses, phleboviruses and Nairo viruses); Arenaviridae (such as Lassa fever virus and other hemorrhagic fever viruses, Machupo virus, Junin virus); Reoviridae (e.g., reoviruses, orbiviurses, rotaviruses); Birnaviridae; Hepadnaviridae (hepatitis B virus); Parvoviridae (parvoviruses); Papovaviridae (papilloma viruses, polyoma viruses, BK-virus); Adenoviridae (adenoviruses); Herpesviridae (herpes simplex virus (HSV)-1 and HSV-2; cytomegalovirus; Epstein-Barr virus; varicella zoster virus; and other herpes viruses, including HSV-6); Poxviridae (variola viruses, vaccinia viruses, pox viruses); and Iridoviridae (such as African swine fever virus); Astroviridae; and unclassified viruses (for example, the etiological agents of spongiform encephalopathies, the agent of delta hepatitis (thought to be a defective satellite of hepatitis B virus).

In further embodiments, the target nucleic acid molecule is a nucleic acid molecule from a target bacterial pathogen. Non-limiting examples of target bacterial pathogens include *Helicobacter pylori, Escherichia coli, Vibrio cholerae, Borelia burgdorferi, Legionella pneumophilia, Mycobacteria* sps (such as. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (*anaerobic* sps.), *Streptococcus pneumoniae*, pathogenic *Campylobacter* sp., *Enterococcus* sp., *Haemophilus influenzae, Bacillus anthracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Bordetella pertussis, Shigella flexnerii, Shigella dysenteriae* and *Actinomyces israelli*.

In some embodiments, the target nucleic acid molecule is a nucleic acid molecule from a target fungal pathogen. Non-limiting examples of target fungal pathogens include, but are not limited to: *Cryptococcus neoformans, Histoplasma capsulatum, Coccidioides immitis, Blastomyces dermatitidis, Chlamydia trachomatis* and *Candida albicans.*

In further embodiments, the target nucleic acid molecule is a nucleic acid molecule from a target protozoan pathogen. Non-limiting examples of target protozoan pathogens include *Cryptosporidium parvum, C. hominis, Giardia lamblia, Toxoplasma gondii, Blastocystis hominis, Babesia microti, Cyclospora cayetanensis, Trypanosoma cruzi, Trypanosoma brucei, Leishmania* spp., *Enterocytozoon bieneusi, Encephalitozoon intestinalis*, malaria protozoa (*Plasmodium falciparum, Plasmodium vivax, Plasmodium ovale* and *Plasmodium malariae*), opportunistic free-living amoebas such as *Entamoeba histolytica Naegleria fowleri, Acanthamoeba castellanii* and *Balamuthia mandrillaris*.

Further application of GEAR assay includes the diagnosis of plant and animal diseases.

In some examples, the target nucleic acid molecule is a nucleic acid molecule from a target nucleic acid sequence (e.g., genomic nucleic acid sequence) "associated with" a disease or condition. That is, detection of the target nucleic acid sequence can be used to infer the status of a sample with respect to the disease or condition. For example, the target nucleic acid sequence can exist in two (or more) distinguishable forms, such that a first form correlates with absence of a disease or condition and a second (or different) form correlates with the presence of the disease or condition. The two different forms can be qualitatively distinguishable, such as by polynucleotide polymorphisms, and/or the two different forms can be quantitatively distinguishable, such as by the number of copies of the target nucleic acid sequence that are present in a cell.

In specific non-limiting examples, the genomic target nucleic acid sequence is associated with a neoplasm (for example, a cancer). Numerous chromosome abnormalities (including translocations and other rearrangements, reduplication (amplification) or deletion) have been identified in neoplastic cells, especially in cancer cells, such as B cell and T cell leukemias, lymphomas, breast cancer, colon cancer, neurological cancers and the like. Therefore, in some examples, at least a portion of the target nucleic acid sequence (e.g., genomic target nucleic acid sequence) is reduplicated or deleted in at least a subset of cells in a sample, which can be detected using the disclosed GEAR assay.

Translocations involving oncogenes are known for several human malignancies. For example, chromosomal rearrangements involving the SYT gene located in the breakpoint region of chromosome 18q11.2 are common among synovial sarcoma soft tissue tumors. Numerous examples of reduplication of genes (also known as gene amplification) involved in neoplastic transformation have been observed, and can be detected using the disclosed GEAR assay. In one example, the genomic target nucleic acid sequence is selected to include a gene (e.g., an oncogene) that is reduplicated in one or more malignancies (e.g., a human malignancy). For example, HER2, also known as c-erbB2 or HER2/neu, is a gene that plays a role in the regulation of cell growth (a representative human HER2 genomic sequence is provided at GENBANK™ Accession No. NC_000017, nucleotides 35097919-35138441). HER2 is amplified in human breast, ovarian, gastric, and other cancers. Therefore, a HER2 gene (or a region of chromosome 17 that includes a HER2 gene) can be detected using the GEAR assay.

In other examples, a genomic target nucleic acid sequence is one that is a tumor suppressor gene that is deleted (lost) in malignant cells, and whose loss can be detected using the GEAR assay. For example, the p16 region (including D9S1749, D9S1747, p16(INK4A), p14(ARF), D9S1748, p15(INK4B), and D9S1752) located on chromosome 9p21 is deleted in certain bladder cancers. Chromosomal deletions involving the distal region of the short arm of chromosome 1 (that encompasses, for example, SHGC57243, TP73, EGFL3, ABL2, ANGPTL1, and SHGC-1322), and the pericentromeric region (e.g., 19p13-19q13) of chromosome 19 (that encompasses, for example, MAN2B1, ZNF443, ZNF44, CRX, GLTSCR2, and GLTSCR1) are characteristic molecular features of certain types of solid tumors of the central nervous system.

The aforementioned examples are provided solely for purpose of illustration and are not intended to be limiting. Numerous other cytogenetic abnormalities that correlate with neoplastic transformation and/or growth are known to those of skill in the art. Genomic target nucleic acid sequences, which have been correlated with neoplastic transformation and which can be detected using the GEAR assay, also include but are not limited to: the EGFR gene (7p12; e.g., GENBANK™ Accession No. NC_000007, nucleotides 55054219-55242525), the MET gene (7q31; e.g., GENBANK™ Accession No. NC_000007, nucleotides 116099695-116225676), the C-MYC gene (8q24.21; e.g., GENBANK™ Accession No. NC_000008, nucleotides 128817498-128822856), IGF1R (15q26.3; e.g., GENBANK™ Accession No. NC_000015, nucleotides 97010284-97325282), D5S271 (5p15.2), KRAS (12p12.1; e.g. GENBANK™ Accession No. NC_000012, complement, nucleotides 25249447-25295121), TYMS (18p11.32; e.g., GENBANK™ Accession No. NC_000018, nucleotides 647651-663492), CDK4 (12q14; e.g., GENBANK™ Accession No. NC_000012, nucleotides 58142003-58146164, complement), CCND1 (11q13, GENBANK™ Accession No. NC_000011, nucleotides 69455873-69469242), MYB (6q22-q23, GENBANK™ Accession No. NC_000006, nucleotides 135502453-135540311), lipoprotein lipase (LPL) gene (8p22; e.g., GENBANK™ Accession No. NC_000008, nucleotides 19840862-19869050), RB1 (13q14; e.g., GENBANK™ Accession No. NC_000013, nucleotides 47775884-47954027), p53 (17p13.1; e.g., GENBANK™ Accession No. NC_000017, complement, nucleotides 7512445-7531642), N-MYC (2p24; e.g., GENBANK™ Accession No. NC_000002, complement, nucleotides 15998134-16004580), CHOP (12q13; e.g., GENBANK™ Accession No. NC_000012, complement, nucleotides 56196638-56200567), FUS (16p11.2; e.g., GENBANK™ Accession No. NC_000016, nucleotides 31098954-31110601), FKHR (13p14; e.g., GENBANK™ Accession No. NC_000013, complement, nucleotides 40027817-40138734), as well as, for example: ALK (2p23; e.g., GENBANK™ Accession No. NC_000002, complement, nucleotides 29269144-29997936), Ig heavy chain, CCND1 (11q13; e.g., GENBANK™ Accession No. NC_000011, nucleotides 69165054-69178423), BCL2 (18q21.3; e.g., GENBANK™ Accession No. NC_000018, complement, nucleotides 58941559-59137593), BCL6 (3q27; e.g., GENBANK™ Accession No. NC_000003, complement, nucleotides 188921859-188946169), AP1 (1p32-p31; e.g., GENBANK™ Accession No. NC_000001, complement, nucleotides 59019051-59022373), TOP2A (17q21-q22; e.g., GENBANK™ Accession No. NC_000017, complement, nucleotides 35798321-35827695), TMPRSS (21q22.3; e.g., GENBANK™ Accession No. NC_000021, complement, nucleotides 41758351-41801948), ERG (21q22.3; e.g., GENBANK™ Accession No. NC_000021, complement, nucleotides 38675671-38955488); ETV1 (7p21.3; e.g., GENBANK™ Accession No. NC_000007, complement, nucleotides 13897379-13995289), EWS (22q12.2; e.g., GENBANK™ Accession No. NC_000022, nucleotides 27994017-28026515); FLI1 (11q24.1-q24.3; e.g., GENBANK™ Accession No. NC_000011, nucleotides 128069199-128187521), PAX3 (2q35-q37; e.g., GENBANK™ Accession No. NC_000002, complement, nucleotides 222772851-222871944), PAX7 (1p36.2-p36.12; e.g., GENBANK™ Accession No. NC_000001, nucleotides 18830087-18935219), PTEN (10q23.3; e.g., GENBANK™ Accession No. NC_000010, nucleotides 89613175-89718512), AKT2 (19q13.1-q13.2; e.g., GENBANK™ Accession No. NC_000019, complement, nucleotides 45428064-45483105), MYCL1 (1p34.2; e.g., GENBANK™ Accession No. NC_000001, complement, nucleotides 40133685-40140274), REL (2p13-p12; e.g., GENBANK™ Accession No. NC_000002, nucleotides 60962256-61003682) and CSF1R (5q33-q35; e.g., GENBANK™ Accession No. NC_000005, complement, nucleotides 149413051-149473128). The target detected by GEAR can include a region of the respective human chromosome containing at least a portion of any one (or more, as applicable) of the foregoing genes.

B. Primers

Primers suitable for use in the disclosed methods are described herein. The primers disclosed herein are at least about 10 nucleotides in length, such as at least about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or about 50 nucleotides in length. In some embodiments, the primers are about 10-50 nucleotides in length, such as, 12-15, 12-20, 12-25, 12-30, 12-35, 12-40, 12-45, 12-50, 14-15, 14-16, 14-18, 14-20, 14-25, 14-30, 15-16, 15-18, 15-20, 15-25, 15-30, 15-35, 15-40, 15-45, 15-50, 16-17, 16-18, 16-20, 16-22, 16-25, 16-30, 16-40, 16-50, 17-18, 17-20, 17-22, 17-25, 17-30, 18-19, 18-20, 18-22, 18-25, 18-30, 19-20, 19-22, 19-25, 19-30, 20-21, 20-22, 20-25, 20-30, 20-35, 20-40, 20-45, 20-50, 21-22, 21-25, 21-30, 22-25, 22-30, 22-40, 22-50, 23-24, 23-25, 23-30, 24-25, 24-30, 25-30, 25-35, 25-40 or 25-45, 25-50 nucleotides in length. In additional embodiments, primers are of a maximum length, for example no more than 15, 25, 25, 40, 50, 75 or 100 nucleotides in length.

In several embodiments, the methods for amplification and/or identification of target nucleic acid molecules include use of a forward turn-back primer and a reverse turn-back primer, for example as referred to as FT and BT herein. The forward turn-back primer includes a first segment and a second segment. The first segment is 5' to the second segment. The first segment of the forward turn-back primer includes a nucleotide sequence that hybridizes to the center region of the target nucleic acid molecule and the second segment of the forward turn-back primer includes a nucleotide sequence that hybridizes to the complement of the 5'-end region of the target nucleic acid molecule. The reverse turn-back primer also includes a first segment and a second segment. The first segment is 5' to the second segment. The first segment of the reverse turn-back primer includes a nucleotide sequence that hybridizes to the complement of the center region and the second segment of the reverse turn-back primer includes a nucleotide sequence that hybridizes to the 3'-end region.

In additional embodiments, the methods further utilize an internal forward primer and an internal reverse primer, referred to as IF and IR herein. The internal forward primer is complementary to the internal forward region of the target nucleic acid molecule and the internal reverse primer is complementary to the internal reverse region of the target nucleic acid molecule.

In some embodiments, the first segment of the forward turn-back primer, the second segment of the forward turn-back primer, the first segment of the reverse turn-back primer, the second segment of the reverse turn-back primer, or two or more thereof, is least about 10 nucleotides in length, such as at least about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or about 50 nucleotides in length. In some embodiments, the first segment of the forward turn-back primer, the second segment of the forward turn-back primer, the first segment of the reverse turn-back primer, the second segment of the reverse turn-back primer, or two or more thereof is about 10-50 nucleotides in length, such as, 12-15, 12-20, 12-25, 12-30, 12-35, 12-40, 12-45, 12-50, 14-15, 14-16, 14-18, 14-20, 14-25, 14-30, 15-16, 15-18, 15-20, 15-25, 15-30, 15-35, 15-40, 15-45, 15-50, 16-17, 16-18, 16-20, 16-22, 16-25, 16-30, 16-40, 16-50, 17-18, 17-20, 17-22, 17-25, 17-30, 18-19, 18-20, 18-22, 18-25, 18-30, 19-20, 19-22, 19-25, 19-30, 20-21, 20-22, 20-25, 20-30, 20-35, 20-40, 20-45, 20-50, 21-22, 21-25, 21-30, 22-25, 22-30, 22-40, 22-50, 23-24, 23-25, 23-30, 24-25, 24-30, 25-30, 25-35, 25-40 or 25-45, 25-50 nucleotides in length. In additional embodiments, the first segment of the forward turn-back primer, the second segment of the forward turn-back primer, the first segment of the reverse turn-back primer, the second segment of the reverse turn-back primer, or two or more thereof is of a maximum length, for example no more than 15, 25, 25, 40 or 50 nucleotides in length.

In several embodiments, the first segment of the forward turn-back primer includes the nucleotide sequence having at least 90% (such as at least 91%, 92%, 93%, 94%, 95%, 96%, 97%, 98%, 99% or 100%) sequence identity to the complement of the center region of the target nucleic acid molecule and the second segment of the forward turn-back primer includes a nucleotide sequence having at least 90% (such as at least 91%, 92%, 93%, 94%, 95%, 96%, 97%, 98%, 99% or 100%) sequence identity to the 5'-end region of the target nucleic acid molecule. In one example, the first segment of the forward turn-back primer can be substantially identical to the nucleotide sequence of complement of center region (Tc), such as having no more than 5 nucleotide substitutions, deletions and/or insertions, such as 5, 4, 3, 2 or 1, such as 1-5, 1-4, 1-3, 2-4, or 1-2 nucleotide substitutions, deletions and/or insertions as compared to nucleotide sequence of Tc.

In one example, the second segment of the forward turn-back primer can be substantially identical to the nucleotide sequence of the 5'-end region of the target nucleic acid molecule (F), such as having no more than 5 nucleotide substitutions, deletions and/or insertions, such as 5, 4, 3, 2 or 1, such as 1-5, 1-4, 1-3, 2-4, or 1-2 nucleotide substitutions, deletions and/or insertions as compared to nucleotide sequence of F.

In additional embodiments, the first segment of the reverse turn-back primer includes a nucleotide sequence having at least 90% (such as at least 91%, 92%, 93%, 94%, 95%, 96%, 97%, 98%, 99% or 100%) sequence identity to the center region of the target nucleic acid molecule and the second segment of the reverse turn-back primer includes a nucleotide sequence having at least 90% (such as at least 91%, 92%, 93%, 94%, 95%, 96%, 97%, 98%, 99% or 100%) sequence identity to the 3'-end region of the target nucleic acid molecule. In one example, the first segment of the reverse turn-back primer can be substantially identical to the nucleotide sequence of the center region of the target nucleic acid molecule (T), such as having no more than 5 nucleotide substitutions, deletions and/or insertions, such as 5, 4, 3, 2 or 1, such as 1-5, 1-4, 1-3, 2-4, or 1-2 nucleotide substitutions, deletions and/or insertions as compared to nucleotide sequence of T.

In additional embodiments, the internal forward primer includes the nucleotide sequence having at least 90% (such as at least 91%, 92%, 93%, 94%, 95%, 96%, 97%, 98%, 99% or 100%) sequence identity to the complement of the internal reverse region. In further embodiments, the internal forward primer includes the nucleotide sequence having at least 90% (such as at least 91%, 92%, 93%, 94%, 95%, 96%, 97%, 98%, 99% or 100%) sequence identity to the internal forward region. In one example, the second segment of the reverse turn-back primer can be substantially identical to the nucleotide sequence of complement of 3' region (Bc), such as having no more than 5 nucleotide substitutions, deletions and/or insertions, such as 5, 4, 3, 2 or 1, such as 1-5, 1-4, 1-3, 2-4, or 1-2 nucleotide substitutions, deletions and/or insertions as compared to nucleotide sequence of Bc.

In some embodiments, the methods are used to amplify or identify an *Escherichia coli* nucleic acid molecule, such as the target nucleic acid molecule including the nucleotide sequence set forth as SEQ ID NO: 1. In some such embodiments, the GEAR assay includes use of a forward turn-back primer and a reverse turn-back primer. The forward turn-back primer includes a first segment that hybridizes to nucleotides 46-64 of SEQ ID NO: 1 and a second segment including a nucleotide sequence that hybridizes to the complement of nucleotides 1-22 of SEQ ID NO: 1 (for example a primer that is least 90% identical, such as 91%, 92%, 93%, 94%, 95%, 96%, 97%, 98%, 99%, or 100% identical, to the nucleotide sequence set forth as SEQ ID NO: 2). The reverse turn-back primer includes a first segment that hybridizes to the complement of nucleotides 46-64 of SEQ ID NO: 1 and a second segment including a nucleotide sequence that hybridizes to nucleotides 89-108 of SEQ ID NO: 1 (for example a primer that is least 90% identical, such as 91%, 92%, 93%, 94%, 95%, 96%, 97%, 98%, 99%, or 100% identical, to the nucleotide sequence set forth as SEQ ID NO: 3). In additional embodiments, the GEAR assay further include the use of an internal forward primer and an internal reverse primer. In some examples, the internal forward primer including a nucleotide sequence that hybridizes to the complement of nucleotides 68-85 of SEQ ID NO: 1 (for example a primer that is least 90% identical, such as 91%, 92%, 93%, 94%, 95%, 96%, 97%, 98%, 99%, or 100% identical, to the nucleotide sequence set forth as SEQ ID NO: 5). In additional examples, the internal reverse primer including a nucleotide sequence that hybridizes to nucleotides 24-45 of SEQ ID NO: 1 (for example a primer that is least 90% identical, such as 91%, 92%, 93%, 94%, 95%, 96%, 97%, 98%, 99%, or 100% identical, to the nucleotide sequence set forth as SEQ ID NO: 4).

In additional embodiments, the GEAR assay is used to amplify or identify a *Vibrio cholerae* nucleic acid molecule, such as the target nucleic acid molecule including the nucleotide sequence set forth as nucleotides 193-319 of SEQ ID NO: 12. In some such embodiments, the forward turn-back primer includes a first segment that hybridizes to nucleotides 245-267 of SEQ ID NO: 12 and a second segment including a nucleotide sequence that hybridizes to the complement of nucleotides 193-218 of SEQ ID NO: 12 (for example a primer that is least 90% identical, such as 91%, 92%, 93%, 94%, 95%, 96%, 97%, 98%, 99%, or 100% identical, to the nucleotide sequence set forth as SEQ ID NO: 19). The reverse turn-back primer includes a first segment that hybridizes to the complement of nucleotides 245-267 of SEQ ID NO: 12 and a second segment including a nucleotide sequence that hybridizes to nucleotides 292-319 of SEQ ID NO: 12 (for example a primer that is least 90% identical, such as 91%, 92%, 93%, 94%, 95%, 96%, 97%, 98%, 99%, or 100% identical, to the nucleotide sequence set forth as SEQ ID NO: 20). In additional embodiments, the GEAR assay further includes the use of an internal forward primer and an internal reverse primer. In some examples, the internal forward primer including a nucleotide sequence that hybridizes to the complement of nucleotides 269-290 of SEQ ID NO: 12 (for example a primer that is least 90% identical, such as 91%, 92%, 93%, 94%, 95%, 96%, 97%, 98%, 99%, or 100% identical, to the nucleotide sequence set forth as SEQ ID NO: 22). In additional examples, the internal reverse primer including a nucleotide sequence that hybridizes to nucleotides 220-243 of SEQ ID NO: 12 (for example a primer that is least 90% identical, such as 91%, 92%, 93%, 94%, 95%, 96%, 97%, 98%, 99%, or 100% identical, to the nucleotide sequence set forth as SEQ ID NO: 21).

In additional embodiments, the GEAR assay is used to amplify or identify a *Homo sapiens* nucleic acid molecule, such as the target nucleic acid molecule including the nucleotide sequence set forth as nucleotides 558-659 of SEQ ID NO: 31. In some such embodiments, the forward turn-back primer includes a first segment that hybridizes to nucleotides 558-575 of SEQ ID NO: 31 and a second segment including a nucleotide sequence that hybridizes to the complement of nucleotides 596-622 of SEQ ID NO: 31 (for example a primer that is least 90% identical, such as 91%, 92%, 93%, 94%, 95%, 96%, 97%, 98%, 99%, or 100% identical, to the nucleotide sequence set forth as SEQ ID NO: 23). The reverse turn-back primer includes a first segment that hybridizes to the complement of nucleotides 642-659 of SEQ ID NO: 31 and a second segment including a nucleotide sequence that hybridizes to nucleotides 596-622 of SEQ ID NO: 31 (for example a primer that is least 90% identical, such as 91%, 92%, 93%, 94%, 95%, 96%, 97%, 98%, 99%, or 100% identical, to the nucleotide sequence set forth as SEQ ID NO: 24). In additional embodiments, the GEAR assay further includes the use of an internal forward primer and an internal reverse primer. In some examples, the internal forward primer including a nucleotide sequence that hybridizes to the complement of nucleotides 624-640 of SEQ ID NO: 31 (for example a primer that is least 90% identical, such as 91%, 92%, 93%, 94%, 95%, 96%, 97%, 98%, 99%, or 100% identical, to the nucleotide sequence set forth as SEQ ID NO: 26). In additional examples, the internal reverse primer including a nucleotide sequence that hybridizes to nucleotides 578-594 of SEQ ID NO: 31 (for example a primer that is least 90% identical, such as 91%, 92%, 93%, 94%, 95%, 96%, 97%, 98%, 99%, or 100% identical, to the nucleotide sequence set forth as SEQ ID NO: 25).

In additional embodiments, the GEAR assay is used to amplify or identify a Enterobacteria phage MS2 nucleic acid molecule, such as the target nucleic acid molecule including the nucleotide sequence set forth as nucleotides 937-1052 of SEQ ID NO: 32. In some such embodiments, the forward turn-back primer includes a first segment that hybridizes to nucleotides 937-956 of SEQ ID NO: 32 and a second segment including a nucleotide sequence that hybridizes to the complement of nucleotides 982-1004 of SEQ ID NO: 32 (for example a primer that is least 90% identical, such as 91%, 92%, 93%, 94%, 95%, 96%, 97%, 98%, 99%, or 100% identical, to the nucleotide sequence set forth as SEQ ID NO: 27). The reverse turn-back primer includes a first segment that hybridizes to the complement of nucleotides 1032-1052 of SEQ ID NO: 32 and a second segment including a nucleotide sequence that hybridizes to nucleotides 982-1004 of SEQ ID NO: 32 (for example a primer that is least 90% identical, such as 91%, 92%, 93%, 94%, 95%, 96%, 97%, 98%, 99%, or 100% identical, to the nucleotide sequence set forth as SEQ ID NO: 28). In additional embodiments, the GEAR assay further includes the use of an internal forward primer and an internal reverse primer. In some examples, the internal forward primer including a nucleotide sequence that hybridizes to the complement of nucleotides 1009-1029 of SEQ ID NO: 32 (for example a primer that is least 90% identical, such as 91%, 92%, 93%, 94%, 95%, 96%, 97%, 98%, 99%, or 100% identical, to the nucleotide sequence set forth as SEQ ID NO: 30). In additional examples, the internal reverse primer including a nucleotide sequence that hybridizes to nucleotides 959-980 of SEQ ID NO: 32 (for example a primer that is least 90% identical, such as 91%, 92%, 93%, 94%, 95%, 96%, 97%, 98%, 99%, or 100% identical, to the nucleotide sequence set forth as SEQ ID NO: 29).

Those versed in the art will recognize that specification of a single-stranded DNA sequence implies the utility of the complementary DNA sequence, as well as the two equivalent RNA sequences, for amplifying and identifying nucleic acid molecules. Furthermore, sequences incorporating modifications of any of the moieties including the nucleic acid (such as the sugar or the backbone) are functional equivalents of the sequence. These sequences (or subsequences thereof) can themselves serve as probes or primers.

In some embodiments, the primers for use in GEAR assay are designed based on the known sequences of primer/probe combinations for use in TaqMan real-time PCR assays. TaqMan real-time PCR is considered as the gold standard in quantitative diagnosis using amplification assays. TaqMan assays utilize a forward and revise primer for PCR amplification of a target nucleic acid molecule, and a specific probe to detect the amplified target nucleic acid molecule. Most of the TaqMan assay primers (forward and reverse) are designed in the range of 60° C. to 65° C. and TaqMan probe is designed in the range of 65° C. to 70° C. It is possible to convert known TaqMan primer/probe combinations into FT and BT primers for the GEAR assay. The sequence of the forward and reverse primers for the TaqMan assay can be used as the sequence of segments of the FT and BT primers that anneal to the 5' end region and the 3'end region for the GEAR assay. The sequence of the probe for the TaqMan assay can be used as the sequence of the segment of the FT and BT primers that anneals to the center region of the target nucleic acid molecule for the GEAR assay. In some embodiments, additional primers IR and IF can be manually selected between the regions of forward and probe region for the primer IR and between the regions of reverse and probe region for the primer IF to increase the speed and/or efficiency of the GEAR assay.

Primers are typically designed so that all of the primers participating in a particular reaction have melting temperatures that are within at least five degrees Celsius, and more typically within two degrees Celsius of each other. Primer concentration should be sufficient to bind to the amount of target sequences that are amplified so as to provide an accurate assessment of the quantity of amplified sequence. Those of skill in the art will recognize that the amount of concentration of primer will vary according to the binding affinity of the primers as well as the quantity of sequence to be bound. Typical primer concentrations will range from 0.01 µM to 2.0 µM. In one embodiment including use of a forward turn-back primer, reverse turn-back primer, internal forward primer and internal reverse primer as described herein, the concentration of the forward turn-back primer is 1 µM, the concentration of the reverse turn-back primer is 1 µM, the concentration of the internal forward primer is 0.1 µM and the concentration of the forward turn-back primer is 1 µM. In several embodiments, the first segment of the forward turnback primer includes a Tm of from 58-64° C., the second segment of the forward turnback primer includes a Tm of from about 60-70° C., the first segment of the reverse turnback primer includes a Tm of from 58-64° C., the second segment of the reverse turnback primer includes a Tm of from about 60-70° C., the internal forward primer includes a Tm of about 58-63° C. and the internal reverse primer includes a Tm of about 58-63° C.

C. Samples

Appropriate samples include any conventional environmental or biological samples, including clinical samples obtained from a human or veterinary subject. Suitable samples include all biological samples useful for detection of bacterial infection in subjects, including, but not limited to, cells, tissues (for example, lung, liver, and kidney), autopsy samples, bone marrow aspirates, bodily fluids (for example, blood, serum, urine, cerebrospinal fluid, middle ear fluids, bronchoalveolar lavage, tracheal aspirates, sputum, nasopharyngeal aspirates, oropharyngeal aspirates, or saliva), eye swabs, cervical swabs, vaginal swabs, rectal swabs, stool, and stool suspensions. Standard techniques for acquisition of such samples are available. See for example, Schluger et al., *J. Exp. Med.* 176:1327-1333, 1992; Bigby et al., *Am. Rev. Respir. Dis.* 133:515-518, 1986; Kovacs et al., *N. Engl. J. Med.* 318:589-593, 1988; and Ognibene et al., *Am. Rev. Respir. Dis.* 129:929-932, 1984.

The disclosure also contemplates other sample types, such as environmental samples. For example, the sample can be one that includes soil, water, air, or one obtained by swabbing a surface (such as a surface found in a medical setting, laboratory setting, or home or office). In one example the sample is a plant or portion thereof, such as a leaf, stem, or root.

One of ordinary skill in the art will know suitable methods for extracting nucleic acids such as RNA and/or DNA from a sample; such methods will depend upon, for example, the type of sample in which the nucleic acid is found. Nucleic acids can be extracted using standard methods. For instance, rapid nucleic acid preparation can be performed using a commercially available kit (such as kits and/or instruments from Qiagen (such as DNEasy® or RNEasy® kits), Roche Applied Science (such as MagNA Pure kits and instruments), Thermo Scientific (KingFisher mL), bioMérieux (Nuclisens® NASBA Diagnostics), or Epicentre (Masterpure™ kits)). In other examples, the nucleic acids may be extracted using guanidinium isothiocyanate, such as single-step isolation by acid guanidinium isothiocyanate-phenol-chloroform extraction (Chomczynski et al. *Anal. Biochem.* 162:156-159, 1987). The sample can be used directly or can be processed, such as by adding solvents, preservatives, buffers, or other compounds or substances. In still other examples, no extraction procedure is performed prior to the amplification reaction.

D. Detection and Identification

In several embodiments, methods for identifying the presence of a target nucleic acid molecule (such as one found in a target organism or cell) in a sample are provided. The methods include amplifying a target nucleic acid molecule using the provided GEAR assay and detecting the amplified target nucleic acid molecule (for example determining if the target nucleic acid molecule is present). Detecting the target nucleic acid molecule identifies the presence of the target nucleic acid molecule in the sample. In contrast, if the target nucleic acid molecule is not detected, this indicates the absence of the target nucleic acid molecule in the sample.

In some examples, the disclosed methods can predict with a sensitivity of at least 90% and a specificity of at least 90% for presence of a the target nucleic acid molecule in a sample, such as a sensitivity of at least 91%, 92%, 93%, 94%, 95%, 96%, 97%, 98%, 99%, or even 100% and a specificity of at least of at least 91%, 92%, 93%, 94%, 95%, 96%, 97%, 98%, 99%, or even 100%. For example, in some examples, the disclosed methods can predict with a sensitivity of at least 90% and a specificity of at least 90% for presence of a *Escherichia coli* nucleic acid, such as a sensitivity of at least 91%, 92%, 93%, 94%, 95%, 96%, 97%, 98%, 99%, or even 100% and a specificity of at least of at least 91%, 92%, 93%, 94%, 95%, 96%, 97%, 98%, 99%, or even 100%. In still further examples, the disclosed methods can predict with a sensitivity of at least 90% and a specificity of at least 90% for presence of a *Vibrio cholerae* nucleic acid, such as a sensitivity of at least 91%, 92%, 93%, 94%, 95%, 96%, 97%, 98%, 99%, or even 100% and a specificity of at least of at least 91%, 92%, 93%, 94%, 95%, 96%, 97%, 98%, 99%, or even 100%. In additional examples, the disclosed methods can predict with a sensitivity of at least 90% and a specificity of at least 90% for presence of a *Homo Sapiens* nucleic acid, such as a sensitivity of at least 91%, 92%, 93%, 94%, 95%, 96%, 97%, 98%, 99%, or even 100% and a specificity of at least of at least 91%, 92%, 93%, 94%, 95%, 96%, 97%, 98%, 99%, or even 100%.

In still further examples, the disclosed methods can predict with a sensitivity of at least 90% and a specificity of at least 90% for presence of a viral nucleic acid, such as a Enterobacteria phage MS2 nucleic acid, such as a sensitivity of at least 91%, 92%, 93%, 94%, 95%, 96%, 97%, 98%, 99%, or even 100% and a specificity of at least of at least 91%, 92%, 93%, 94%, 95%, 96%, 97%, 98%, 99%, or even 100%.

Several embodiments include detecting the amplified target nucleic acid molecule. In some embodiments, the amplified products are detected with by photometry for turbidity caused by increasing quantity of magnesium pyrophosphate in solution (see, e.g., Mori et al., BBRC, 289:150-154, 2001). In additional examples in-tube detection of amplification is possible using manganese loaded calcein which fluoresces upon complexation of manganes by pyrophosphate during in vitro DNA synthesis (Tomita et al., Nat. Protoc., 3:877-82, 2008).

In certain embodiments, the amplified products are directly visualized with detectable label such as a fluorescent DNA-binding dye. In one embodiment the amplified products are quantified using an intercalating dye, including but not limited to SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin. For example, a DNA binding dye such as SYBR green binds double stranded DNA and an increase in fluorescence intensity can be measured. For example, the fluorescent dsDNA dye can be added to the buffer used for an amplification reaction. For example, the levels of fluorescence are measured with a detector, such as a camera, at regular time intervals (such as once a minute) for the duration of the amplification assay. The dye fluoresces much more strongly when bound to double stranded nucleic acid molecules (e.g., amplified product). Because the amount of the dye intercalated into the double-stranded nucleic acid molecules is typically proportional to the amount of the amplified nucleic acid products, the amount of amplified nucleic acid can be quantified by detecting the fluorescence of the intercalated dye using detection instruments known in the art. When referenced to a standard dilution, the double stranded nucleic acid molecule concentration in the amplification reaction can be determined.

In addition to various kinds of fluorescent nucleic acid-binding dye, other luminescent labels such as sequence specific oligonucleotide probes can be employed in the amplification reaction to facilitate the detection and quantification of the amplified product. Probe based quantitative amplification relies on the sequence-specific detection of a desired amplified product. Unlike the dye-based quantitative methods, it utilizes target-specific probe labeled with a detectable marker such as a base-linked or terminally-linked fluorophore and quencher. Such markers are known to the person of ordinary skill in the art and described herein. For detection using oligonucleotide probes, the reaction is prepared as usual for isothermal amplification conditions, with the addition of the sequence specific labeled oligonucleotide probe.

In one embodiment, the fluorescently-labeled probes (such as probes disclosed herein) rely upon fluorescence resonance energy transfer (FRET), or in a change in the fluorescence emission wavelength of a sample, as a method to detect hybridization of a probe to the amplified target nucleic acid in real-time. For example, FRET that occurs between fluorogenic labels on different probes (for example, using HybProbes) or between a donor fluorophore and an acceptor or quencher fluorophore on the same probe (for example, using a molecular beacon or a TaqMan® probe) can identify a probe that specifically hybridizes to the nucleic acid sequence of interest. When quenching occurs, there is little or no detection of fluorescence and when the quencher is separated from the fluorophore there is a shift in fluorescence intensity. Exemplary FRET pairs include FAM as a suitable donor fluorophore for use with JOE, TAMRA, and ROX as acceptor fluorophores; or 3-(ϵ-carboxy-pentyl)-3'-ethyl-5,5'-dimethyloxacarbocyanine (CYA) as a donor fluorophore for rhodamine derivatives (such as R6G, TAMRA, and ROX) as acceptor fluorophores.

In some embodiments, the isothermal amplification reaction is monitored in real-time. Real-time amplification methods include monitoring of a signal during the amplification reaction (such as emission of fluorescence) as an indicator of amplicon production, as opposed to endpoint detection. The real-time progress of the reaction can be viewed in some systems. Typically, real-time amplification uses the detection of a fluorescent reporter. Typically, the fluorescent reporter's signal increases in direct proportion to the amount of amplified product in a reaction. By recording the amount of fluorescence emission during the amplification reaction, it is possible to monitor the amplification reaction during exponential phase where the first significant increase in the amount of amplified product correlates to the initial amount of target template. The higher the starting copy number of the nucleic acid target, the sooner a significant increase in fluorescence is observed. Thus, the procedure follows the general pattern of polymerase chain reaction, but the nucleic acid molecule is quantified after each round of amplification. In several embodiments the amplified nucleic acid molecule is quantified by the use of fluorescent dye that intercalates with double-strand nucleic acid molecules. In other embodiments amplified nucleic acid molecule is quantified by use of oligonucleotide probes labeled with a reporter fluorophore.

In one non-limiting embodiment, the amplification and/or identification reaction method is carried out under isothermal condition at 60° C. for 90 minutes in the presence of an intercalating dye (SYTO 9) and fluorescence signal acquired every minute using an ABI 7500 Real-Time PCR System™ (Applied Biosystems, Foster City, Calif.).

The disclosed GEAR assay can be performed in the presence of malachite green (MG), which permits detection of the resulting amplicons. For example, the amplification reaction, which includes nucleic acids from the test sample, can include MG. This is a colored solution (e.g., blue/green solution), which is visibly detectable with the naked eye. After performing the GEAR assay, the amplified target nucleic acid molecule is detected, wherein detecting a visible color of the solution indicates the target nucleic acid molecule was present in the sample and amplified, while detecting a an absence of visible color of the solution (e.g., the solution is colorless) indicates the target nucleic acid molecule was not present in the sample and not amplified.

III. Differences Between GEAR and Loop Mediated Isothermal Amplification (LAMP)

The LAMP assay is an isothermal amplification method that relies on an auto-cycling strand displacement DNA synthesis that is performed by a polymerase with high strand displacement activity, an inner turn-back primer pair, and an outer pair of strand displacement primers to amplify target DNA (see Notami et al., *Nucl. Acid. Res.*, 28:e63, 2000 and U.S. Pat. No. 8,017,357). The GEAR assay differs from the LAMP assay by several distinct features. First, GEAR assays use turn-back primers (FT and BT) targeting three nucleic acid regions, whereas LAMP assays use turn-back primers (FIP and BIP, discussed below) targeting four regions on the target gene. Second, primer design for the GEAR technique differs from the LAMP technique in that the 5' ends of the FT and BT primers are complementary, whereas the corresponding turn-back primers of the LAMP assay (FIP and BIP) do not form a complementary structure at the 5' end. Third, GEAR assays do not require outer strand displacement primers for an efficient assay, whereas LAMP assays require two outer strand displacement primers (F3 and B3, discussed below). Additionally, as described above, the primers for the GEAR assays can be conveniently designed based on the known sequences of primer/probe combinations for TaqMan assays, whereas primers for LAMP assays cannot be designed using this information.

The inner primers for the LAMP assay are called the forward inner primer (FIP) and the backward inner primer (BIP), respectively, and each contains two distinct sequences corresponding to the sense and antisense sequences of the target DNA. With reference to FIG. 3, the nucleotide sequences inside both ends of the target DNA for amplification are designated F2c and B2, respectively. Two inner sequences from the ends of F2c and B2 are designated F1c and B1 and two sequences outside the ends of F2c and B2 are designated F3c and B3. Given this structure, the sequences of FIP and BIP are designed as follows: FIP includes the sequence of F1c, a spacer and the sequence (F2) complementary to F2c. BIP contains the sequence (B1c) complementary to B1, a spacer and the sequence of B2. The two outer strand displacement primers include the sequence of B3 and the sequence (F3) complementary to F3c, respectively. The standard LAMP reaction is initiated by addition of the Bst DNA polymerase (large fragment) and the four primers (targeting six regions of the target DNA). A modification the LAMP assay has also been developed, which includes use of two additional primers, targeting two additional target regions (accelerated LAMP; Nagamine and Notomi, *Mol. Cell. Probes*, 16: 223-229, 2002).

The mechanism and reaction steps of LAMP are illustrated in FIG. 3. The FIP primer hybridizes to F2c in the target DNA and initiates complementary strand synthesis (FIG. 3). Outer strand displacement primer F3 hybridizes to F3c in the target DNA and initiates strand displacement DNA synthesis, releasing a FIP-linked complementary strand, which can form a looped out structure at one end (structure 4). This single-stranded DNA serves as template for BIP-initiated DNA synthesis and subsequent B3-primed strand displacement DNA synthesis, leading to the production of a dumb-bell form DNA (structure 6), which is quickly converted to a stem-loop DNA by self-primed DNA synthesis (structure 7). This stem-loop DNA then serves as the starting material for LAMP cycling, the second stage of the LAMP reaction, wherein the reaction cycles through several amplification product structures (structures 7-10). The final products are a mixture of stem-loop DNAs with various stem lengths and cauliflower-like structures with multiple loops formed by annealing between alternately inverted repeats of the target sequence in the same strand (FIG. 3, structures 16-18).

Thus, the GEAR assay utilizes two primers targeting three target regions or four primers targeting five target regions. In contrast, the LAMP assay, which requires four primers targeting six regions of the target DNA (standard LAMP) or six primers to target eight regions (accelerated LAMP) for efficient amplification.

IV. Compositions

The primers disclosed herein can be included in a composition for use for the amplification and/or identification of target nucleic acid molecules in a sample. For example, the composition can include a forward turn-back primer and a reverse turn-back primer for use in the methods described herein. In additional embodiments, the composition can further include an internal forward primer and an internal reverse primer for use in the methods of amplifying and/or identifying targets nucleic acid molecules as described herein.

In some embodiments, the composition includes primers for amplifying an *E. coli* nucleic acid molecule, such as the target nucleic acid molecule including the nucleotide sequence set forth as SEQ ID NO: 1. In some such embodiments, the composition includes a forward turn-back primer and a reverse turn-back primer, wherein the forward turn-back primer includes a first segment that hybridizes to nucleotides 46-64 of SEQ ID NO: 1 and a second segment that hybridizes under very high stringency conditions to the complement of nucleotides 1-22 of SEQ ID NO: 1 (for example a primer that is least 90% identical, such as 91%, 92%, 93%, 94%, 95%, 96%, 97%, 98%, 99%, or 100% identical, to the nucleotide sequence set forth as SEQ ID NO: 2), and the reverse turn-back primer includes a first segment that hybridizes to the complement of nucleotides 46-64 of SEQ ID NO: 1 and a second segment including a nucleotide sequence that hybridizes to nucleotides 89-108 of SEQ ID NO: 1 (for example a primer that is least 90% identical, such as 91%, 92%, 93%, 94%, 95%, 96%, 97%, 98%, 99%, or 100% identical, to the nucleotide sequence set forth as SEQ ID NO: 3). In additional embodiments, the composition further includes an internal forward primer and an internal reverse primer, wherein the internal forward primer includes a nucleotide sequence that hybridizes to the complement of nucleotides 68-85 of SEQ ID NO: 1 (for example a primer that is least 90% identical, such as 91%, 92%, 93%, 94%, 95%, 96%, 97%, 98%, 99%, or 100% identical, to the nucleotide sequence set forth as SEQ ID NO: 5) and the internal reverse primer includes a nucleotide sequence that hybridizes to nucleotides 24-45 of SEQ ID NO: 1 (for example a primer that is least 90% identical, such as 91%, 92%, 93%, 94%, 95%, 96%, 97%, 98%, 99%, or 100% identical, to the nucleotide sequence set forth as SEQ ID NO: 4).

In further embodiments, the composition includes primers for amplifying an *Escherichia coli* nucleic acid molecule, such as the target nucleic acid molecule including the nucleotide sequence set forth as SEQ ID NO: 1. In some such embodiments, the composition includes a forward turn-back primer and a reverse turn-back primer, wherein the forward turn-back primer consists of the nucleotide sequence set forth as SEQ ID NO: 2, and the reverse turn-back primer consists of the nucleotide sequence set forth as SEQ ID NO: 3. In additional embodiments, the composition further includes an internal forward primer and an internal reverse primer, wherein the internal forward primer consists of the nucleotide sequence set forth as SEQ ID NO: 5 and the internal reverse primer consists of the nucleotide sequence set forth as SEQ ID NO: 4.

In some embodiments, the composition includes primers for amplifying a *Vibrio cholerae* nucleic acid molecule, such as the target nucleic acid molecule including the nucleotide sequence set forth as nucleotides 193-319 of SEQ ID NO: 12. For example, in some embodiments, the composition includes a forward turn-back primer and a reverse turn-back primer, wherein the forward turn-back primer includes a first segment that hybridizes to nucleotides 245-267 of SEQ ID NO: 12 and a second segment including a nucleotide sequence that hybridizes to the complement of nucleotides 193-218 of SEQ ID NO: 12 (for example a primer that is least 90% identical, such as 91%, 92%, 93%, 94%, 95%, 96%, 97%, 98%, 99%, or 100% identical, to the nucleotide sequence set forth as SEQ ID NO: 19), and the reverse turn-back primer includes a first segment that hybridizes to the complement of nucleotides 245-267 of SEQ ID NO: 12 and a second segment including a nucleotide sequence that hybridizes to nucleotides 292-319 of SEQ ID NO: 12 (for example a primer that is least 90% identical, such as 91%, 92%, 93%, 94%, 95%, 96%, 97%, 98%, 99%, or 100% identical, to the nucleotide sequence set forth as SEQ ID NO: 20). In additional embodiments, the composition further includes an internal forward primer and an internal reverse primer, wherein the internal forward primer includes a nucleotide sequence that hybridizes to the complement of nucleotides 269-290 of SEQ ID NO: 12 (for example a primer that is least 90% identical, such as 91%, 92%, 93%, 94%, 95%, 96%, 97%, 98%, 99%, or 100% identical, to the nucleotide sequence set forth as SEQ ID NO: 22) and the internal reverse primer includes a nucleotide sequence that hybridizes to nucleotides 220-243 of SEQ ID NO: 12 (for example a primer that is least 90% identical, such as 91%, 92%, 93%, 94%, 95%, 96%, 97%, 98%, 99%, or 100% identical, to the nucleotide sequence set forth as SEQ ID NO: 21).

In some embodiments, the composition includes primers for amplifying a *Vibrio cholerae* nucleic acid molecule, such as the target nucleic acid molecule including the nucleotide sequence set forth as nucleotides 193-319 of SEQ ID NO: 12. For example, in some embodiments, the composition includes a forward turn-back primer and a reverse turn-back primer, wherein the forward turn-back primer consists of the nucleotide sequence set forth as SEQ ID NO: 19, and the reverse turn-back primer consists of the nucleotide sequence set forth as SEQ ID NO: 20. In additional embodiments, the composition further includes an internal forward primer and an internal reverse primer, wherein the internal forward primer consists of the nucleotide sequence set forth as SEQ ID NO: 22 and the internal reverse primer consists of the nucleotide sequence set forth as SEQ ID NO: 21.

In some embodiments, the composition includes primers for amplifying a *Homo sapiens* nucleic acid molecule, such as the target nucleic acid molecule including the nucleotide sequence set forth as nucleotides 575-659 of SEQ ID NO: 31. For example, in some embodiments, the composition includes a forward turn-back primer and a reverse turn-back primer, wherein the forward turn-back primer includes a first segment that hybridizes to nucleotides 558-575 of SEQ ID NO: 31 and a second segment including a nucleotide sequence that hybridizes to the complement of nucleotides 596-622 of SEQ ID NO: 31 (for example a primer that is least 90% identical, such as 91%, 92%, 93%, 94%, 95%, 96%, 97%, 98%, 99%, or 100% identical, to the nucleotide sequence set forth as SEQ ID NO: 23), and the reverse turn-back primer includes a first segment that hybridizes to the complement of nucleotides 642-659 of SEQ ID NO: 31 and a second segment including a nucleotide sequence that hybridizes to nucleotides 596-622 of SEQ ID NO: 31 (for example a primer that is least 90% identical, such as 91%, 92%, 93%, 94%, 95%, 96%, 97%, 98%, 99%, or 100% identical, to the nucleotide sequence set forth as SEQ ID NO: 24). In additional embodiments, the composition further includes an internal forward primer and an internal reverse primer, wherein the internal forward primer includes a nucleotide sequence that hybridizes to the complement of nucleotides 624-640 of SEQ ID NO: 31 (for example a primer that is least 90% identical, such as 91%, 92%, 93%, 94%, 95%, 96%, 97%, 98%, 99%, or 100% identical, to the nucleotide sequence set forth as SEQ ID NO: 26) and the internal reverse primer includes a nucleotide sequence that hybridizes to nucleotides 578-594 of SEQ ID NO: 31 (for example a primer that is least 90% identical, such as 91%, 92%, 93%, 94%, 95%, 96%, 97%, 98%, 99%, or 100% identical, to the nucleotide sequence set forth as SEQ ID NO: 25).

In some embodiments, the composition includes primers for amplifying a *Homo sapiens* nucleic acid molecule, such as the target nucleic acid molecule including the nucleotide sequence set forth as nucleotides 575-659 of SEQ ID NO: 31. For example, in some embodiments, the composition includes a forward turn-back primer and a reverse turn-back primer, wherein the forward turn-back primer consists of the nucleotide sequence set forth as SEQ ID NO: 23, and the reverse turn-back primer consists of the nucleotide sequence set forth as SEQ ID NO: 24. In additional embodiments, the composition further includes an internal forward primer and an internal reverse primer, wherein the internal forward primer consists of the nucleotide sequence set forth as SEQ ID NO: 26 and the internal reverse primer consists of the nucleotide sequence set forth as SEQ ID NO: 25.

In some embodiments, the composition includes primers for amplifying a Enterobacteria phage MS2 nucleic acid molecule, such as the target nucleic acid molecule including the nucleotide sequence set forth as nucleotides 937-1052 of SEQ ID NO: 32. For example, in some embodiments, the composition includes a forward turn-back primer and a reverse turn-back primer, wherein the forward turn-back primer includes a first segment that hybridizes to nucleotides 937-956 of SEQ ID NO: 32 and a second segment including a nucleotide sequence that hybridizes to the complement of nucleotides 982-1004 of SEQ ID NO: 32 (for example a primer that is least 90% identical, such as 91%, 92%, 93%, 94%, 95%, 96%, 97%, 98%, 99%, or 100% identical, to the nucleotide sequence set forth as SEQ ID NO: 27), and the reverse turn-back primer includes a first segment that hybridizes to the complement of nucleotides 1032-1052 of SEQ ID NO: 32 and a second segment including a nucleotide sequence that hybridizes to nucleotides 984-1004 of SEQ ID NO: 32 (for example a primer that is least 90% identical, such as 91%, 92%, 93%, 94%, 95%, 96%, 97%, 98%, 99%, or 100% identical, to the nucleotide sequence set forth as SEQ ID NO: 28). In additional embodiments, the composition further includes an internal forward primer and an internal reverse primer, wherein the internal forward primer includes a nucleotide sequence that hybridizes to the complement of nucleotides 1009-1029 of SEQ ID NO: 32 (for example a primer that is least 90% identical, such as 91%, 92%, 93%, 94%, 95%, 96%, 97%, 98%, 99%, or 100% identical, to the nucleotide sequence set forth as SEQ ID NO: 30) and the internal reverse primer includes a nucleotide sequence that hybridizes to nucleotides 959-980 of SEQ ID NO: 32 (for example a primer that is least 90% identical, such as 91%, 92%, 93%, 94%, 95%, 96%, 97%, 98%, 99%, or 100% identical, to the nucleotide sequence set forth as SEQ ID NO: 29).

In some embodiments, the composition includes primers for amplifying a *Homo sapiens* nucleic acid molecule, such as the target nucleic acid molecule including the nucleotide sequence set forth as nucleotides 937-1052 of SEQ ID NO: 32. For example, in some embodiments, the composition includes a forward turn-back primer and a reverse turn-back primer, wherein the forward turn-back primer consists of the nucleotide sequence set forth as SEQ ID NO: 27, and the reverse turn-back primer consists of the nucleotide sequence set forth as SEQ ID NO: 28. In additional embodiments, the composition further includes an internal forward primer and an internal reverse primer, wherein the internal forward primer consists of the nucleotide sequence set forth as SEQ ID NO: 30 and the internal reverse primer consists of the nucleotide sequence set forth as SEQ ID NO: 29.

V. Use of Malachite Green to Detect Amplified Nucleic Acid Molecules

The inventors have found that malachite green can be used in nucleic acid amplification reactions to detect amplified nucleic acid molecules. MG can be used in any nucleic acid amplification method, such as a PCR reaction (including RT-PCR, real-time PCR, or real-time RT-PCR), or an isothermal amplification reaction, such as a LAMP assay, or a GEAR assay (as described herein).

MG is added to the starting mix for the amplification reaction. For example, MG can be added to an amplification mixture, such as one containing nucleic acid molecules from the test sample, dNTPs and a polymerase. Addition of MG to the mixture changes the color of the amplification reaction mixture from clear to blue/green. After the amplification, if the target nucleic acid molecule is successfully amplified (e.g., amplicons are generated), then the color of the solution of the amplification reaction remains blue/green. If the target nucleic acid molecule is not amplified, then the color of the solution changes to clear (colorless). In several embodiments, the concentration of malachite green in the amplification reaction is at least 0.0005%, such as least 0.001%, at least 0.002%, at least 0.003%, at least 0.004%, or at least 0.01%, such as from 0.001% to 0.01% or 0.001% to 0.006%, such as about 0.01%, 0.001%, 0.004%, or 0.0001% malachite green. The person of ordinary skill in the art is familiar with MG, and MG is commercially available, for example from Sigma —Aldrich Co. (St. Louis, Mo.; No. 38800). In several embodiments, MG is included in a kit for isothermal amplification of a nucleic acid molecule, such as a kit as described below.

VI. Kits

The primers and reagents disclosed herein can be supplied in the form of a kit for use in the amplification and/or identification of target nucleic acid molecules using a GEAR assay as provided herein. In such a kit, an appropriate amount of one or more of the primers as disclosed herein, for example SEQ ID NOs: 2-5 and 19-22) are provided in one or more containers. A nucleic acid primer may be provided suspended in an aqueous solution or as a freeze-dried or lyophilized powder, for instance. The container(s) in which the nucleic acid(s) are supplied can be any conventional container that is capable of holding the supplied form, for instance, microfuge tubes, ampoules, or bottles. The kits can include either labeled or unlabeled nucleic acid probes for use in detection of target nucleic acid molecules, such as $E.$ $coli$ or $V.$ $cholerae$ nucleic acids. One or more control primers for use in the amplification reactions also may be supplied in the kit.

In some examples, one or more sets of primers (such as the primers described above, such as the forward turn-back primer, the reverse turn-back primer, the internal forward primer and the internal reverse primer designed for isothermal amplification of a specific target nucleic acid molecule using the provided methods), may be provided in pre-measured single use amounts in individual, typically disposable, tubes or equivalent containers. With such an arrangement, the sample to be tested for the presence of the target nucleic acids can be added to the individual tube(s) and amplification carried out directly.

The amount of nucleic acid primer supplied in the kit can be any appropriate amount, and may depend on the target market to which the product is directed. For instance, if the kit is adapted for research or clinical use, the amount of each nucleic acid primer provided would likely be an amount sufficient to prime several amplification reactions. General guidelines for determining appropriate amounts may be found in Innis et al., Sambrook et al., and Ausubel et al.

In some embodiments, kits also may include the reagents necessary to carry out isothermal amplification reactions, including sample preparation reagents, appropriate buffers (such as polymerase buffer), salts (for example, magnesium chloride), deoxyribonucleotides (dNTPs), and strand displacement polymerases (such as Bst polymerase, large fragment).

In one example, the kit includes a tube or vial containing MG.

In other particular embodiments, the kit includes equipment, reagents, and instructions for extracting and/or purifying nucleic acid molecules from a sample.

The present disclosure is illustrated by the following non-limiting Examples.

EXAMPLES

Example 1

Isothermal Amplification of DNA Using Genome Exponential Amplification Reaction (GEAR) Assay This example illustrates a simple target-specific isothermal nucleic acid amplification technique, termed Genome Exponential Amplification Reaction (GEAR). The GEAR technique uses two or four primers: forward and reverse turn-back primers, and internal forward and internal reverse primers, which are internal to the turn-back primers on the target nucleic acid molecule. The outer forward and reverse turn-back primer sequences are complementary to each other at their 5'-end, whereas their 3'-end sequences are complementary to their respective target nucleic acid sequences. The inner pair of primers substantially increases the speed and sensitivity of the assay.

The GEAR assay was performed at a constant temperature 60° C. and monitored continuously in a real-time PCR instrument in the presence of an intercalating dye (SYTO 9). The assay enabled amplification of as few as one colony forming units of $Escherichia$ $coli$ per reaction within 30 min. Use of the GEAR assay as a means of rapidly identifying bacterial colonies cultured on agar media directly in the reaction without prior DNA extraction was also evaluated. Cells from $Escherichia$ $coli$ colonies were picked and added directly to GEAR assay mastermix without prior DNA extraction. DNA in the cells could be amplified at a constant temperature 60° C., yielding positive results within 15 minutes for 21 of 21 (100%) of the isolates tested. The amplified products were also confirmed using agarose gel electrophoresis. The GEAR technique provides a rapid and cost-effective approach to enable molecular testing in field settings and point of care facilities.

Materials and Methods

Primer Sequences. The primers for the GEAR assay were designed to target the 16S rRNA region of $Escherichia$ $coli$ (FIG. 2A). The turn-back primers for the GEAR assay are shown in FIG. 2B and Table 1. The upper case 3' sequence of the forward primer is complementary to the target sequence with $Escherichia$ $coli$ (position 1308-1329; GENBANK™ Accession No. GU594309, incorporated by reference herein as present in the database on Jul. 6, 2012). The upper case 3' sequence of the reverse primer is complementary to the $Escherichia$ $coli$ target sequence (position 1415-1396; GENBANK™ Accession No. GU594309). The lower case residues correspond to 5'end turn-back sequence. In the FT primer sequence the lower case letter sequence was complementary to the 5' end of the BT primer (position 1371-1353 in FT and position 1353-1371 in BT; GenBank Accession No. GU594309) having a lower-case letter sequence. The sequences of internal primers IR and IF were 5'-GTGGCATTCTGATCCACGATTA-3' (SEQ ID NO: 4; position 1352-1331; GenBank Accession No. GU594309)

and 5'-TACACACCGCCCGTCACA-3' (SEQID NO: 5; position 1375-1392; GenBank Accession No. GU594309) respectively (see FIG. 2B and Table 2).

TABLE 2

Sequence of primers for GEAR assay to amplify *Escherichia coli* 16S DNA

| Name | 5'-Sequence-3' |
|---|---|
| 16S-FT | gcccgggaacgtattcaccCTCCATGAAGTCGGAATCGCTA (SEQ ID NO: 2) |
| 16S-BT | ggtgaatacgttcccgggcTCTTTTGCAACCCACTCCCA (SEQ ID NO: 3) |
| 16S-IR | GTGGCATTCTGATCCACGATTA (SEQ ID NO: 4) |
| 16S-IF | TACACACCGCCCGTCACA (SEQ ID NO: 5) |

The Sensitivity of the GEAR Assay. The sensitivity of the GEAR assay was demonstrated using DNA extracted from $2 \times 10^6$ *Escherichia coli* CFU (ATCC 11775) per milliliter stock cells. A 10-fold DNA dilution series (corresponding to $2 \times 10^6$ to $2 \times 10^{-1}$ CFU) was used to evaluate the sensitivity of the GEAR assay. This 10-fold serial dilution resulted in 2000, 200, 20, 2, and 0.2 CFU per reaction. All isothermal amplification assays were performed in triplicate.

Real-Time Isothermal Amplification Protocols. GEAR assays were carried out by using the primer combination, FT/BT/IR/IF. The GEAR assay was performed with a LOO-PAMP™ DNA amplification Kit (Eiken Chemical, Japan). Briefly, a total reaction volume of 20 µL consisted of 2× buffer, 1.2 µM SYTO9, 0.8 µl (8 U) Bst polymerase and 1 µM of each primer FT, BT, IF and IR. A DNA template volume of 1 µl was added to the reaction mixture. For detection limit testing, the DNA template was equivalent to a known concentration of CFU per reaction as quantified by spread plating on nutrient agar. Negative controls with no template DNA (replaced with nuclease free water) were performed for each reaction series. The reaction was carried out under isothermal condition at 60° C. for 90 minutes in the presence of an intercalating dye (SYTO 9) and fluorescence signal was acquired every minute using an ABI 7500 Real-Time PCR System™ (Applied Biosystems, Foster City, Calif.). All isothermal amplification reactions were carried out in triplicate. A total of 5 µl of the GEAR product was electrophoresed in 2% agarose gels containing Glow Red stain (Biotium, Hayward, Calif.) and visualized by UV transilluminator at 365 nm.

Bacterial Culture. A known quantity of *Escherichia coli* (BioBall strain NCTC 9001-Equivalent ATCC Strain 11775) was obtained as "30-CFU BioBalls" from BTF Pty. Ltd. (Australia). One 30-CFU Bio-Ball was dissolved in 100 µl of sterile water. After 30 seconds, the whole volume was spread onto nutrient agar plate and plates were incubated at 37° C. overnight to obtain isolated colonies. A stab of bacterial cells was picked from an individual colony grown on a nutrient agar plate with the help of sterile aerosol barrier P-20 tip with a simple touch on the surface of the colony. Picked cells were transferred directly into the 20-µl reaction mix. Standard isothermal amplification reactions were carried out by using two primers (FT/BT) or using four primers (FT/BT/IR/IF) for *Escherichia coli*. Appropriate negative controls were included for each set of run.

Results

GEAR Assay. The mechanism of DNA amplification is illustrated in FIG. 2C with a pair of primers (FT and BT). The illustration of isothermal amplification in FIG. 2C is based on a pair of turn-back-primers without internal primers (IR/IF). The lowercase residue of the 5' end turn-back primer sequence of the forward primer is complimentary to the 5' end turn-back primer sequence of the reverse primer. The uppercase residue of the 3' end of the forward and revere primers hybridize to specific regions of target nucleic acid sequence that can prime and extend on the target nucleic acids (FIG. 2C). Initially, the main purpose for the use of lowercase residue 5' end turn-back sequence is to hybridize to the extension product to enable easy separation of amplified products shown in sequence F2 and B2 intermediate (FIG. 2C). As GEAR isothermal amplification progresses, the 5' end turn-back primer sequences are incorporated into the amplified products, leading to exponential self-amplification. The speed and sensitivity of the assay was further improved with an additional pair of primers (IR and IF).

Figure 4:
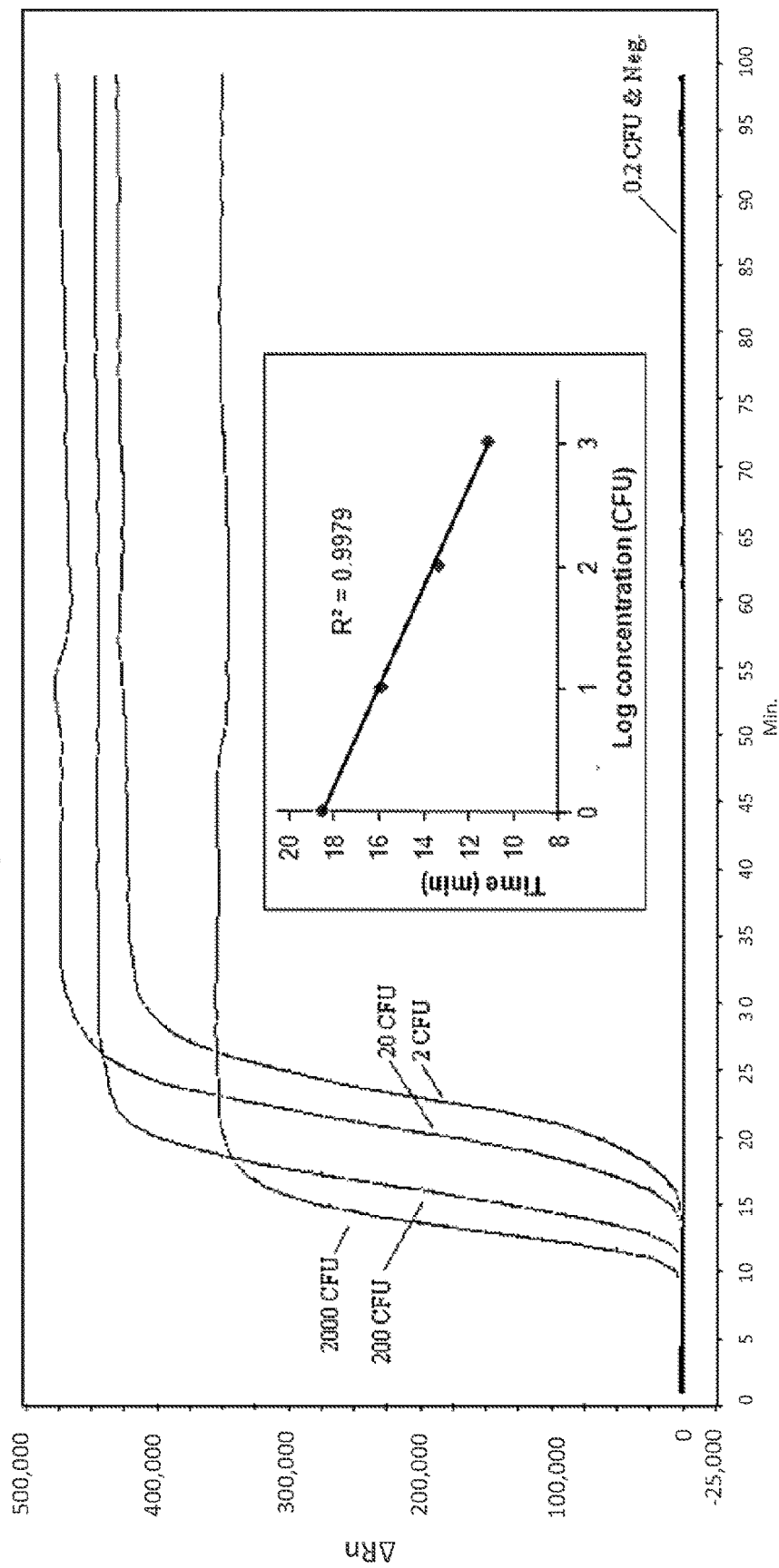
FIG. 4 is a graph illustrating the quantification of serially diluted DNA by GEAR assay amplification. The isothermal amplification plot represents amplification products as observed through real-time fluorescence monitoring at different concentrations of starting template DNA. DNA concentration represents CFU equivalents. Each "cycle" represents one minute of reaction time. The insert figure presents the standard curve obtained by plotting the value of crossing threshold (Ct) versus the concentration of CFU equivalents. Data represent the mean of four replicates for each standard dilution.
Figure 5:
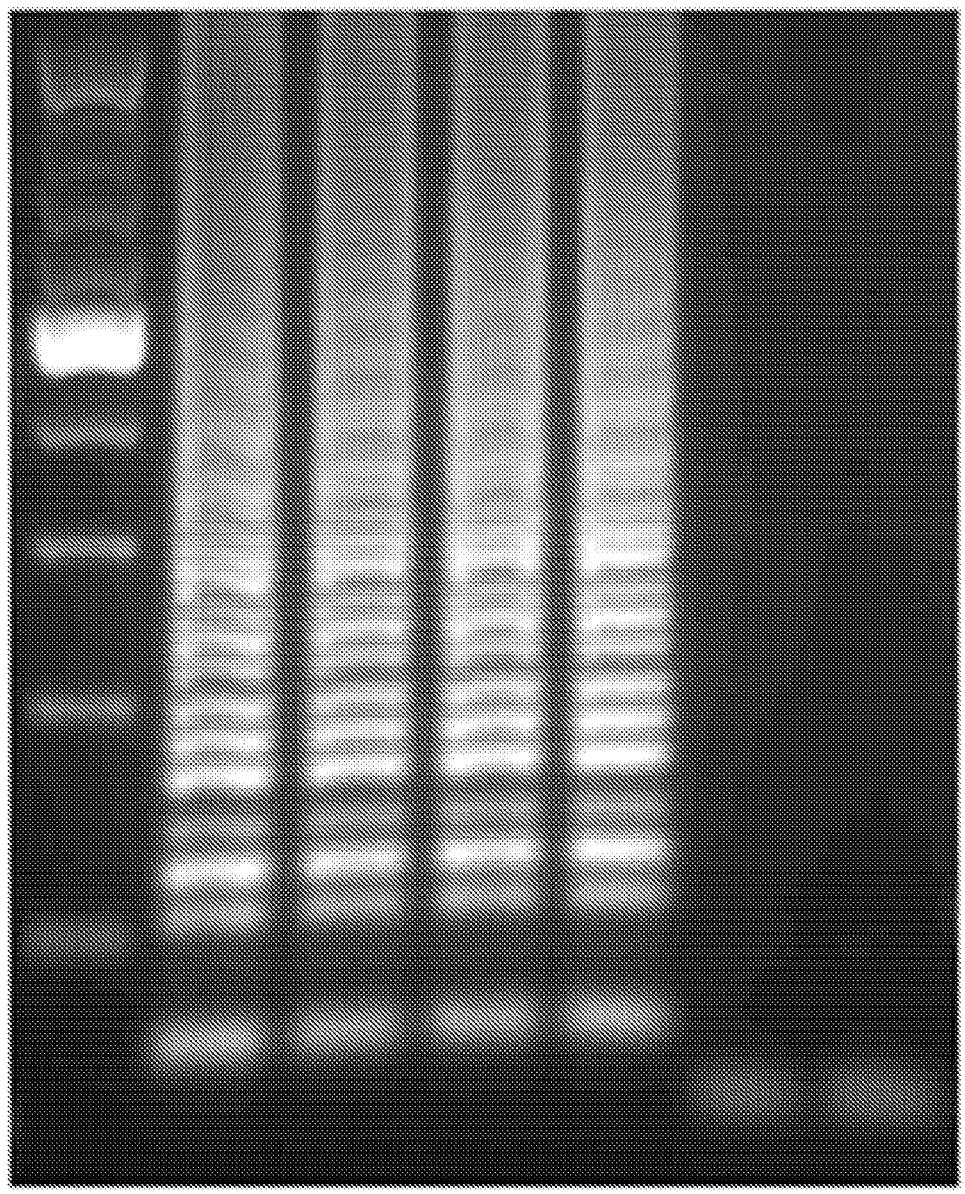
FIG. 5 is a digital image illustrating gel electrophoresis results for amplified GEAR product using the FT/BT/IR/IF primers listed in FIG. 2. Lane M; 100 base-pair (bp) molecular weight marker, Lanes 1 through 5 are 10 fold serial dilution of the amplified product 2000, 200, 20, 2, 0.2 colony forming units (CFU) and Lane 6, negative control.

The Sensitivity of the GEAR Assay. When only the two turn-back primers were used (no internal primers IF and IR), the sensitivity the GEAR assay was relatively low (limit of detection for the *Escherichia coli* target was 1,000 CFU/reaction) and the time-to-detection was relatively long (50 minutes). When the GEAR assay was performed with outer turn-back primers (FT and BT) and internal primers (IR/IF), the measured detection limit for the *Escherichia coli* target was two cells per reaction (FIG. 4). Gel electrophoresis images showed that consistent amplification product sizes were formed by the GEAR assay (FIG. 5). The average and standard deviation of crossing threshold (Ct) values for each serial dilution were 10.2±0.47, 12.4±0.98, 14.9±0.7 and 17.6±1.8 minutes, respectively for the 2000 CFU, 200 CFU, 20 CFU and 2 CFU/reaction template levels. In order to refine the limit of detection further, the DNA was further serially diluted by two-fold serial dilution until the diluted sample represented 1, 0.5 and 0.25 cell per reaction. Using this 2-fold dilution series, three of three DNA samples were positive at one cell per reaction, whereas only two of three were positive at 0.5 cells per reaction and there was no detection for reactions performed with 0.25 cells per reaction. The detection limit of GEAR assay under these conditions was determined to be 1 CFU per reaction.

Isothermal GEAR Assay for Bacterial Colony Analysis. Isothermal amplification using the GEAR assay was successful with a primer pair (i.e., without the internal IF and IR primers) using direct *Escherichia coli* cell transfer to reaction mixes. DNA was amplified from each of the 21 *Escherichia coli* colonies tested and positive signals were obtained in 29.6±1.8 minutes. When the GEAR assay was performed with four primers (FT/BT/IR/IF), from each of the 21 *Escherichia coli* colonies tested and positive signals were obtained in 13.7±2.8 minutes.

Discussion

A novel isothermal amplification assay that offers the same benefits of the LAMP technique, including the ability to enable high throughput screening of bacterial colonies, but which requires fewer primers targeting fewer target regions that the LAMP assay. The GEAR assay differs from the LAMP assay by at least three distinct features. First, GEAR assays use turn-back primers (FT and BT) targeting three target regions, whereas LAMP assays use turn-back primers targeting four regions on the target nucleic acid. Second, primer design for the GEAR technique differs from the LAMP technique in that the 5' end between forward and reverse primers are complementary, whereas the corresponding turn-back primers for use with the LAMP assay (FIP and BIP) do not form a complementary structure at the 5' end. Third, GEAR assays do not require outer strand displacement primers for an efficient assay, whereas LAMP assay requires two outer strand displacement primers (F3 and B3); thus, while the LAMP assay requires six primers for efficiency, the GEAR assay only requires four primers.

The isothermal amplification of the reaction proceeds due to the presence of the turn-back primer sequence in the primer and resulting conformational change during the amplification. In a previous study, the detection limit of a PCR assay targeting the 16S rRNA gene of *Escherichia coli* was reported to be three cells (Tsai and Olson, *Appl Environ Microbiol* 58, 2292-2295, 1992). The 16S rRNA-based GEAR assay utilizing four primers (FT, BT, IF, IR) was able to achieve a similar detection limit (one *Escherichia coli* cell per reaction).

A typical positive GEAR assay produced a ladder of multiple bands on an agarose gel (FIG. 4B), suggesting that DNA with repeat target sequences were produced due to different exponential amplification stages as a result of simultaneous Bst DNA polymerase extension at 3' and strand displacement at 5' end. Inclusion of the DNA intercalating dye (SYTO9) in the reaction buffer permitted real-time monitoring of fluorescence without the need for gel electrophoresis or visual inspection of the tubes DNA amplification indicators (e.g., turbidity, precipitates).

The GEAR assay was also used to identify *Escherichia coli* colonies using cells picked directly from colonies on agar plates without nucleic acid extraction. This demonstrated that the GEAR assay can be used to identify colonies grown on agar plates within 15 minutes without requiring the time and expense of extracting DNA.

This example illustrates application of the GEAR assay for isothermal amplification of *Escherichia coli* DNA with either a set of two or a set of four primers. Two-primer GEAR assays (FT and BT) were found to be effective in enabling rapid amplification of DNA from bacterial colony picks from agar plates, indicating that this technique could be useful, for example, for enabling rapid screening of bacterial isolates. The ability of the GEAR assay to detect as low as 1 cell per reaction within an hour indicates that this technique can be effective in the development of biosensor-based analytical instruments. For example, a biosensor that integrates the GEAR assay can be used for point of care testing (POCT) to indicate the presence of target nucleic acid allowing real-time fluorescent monitoring using an intercalating dye (e.g., SYTO 9 or SYBR Green), molecular beacon or FRET assay. The combination of the fluorescence based read out of GEAR with optical fiber integration in the microfluidic chip permits development of POCT analytical devices for field application, for example in the event of epidemic outbreak. The GEAR technique provides a cost-effective alternative for rapid isothermal molecular analysis of clinical, environmental, or biological samples in field settings or point of care facilities.

Example 2

Comparison of LAMP and GEAR Assays for the Detection of *Escherichia coli*

This example illustrates comparison of LAMP and GEAR assays for the detection of *Escherichia coli*. The 16S GEAR assay primers for the detection of *Escherichia coli* described in Example 1 were used for the GEAR assay (see FIG. 2A). LAMP primers targeting the same region (16S) as that of GEAR assay for the detection of *Escherichia coli* were designed and produced (see Table 3).

TABLE 3

LAMP Primers for amplification of 16S *Escherichia coli* DNA (5'-3').

| Name | 5'-Sequence-3' |
|---|---|
| 16S-F3 | CCATGAAGTCGGAATCGCTA (SEQ ID NO: 6) |
| 16S-B3 | CGCCCTTGGTTACCTTGTTC (SEQ ID NO: 7) |
| 16S-FIP | TGACGGGCGGTGTGTACAAGAATCGTGGATCAGAATGCCA (SEQ ID NO: 8) |
| 16S-BIP | ACCATGGGAGTGGGTTGCAAAACACCCCAGTCATGAATCACA (SEQ ID NO: 9) |
| 16S-LF | GCCCGGGAACGTATTCACC (SEQ ID NO: 10) |
| 16S-LB | GTAGGTAGCTTAACCTTCGGGAGGG (SEQ ID NO: 11) |

Figure 6:
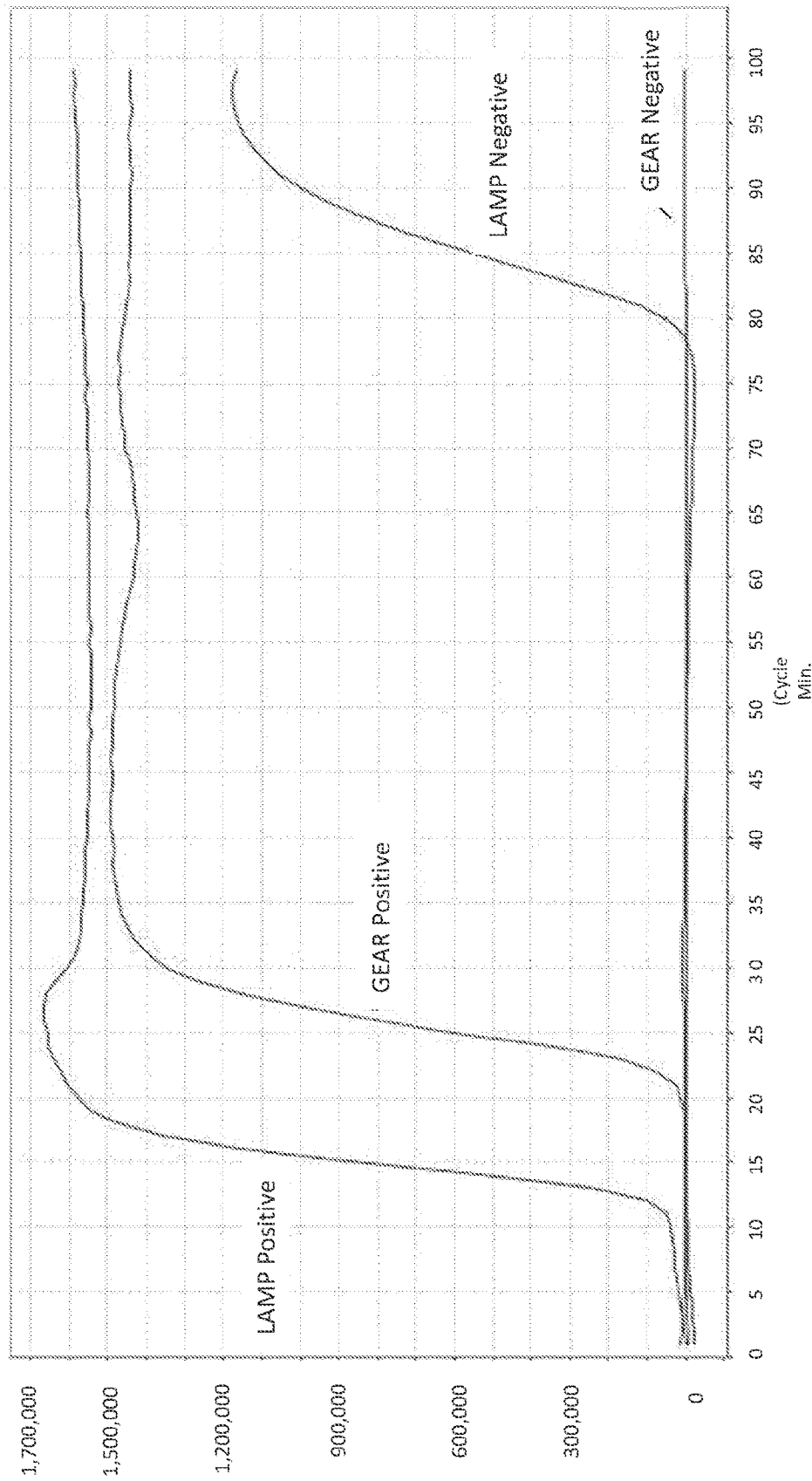
FIG. 6 is a graph illustrating the comparison of 16S based LAMP and GEAR assays for the detection of *Escherichia coli* using the ABI 7500 platform (Applied Biosystems, Foster City, Calif.). The LAMP assay generates false positive at 80 minutes in the negative control whereas GEAR assay negative control remains negative even for 99 minutes.
Figure 7:
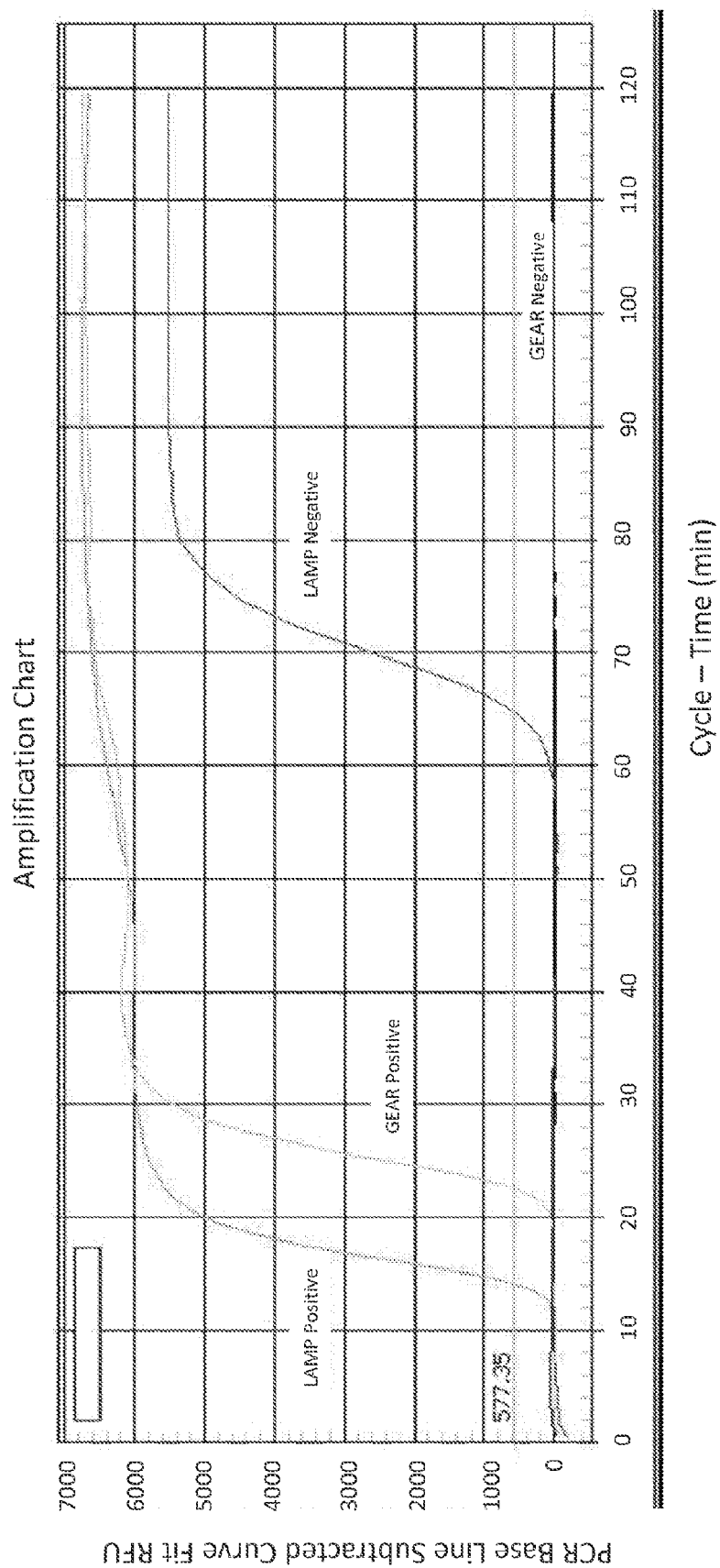
FIG. 7 is a graph illustrating the comparison of 16S based LAMP and GEAR assays for the detection of *Escherichia coli* on the BIO-RAD IQ5™ platform (Bio-Rad, Inc., Hercules, Calif.). The LAMP assay generates false positive at 65 minutes in negative sample whereas GEAR assay negative sample remains negative even for 120 minutes.
Figure 8:
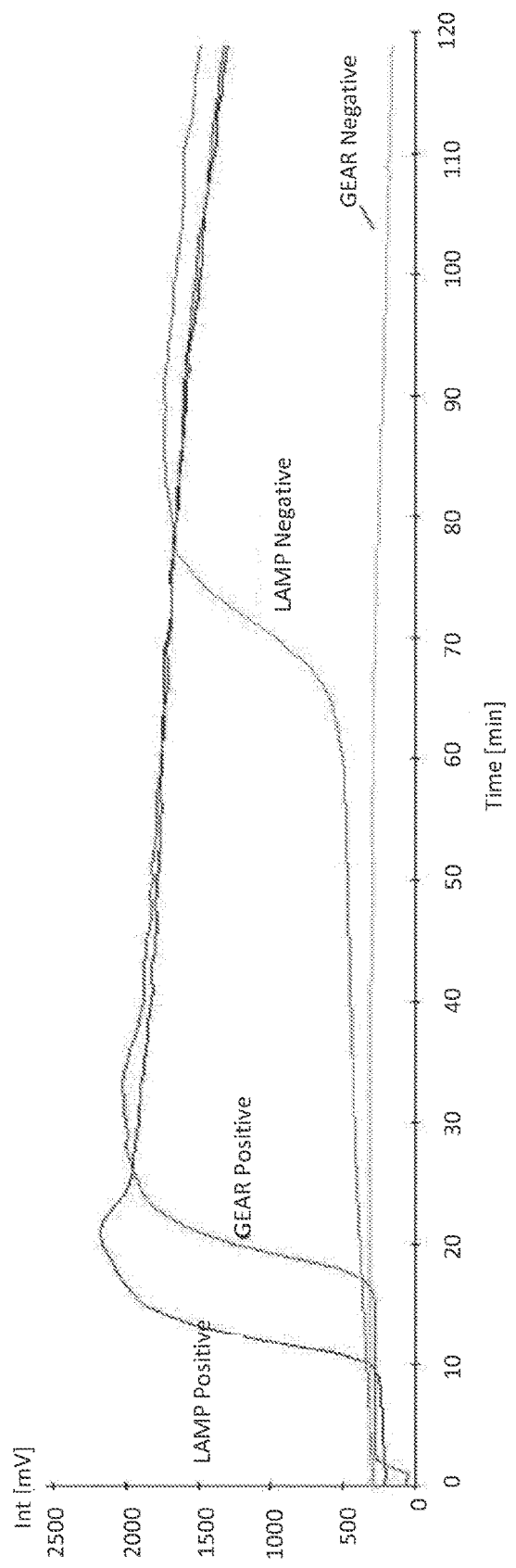
FIG. 8 is a graph illustrating the comparison of 16S based LAMP and GEAR assays for the detection of *Escherichia coli* on the ESEQUANT™ Tube Scanner platform (Qiagen GmbH, Hilden, DE). The LAMP assay generates false positive at 65 minutes in negative sample whereas GEAR assay negative sample remains negative even for 120 minutes.

The same buffer, enzyme and temperature (60° C.) conditions were used for both the LAMP and GEAR assay for detection of *Escherichia coli* DNA in three different real-time platforms (ABI 7500 (FIG. 6), Bio-RAD-iQ5 (FIG. 7) and Tube scanner from ESE/Qiagen (FIG. 8)). The LoopAmp amplification DNA kit (1×) was used for LAMP and GEAR assays, which contained 20 mM Tris-HCl (pH 8.8), 10 mM KCl, 8 mM MgSO$_4$, 10 mM (NH$_4$)$_2$SO$_4$, 0.1% Tween20, 0.8 M Betaine, 1.4 mM dNTPs, 8U Bst Polymerase and 1 µM SYTO-9. The concentrations of primers for LAMP assay used were 0.2 µM each of the outer primer (F3/B3), 0.8 µM each of the loop primer (LF/LB), 1.6 µM each of the inner primer (FIP/BIP) and the primer concentrations for GEAR assay used were 1 µM each of the primer (FT/BT/IR/IF). Reactions were carried out at 60° C. for 60 min and fluorescence signal acquired every minute using an ABI 7500 Real-Time PCR System™ (Applied Biosystems, Foster City, Calif.). The primer concentration for the LAMP assay as recommended by the manufacturer was used (described above) (Eiken Chemical, Japan) and the primer concentration for the GEAR assay was as described in Example 1. Results of the LAMP and GEAR assays are shown in FIGS. 6-8.

When the results of the LAMP assay (six primers targeting eight regions) were compared with the results of the GEAR assay (four primers targeting five regions) for the detection of *Escherichia coli*, the LAMP assay generated false positive result in negative samples in all three platforms, whereas the GEAR assay did not generate a false positive result using any of the platforms. One non-limiting explanation is that using more primers produced the false positive results in the LAMP assay. Regarding the GEAR assay, the positive signal generation was observed approximately five to ten minutes later than LAMP assay but no false positive results observed in any negative samples in all three platforms. Also running the GEAR assay even for two hours or more did not produce any false positive results. In some examples, this is a useful feature of the GEAR assay, for example, if the assay is performed with a water bath or heating block in the field where the reaction could potentially be extended beyond an hour because of manual operation.

Example 3

Comparison of LAMP and GEAR Assays for Detection of *Vibrio cholerae*

This example illustrates comparison of LAMP and GEAR assays for the detection of *Vibrio cholerae*.

The primers used for the LAMP and GEAR assays are shown in Tables 4 and 5. The primers used for the LAMP assay to detect *Vibrio cholerae* are the same as those previously described in Yamazaki et al. *BMC Microbiology*, 8:94, 2008. All primers were designed from the sequence of the ctxA gene of *V. cholerae* (GenBank Accession# K02679, incorporated by reference herein as present in the database on Mar. 6, 2012), shown below:

```
                                        (SEQ ID NO: 12)
aaaaacagaaaatgataaaaaaggactaaatagtatattttgatttttg attttcgattttgatttcaaataatacaaatttatttacttatttaat tgttttgatcaattattttctgttaaacaaagggagcattatatggta aagataatatttgtgtttttatttcttatcatcattttcatatgcaa atgatgataagttatatcgggcagattctagacctcctgatgaaataaa gcagtcaggtggtcttatgccaagaggacagagtgagtactttgaccga ggtactcaaatgaatatcaaccttatgatcatgcaagaggaactcaga cgggatttgttaggcacgatgatggatatgtttccacctcaattagttt gagaagtgcccacttagtgggtcaaactatattgtctggtcattctact tattatatatgttatagccactgcacccaacatgtttaacgttaatg atgtattaggggcatacagtcctcatccagatgaacaagaagtttctgc tttaggtgggattccatactcccaaatatatggatggtatcgagttcat tttggggtgcttgatgaacaattacatcgtaatagggctacagagata gatattacagtaacttagatattgctccagcagcagatggttatggatt ggcaggtttccctccggagcatagagcttggagggaagagccgtggatt catcatgcaccgccgggttgtgggaatgctccaagatcatcg
```

TABLE 4

LAMP Assay primers for the detection of *V. cholerae*.

| Primer name | 5'-Sequence-3' | ctxA Gene Location |
|---|---|---|
| CtxA-FIP | TCTGTCCTCTTGGCATAAGACGCAGATTC TAGACCTCCTG (SEQ ID NO: 13) | 277-257 (F1c), 217-235 (F2) |
| CtxA-BIP | TCAACCTTTATGATCATGCAAGAGGCTCA AACTAATTGAGGTGGAA (SEQ ID NO: 14) | 311-335 (B1), 395-375 (B2c) |
| CtxA-F3 | GCAAATGATGATAAGTTATATCGG (SEQ ID NO: 15) | 193-216 |
| CtxA-B3 | GMCCAGACAATATAGTTTGACC (SEQ ID NO: 16) | 433-412 |
| CtxA-LF | CACCTGACTGCTTTATTTCA (SEQ ID NO: 17) | 256-237 |
| CtxA-LB | AACTCAGACGGGATTTGTTAGG (SEQ ID NO: 18) | 336-357 |

TABLE 5

GEAR Assay primers for the detection of *V. cholerae*.

| Primer Name | 5'-Sequence-3' | Gene Location |
|---|---|---|
| CtxA-FT | tggcataagaccacctgactgctGC AAATGATGATAAGTTATATCGGGC (SEQ ID NO: 19) | 267-245 (lower case), 193-218 (upper case) |
| CtxA-BT | agcagtcaggtggtcttatgccaAA AGGTTGATTATTCATTGAGTACCTCG (SEQ ID NO: 20) | 245-267 (lower case), 319-292 (upper case) |
| CtxA-IR | TATTTCATCAGGAGGTCTAGAATC (SEQ ID NO: 21) | 243-220 |
| CtxA-IF | GAGGACAGAGTGAGTACTTTGA (SEQ ID NO: 22) | 269-290 |

The LoopAmp amplification DNA kit (1×) was used for LAMP and GEAR assays, which contained 20 mM Tris-HCl (pH 8.8), 10 mM KCl, 8 mM $MgSO_4$, 10 mM $(NH_4)_2SO_4$, 0.1% Tween20, 0.8 M Betaine, 1.4 mM dNTPs, 8U Bst Polymerase and 1 µM SYTO-9. The concentrations of primers for LAMP assay used were 0.2 µM each of the outer primer (F3/B3), 0.8 µM each of the loop primer (LF/LB), 1.6 µM each of the inner primer (FIP/BIP) and the primer concentrations for GEAR assay used were 1 µM each of the primer (FT/BT/IR/IF). Reactions were carried out at 65° C. for 60 minutes and fluorescence signal acquired every minute using an ABI 7500 Real-time PCR System™ (Applied Biosystems, Foster City, Calif.).

Figure 9:
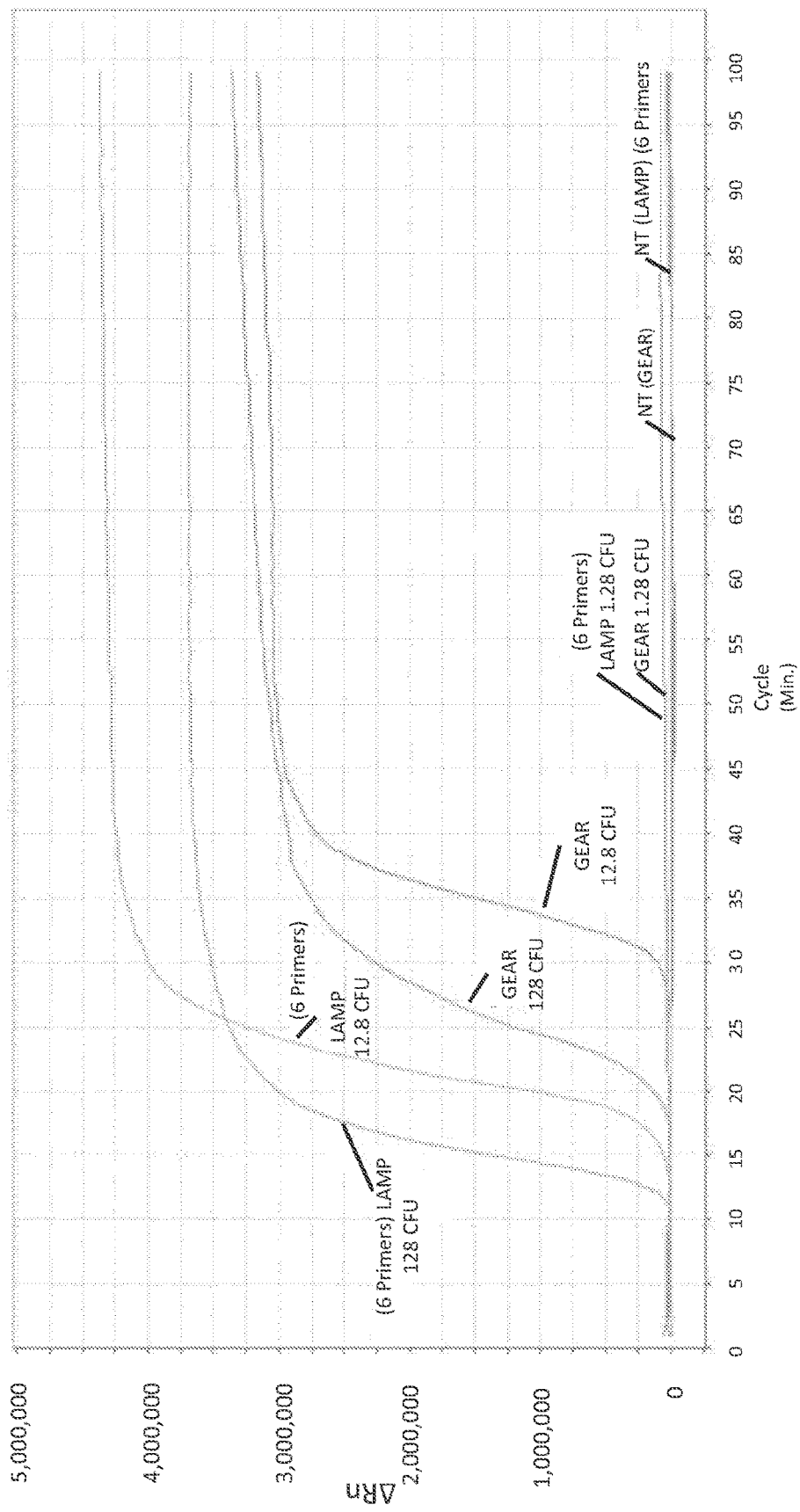
FIG. 9 is a graph illustrating the comparison of the accelerated LAMP assay (6 primers) and the GEAR assay (4 primers) for the detection of *Vibrio cholerae*.
Figure 10:
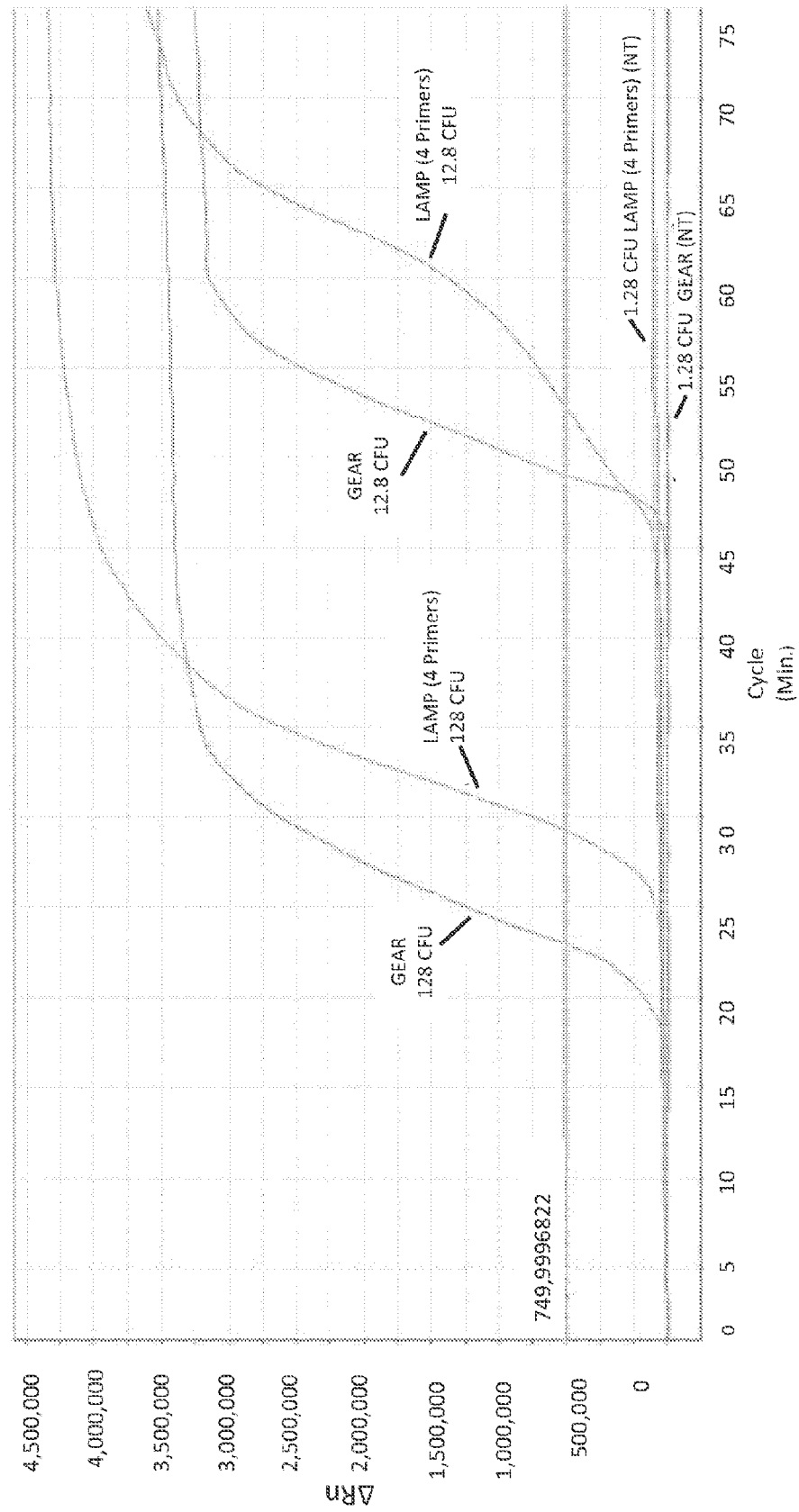
FIG. 10 is a graph illustrating the comparison of the conventional LAMP assay (4 primers) and the GEAR assay (4 primers) for the detection of *Vibrio cholerae*.

The conventional LAMP assay (four primers) was originally developed and reported in 2000 (Notomi et al., *Nucleic Acids Res.*, 28:e63, 2000) and subsequently the accelerated LAMP assay (six primers) was developed (Nagamine et al., *Mol. Cell Probes*, 16:223-229, 2002) to speed up the reaction time. The results provided in this example illustrate that the GEAR assay (four primers) detects the DNA target earlier than conventional LAMP assay (six primers) based on the crossing threshold (Ct) values (see FIG. 9 and Table 6). When accelerated LAMP assay (six primers) is employed then the DNA target is detected earlier than GEAR assay based on the crossing threshold (Ct) values (see FIG. 10 and Table 7).

TABLE 6

Comparison of accelerated LAMP assay (six primers) and GEAR assay (four primers) for the detection of *V. cholerae*.

| CFU/reaction | 128 | 12.8 | 1.28 |
|---|---|---|---|
| LAMP (Ct) | 12.7 | 17.7 | Neg |
| GEAR (Ct) | 21.2 | 31.1 | Neg |

Colony forming units (CFU), Neg (no fluorescence), No template (NT), Crossing threshold (CT), Accelerated LAMP assay contains six primers (CtxA-FIP, CtxA-BIP, CtxA-F3, CtxA-B3, CtxA-LF and CtxA-LB) targeting eight regions and GEAR assay contains four primers (CtxA-FT, CtxA-BT, CtxA-IR and CtxA-IF) targeting five regions.

TABLE 7

Comparison of conventional LAMP assay (4 primers) and GEAR assay (4 primers) for the detection of *V. cholerae*.

| CFU/reaction | 128 | 12.8 | 1.28 | NT |
|---|---|---|---|---|
| LAMP (Ct) | 29.3 | 53.0 | Neg | Neg |
| GEAR (Ct) | 22.9 | 49.0 | Neg | Neg |

Colony forming units (CFU), Neg (no fluorescence), No template (NT), Crossing threshold (CT), Conventional LAMP assay contains four primers targeting six regions (CtxA-FIP, CtxA-BIP, CtxA-F3 and CtxA-B3) and GEAR assay contains four primers (CtxA-FT, CtxA-BT, CtxA-IR and CtxA-IF) targeting five regions.

Example 4

Human Genomic DNA Amplification

This example illustrates use of the GEAR assay for isothermal amplification of human DNA from saliva. The amplification of human DNA with GEAR primers can be used, for example, as a positive control that nucleic acids are present in a sample; for example as a positive control for a GEAR assay for an alternative target nucleic acid molecule.

Figure 11:
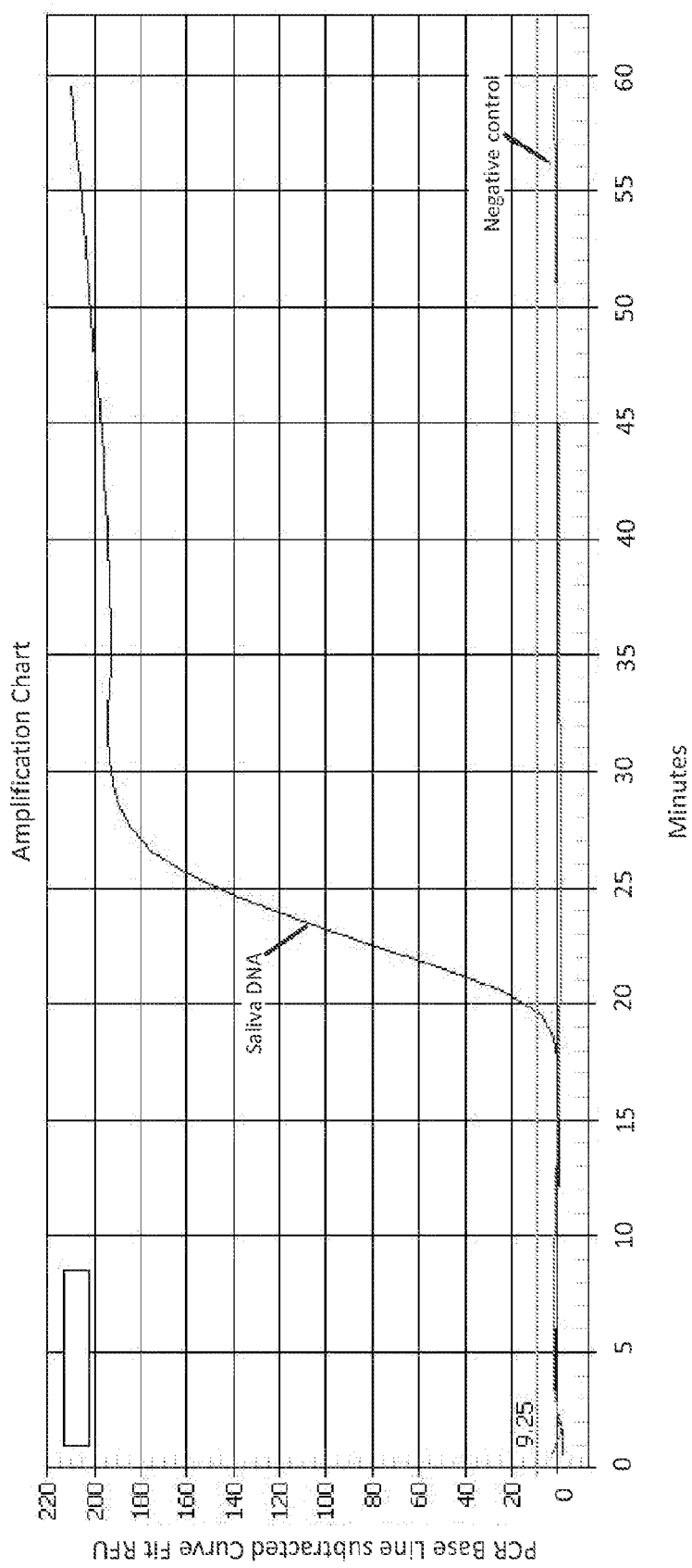
FIG. 11 is a graph illustrating isothermal amplification of human DNA from saliva without nucleic acid extraction using the GEAR assay.

The GEAR assay was performed to directly amplify human DNA from saliva without DNA extraction using a BioRad IQ5 instrument for real-time monitoring of amplification product. The total isothermal reaction volume was 20 µL. Each reaction contained NEB isothermal amplification buffer 1× (pH 8.8, Tris-HCl 20 mM final concentration), $(NH_4)SO_4$ (10 mM final concentration), KCl (50 mM final concentration), $MgCl_2$ (8 mM final concentration), 0.1% Tween-20, each of the 4 dNTPs (1.4 mM final concentration), one micromole of each GEAR primer targeting a region of the thymidylate synthase gene (ThyS-FT, ThyS-BT ThyS-IR and ThyS-IF; see Table 8), SYTO 9 (1 µM final concentration), and 8 units of Bst DNA polymerase 2.0. One microliter of human saliva (the human DNA sample) was added as template to the above GEAR reaction mixture. Amplification was performed at a constant temperature of 65° C. and fluorescence collected every minute for one hour. FIG. 11 shows the amplification of DNA from saliva at 65° C.

TABLE 8

GEAR Assay primers for the isothermal amplification of human DNA from saliva targeting the thymidylate synthase gene.

| Primer Name | 5'-Sequence-3' | Gene Location* |
|---|---|---|
| ThyS-FT | gctcactgttcaccacatagaactggcTC TTCCTCTGATGGCGCT (SEQ ID NO: 23) | 622-596 (lower case), 558-575 (upper case) |
| ThyS-BT | gccagttctatgtggtgaacagtgagcCC CATGTCTCCCGATCTC (SEQ ID NO: 24) | 596-622 (lower case), 659-642 (upper case) |
| ThyS-IR | GAGGGCATGGCATGGAG (SEQ ID NO: 25) | 594-578 |
| ThyS-IF | GTCCTGCCAGCTGTACC (SEQ ID NO: 26) | 624-640 |

*Position based on GENBANK ™ Accession No. AY890751, incorporated by reference herein as present in the GenBank database on Jul. 6, 2012.

Example 5

Viral RNA Amplification Using the GEAR Assay

This example illustrates isothermal amplification of viral RNA using the GEAR assay.

Figure 12:
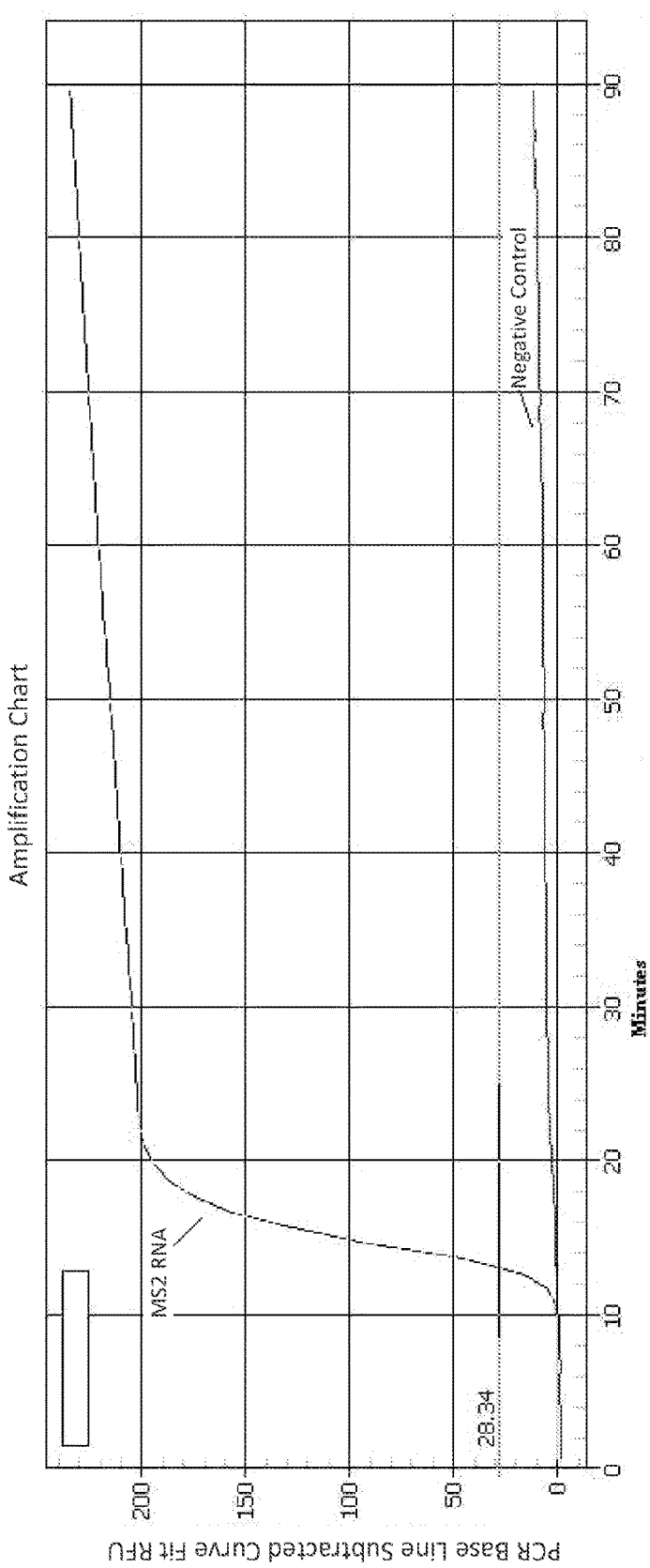
FIG. 12 is a graph illustrating the isothermal amplification of viral RNA using the GEAR assay.

The reverse transcriptase (RT)-GEAR assay was performed to amplify viral RNA using BioRad IQ5 instrument for real-time monitoring of amplification product. The total isothermal reaction volume was 20 µL. Each reaction contained NEB isothermal amplification buffer 1× (pH 8.8, Tris-HCl 20 mM final concentration), $(NH_4)SO_4$ (10 mM final concentration), KCl (50 mM final concentration), $MgCl_2$ (8 mM final concentration), 0.1% Tween-20, each of the 4 dNTPs (1.4 mM final concentration), one micromole of each GEAR primer targeting the assembly protein gene MS2 (MS2-FT, MS2-BT, MS2-IF and MS2-IR; see Table 9), SYTO 9 (1 µM final concentration), 8 units of Bst DNA polymerase 2.0 and 0.2 µl of RT enzyme (QIAGEN). One microliter of RNA was added as template to the above RT-GEAR reaction mixture. Reverse transcriptase (RT) was performed at 50° C. followed by amplification at a constant temperature of 70° C. and fluorescence collected every minute for one hour. FIG. 12 shows the amplification of the RNA template at 70° C.

Bst DNA polymerase 2.0 can amplify the targets at reaction temperature as high as 70° C. compared to Bst DNA polymerase large fragment, which can amplify nucleic acids at a temperature of up to 65° C. Both polymerases can be obtained from New England Biolabs (NEB). The temperature 70° C. was used for isothermal amplification of RNA to increase the specificity.

TABLE 9

GEAR Assay primers for the amplification of MS2 virus RNA

| Primer Name | 5'-Sequence-3' | Gene Location* |
|---|---|---|
| MS2-FT | ggcaccttttcccacactataccGCACG TTTGGCATGGTTGTC (SEQ ID NO: 27) | 1004-982 (lower case), 937-956 (upper case) |
| MS2-BT | ggtatagtgtgggaaaaggtgccTCGAG CATGTTACCTACAGGT (SEQ ID NO: 28) | 982-1004 (lower case), 1052-1032 (upper case) |
| MS2-IR | AGTGGGTTCAAGATACCTAGAG (SEQ ID NO: 29) | 980-959 |
| MS2-IF | TCATTCGTTGTCGACTGGCTC (SEQ ID NO: 30) | 1009-1029 |

*Position based on GENBANK ™ Accession No. GQ153927, incorporated by reference herein as present in the GenBank database on Jul. 7, 2012.

Example 6

Detection of Amplified Nucleic Acid

This example illustrates a method for detecting amplified nucleic acid molecules. Although this example is directed to detection of nucleic acids amplified using the GEAR assay, the person of ordinary skill in the art will appreciate that the method can be used to detect nucleic acid molecules amplified using other amplification techniques, for example, LAMP. In particular, this example illustrates the use of malachite green (MG) as a dye in isothermal amplification reaction.

Isothermal GEAR assay generates large amounts of pyrophosphate ion (PPi), as does loop mediated isothermal amplification (LAMP), as a by-product. The PPi reacts with $Mg^{2+}$ to form a white precipitate. The white precipitate is often hard to visualize in positive GEAR or LAMP reactions. Intercalating dyes such as SYBR Green (Parida et al., *J. Clin. Micro.*, 43:2895-2903, 2005, and Hill et al., *J. Clin. Micro.*, 46:2800-2804, 2008), Picogreen (Dukes et al., *Arch*

Virol., 151:1093-1106, 2006 and Curtis et al., *J. Virol. Meth.,* 151:264-270, 2008) or propidium iodide (Hill et al., *J. Clin. Micro.,* 46:2800-2804, 2008) can be added to the solution after the completion of the LAMP reaction to observe color change but opening the tube may result in cross contamination in subsequent samples. To overcome this difficulty Goto et al. (*BioTechniques,* 46(3):167-172, 2009) reported a simple colorimetric assay by adding hydroxynaphthol blue (HNB), a colorimetric metal indicator in the buffer prior to LAMP reaction. When the LAMP reaction is positive, a color change violet or purple to sky blue indicating a positive reaction. However, it can be difficult to judge the color change from purple to sky blue to interpret positive or negative LAMP reaction.

Malachite Green (MG) Stock. A dilute stock solution of 0.1% MG was prepared by diluting 5% MG solution by 50 times in nuclease free water or deionized distilled water. This stock (0.1%) served as 25× and 0.8 µl was added to 20 µl of isothermal GEAR reaction master mix to obtain a final concentration of 0.004%. The same concentration was used in the LAMP assay.

Isothermal GEAR Reaction Conditions. LoopAmp amplification DNA kit (1×) was used for the GEAR assay, which contained 20 mM Tris-HCl (pH 8.8), 10 mM KCl, 8 mM MgSO$_4$, 10 mM (NH4)$_2$SO$_4$, 0.1% Tween20, 0.8 M Betaine, 1.4 mM dNTPs, 8U Bst Polymerase and 0.8 µl MG. The concentrations of primers used were 1 µM each of the primer (FT/BT/IR/IF). A DNA template volume of 1 µl was added to the reaction mixture in positive controls. Reactions were carried out at 60° C. for 45 min in a heating block.

Figure 13A:
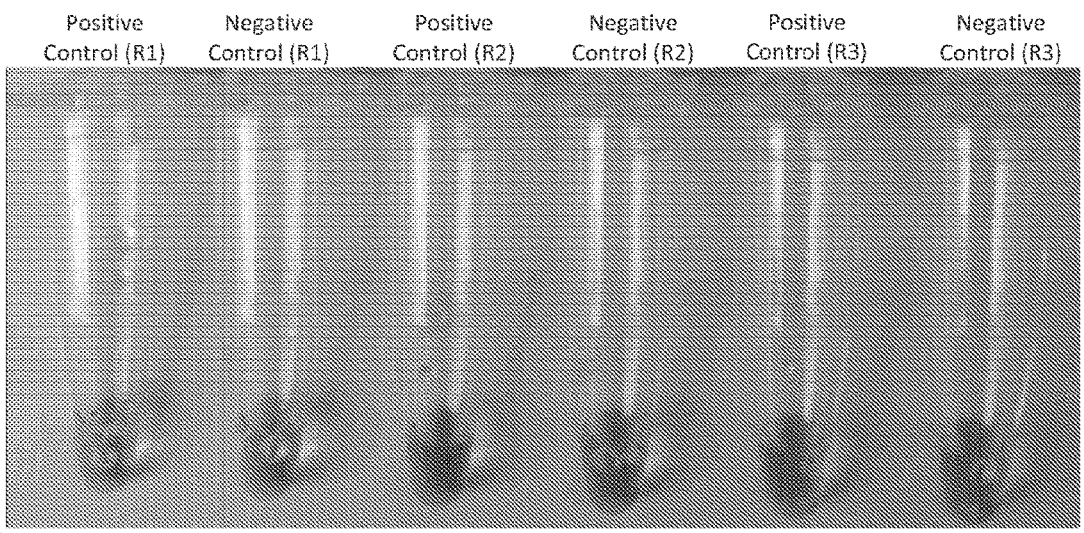
FIGS. 13A and 13B illustrate use of malachite green (MG) to detect positive and negative isothermal amplification assays.
Figure 13B:
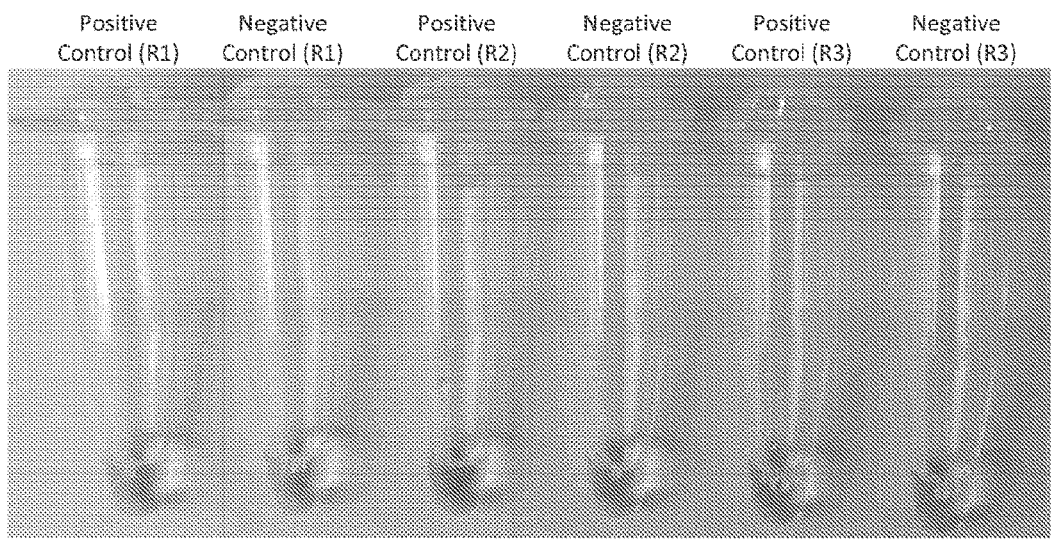

Results. MG provided in the isothermal GEAR reaction assay results in no color change (blue) in positive sample while negative sample turns colorless within 45 minutes at 60° C. The change was detectable without the necessity of any measuring device (see FIGS. 13A and 13B). Similar results were obtained with LAMP.

In view of the many possible embodiments to which the principles of the disclosure may be applied, it should be recognized that the illustrated embodiments are only examples of the disclosure and should not be taken as limiting the scope of the disclosure. Rather, the scope of the disclosure is defined by the following claims.

We claim:

1. A method of amplifying a target nucleic acid molecule comprising from 5' to 3', a 5'-end region, a center region, and a 3'-end region, wherein each region is non-overlapping and comprises at least 10 consecutive nucleotides, comprising:
contacting the target nucleic acid molecule under conditions sufficient for isothermal amplification with an effective amount of:
a forward turn-back primer comprising a first segment comprising at least 10 consecutive nucleotides capable of hybridizing to the center region and a second segment comprising at least 10 consecutive nucleotides capable of hybridizing to the complement of the 5'-end region, wherein the first segment is 5' to the second segment; and
a reverse turn-back primer comprising a first segment comprising at least 10 consecutive nucleotides capable of hybridizing to the complement of the center region and a second segment comprising at least 10 consecutive nucleotides capable of hybridizing to the 3'-end region, wherein the first segment is 5' to the second segment; and
amplifying the target nucleic acid molecule using isothermal amplification.

2. The method of claim 1, wherein,
the first segment of the forward turn-back primer comprises at least 10 consecutive nucleotides of the complement of the center region;
the second segment of the forward turn-back primer comprises at least 10 consecutive nucleotides of the 5'-end region;
the first segment of the reverse turn-back primer comprises at least 10 consecutive nucleotides of the center region;
the second segment of the reverse turn-back primer comprises at least 10 consecutive nucleotides complementary to the 3'-end region; or
two or more thereof.

3. The method of claim 1, wherein the nucleic acid molecule further comprises an internal reverse region and an internal forward region, and wherein, from 5' to 3', the nucleic acid molecule comprises the 5'end region, the internal reverse region, the center region, the internal forward region and the 3'end region, wherein each region is non-overlapping and comprises at least 10 consecutive nucleotides, and wherein the method further comprises:
contacting the target nucleic acid molecule with an effective amount of
an internal forward primer comprising at least 10 consecutive nucleotides capable of hybridizing to the complement to the internal forward region; and
an internal reverse primer comprising at least 10 consecutive nucleotides capable of hybridizing to the internal reverse region.

4. The method of claim 3, wherein,
the first segment of the forward turn-back primer comprises at least 10 consecutive nucleotides of the complement of the center region;
the second segment of the forward turn-back primer comprises at least 10 consecutive nucleotides of the 5'-end region;
the first segment of the reverse turn-back primer comprises at least 10 consecutive nucleotides of the center region;
the second segment of the reverse turn-back primer comprises at least 10 consecutive nucleotides complementary to the 3'-end region;
the internal forward primer comprises at least 10 consecutive nucleotides of the internal forward region;
the internal reverse primer comprises at least 10 consecutive nucleotides complementary to the internal reverse region; or
two or more thereof.

5. The method of claim 1, wherein the forward turn-back primer, the reverse turn-back primer or both, are from 20-50 nucleotides in length.

6. The method of claim 3, wherein the internal forward primer, the internal reverse primer or both, are from 10-50 nucleotides in length.

7. The method of claim 1, wherein the first segment of the forward turn-back primer comprises at least 10 consecutive nucleotides complementary to the first segment of the reverse turn-back primer.

8. The method of claim 1, wherein the first segment of the forward turn-back primer consists of the nucleotide sequence complementary to the center region and the first segment of the reverse turn-back primer consists of the nucleotide sequence of the center region.

9. The method of claim 1, further comprising detecting the amplified target nucleic acid molecule.

10. The method of claim 9, wherein detecting the target nucleic acid molecule comprises real-time isotheral amplification.

11. The method of claim 9, wherein detecting the amplified target nucleic acid molecule comprises contacting the amplified target nucleic acid molecule with a DNA intercalating dye.

12. The method of claim 1, wherein isothermal amplification comprises amplification at about 50 to 75° C.

13. The method of claim 1, wherein amplifying the target nucleic acid molecule does not include the use of an outer strand displacement primer.

14. The method of claim 1, wherein amplifying the target nucleic acid molecule includes use of a strand-displacement polymerase.

15. A method of identifying a target nucleic acid molecule in a biological sample, comprising amplifying the target nucleic from the biological sample according to the method of claim 1 and detecting the amplified target nucleic acid molecule, thereby identifying the target nucleic acid molecule in a biological sample.

16. The method of claim 1, wherein the target nucleic acid molecule comprises the nucleotide sequence set forth as SEQ ID NO: 1 and wherein
the forward turn-back primer comprises or consists of the nucleotide sequence set forth as SEQ ID NO: 2;
the reverse turn-back primer comprises or consists of the nucleotide sequence set forth as SEQ ID NO:3; or
the forward turn-back primer comprises or consists of the nucleotide sequence set forth as SEQ ID NO: 2 and the reverse turn-back primer comprises or consists of the nucleotide sequence set forth as SEQ ID NO: 3.

17. The method of claim 3, wherein the target nucleic acid molecule comprises the nucleotides sequence set forth as SEQ ID NO: 1 and wherein
the forward turn-back primer comprises or consists of the nucleotide sequence set forth as SEQ ID NO: 2;
the reverse turn-back primer comprises or consists of the nucleotide sequence set forth as SEQ ID NO: 3;
the internal reverse primer comprises or consists of the nucleotide sequence set forth as SEQ ID NO: 4;
the internal forward primer comprises or consists of the nucleotide sequence set forth as SEQ ID NO: 5; or
two or more thereof.

18. A method of identifying *Escherichia coli* in a biological sample, comprising amplifying the target nucleic acid molecule according to claim 16 and detecting the amplified target nucleic acid molecule, wherein detecting the amplified target nucleic acid molecule identifies *Escherichia coli* in the biological sample.

19. The method of claim 1, wherein the target nucleic acid molecule comprises the nucleotide sequence set forth as nucleotides 217-395 of SEQ ID NO: 12 and wherein
the forward turn-back primer comprises or consists of the nucleotide sequence set forth as SEQ ID NO: 19;
the reverse turn-back primer comprises or consists of the nucleotide sequence set forth as SEQ ID NO: 20; or
the forward turn-back primer comprises or consists of the nucleotide sequence set forth as SEQ ID NO: 19 and the reverse turn-back primer comprises or consists of the nucleotide sequence set forth as SEQ ID NO: 20.

20. The method of claim 3, wherein the target nucleic acid molecule comprises the nucleotide sequence set forth as nucleotides 217-395 of SEQ ID NO: 12 and wherein
the forward turn-back primer comprises or consists of the nucleotide sequence set forth as SEQ ID NO: 19;
the reverse turn-back primer comprises or consists of the nucleotide sequence set forth as SEQ ID NO: 20;
the internal reverse primer comprises or consists of the nucleotide sequence set forth as SEQ ID NO: 21;
the internal forward primer comprises or consists of the nucleotide sequence set forth as SEQ ID NO: 22; or
two or more thereof.

21. A method of identifying *Vibrio cholerae* in a biological sample, comprising:
amplifying the target nucleic acid molecule according to claim 19, and
detecting the amplified target nucleic acid molecule, wherein detecting the amplified target nucleic acid molecule identifies *Vibrio cholerae* in the biological sample.

22. The method of claim 1, wherein the target nucleic acid molecule comprises the nucleotide sequence set forth as nucleotides 575-659 of SEQ ID NO: 31 and wherein
the forward turn-back primer comprises or consists of the nucleotide sequence set forth as SEQ ID NO: 23;
the reverse turn-back primer comprises or consists of the nucleotide sequence set forth as SEQ ID NO: 24; or
the forward turn-back primer comprises or consists of the nucleotide sequence set forth as SEQ ID NO: 23 and the reverse turn-back primer comprises or consists of the nucleotide sequence set forth as SEQ ID NO: 24.

23. The method of claim 3, wherein the target nucleic acid molecule comprises the nucleotide sequence set forth as nucleotides 575-659 of SEQ ID NO: 31 and wherein
the forward turn-back primer comprises or consists of the nucleotide sequence set forth as SEQ ID NO: 23;
the reverse turn-back primer comprises or consists of the nucleotide sequence set forth as SEQ ID NO: 24;
the internal forward primer comprises or consists of the nucleotide sequence set forth as SEQ ID NO: 26;
the internal reverse primer comprises or consists of the nucleotide sequence set forth as SEQ ID NO: 25; or
two or more thereof.

24. A method of identifying human nucleic acid in a biological sample, comprising:
amplifying the target nucleic acid molecule according to claim 22, and
detecting the amplified target nucleic acid molecule, wherein detecting the amplified target nucleic acid molecule identifies the human nucleic acid in the biological sample.

25. The method of claim 1, wherein the target nucleic acid molecule comprises the nucleotide sequence set forth as nucleotides 937-1052 of SEQ ID NO: 32 and wherein
the forward turn-back primer comprises or consists of the nucleotide sequence set forth as SEQ ID NO: 27;
the reverse turn-back primer comprises or consists of the nucleotide sequence set forth as SEQ ID NO: 28; or
the forward turn-back primer comprises or consists of the nucleotide sequence set forth as SEQ ID NO: 27 and the reverse turn-back primer comprises or consists of the nucleotide sequence set forth as SEQ ID NO: 28.

26. The method of claim 3, wherein the target nucleic acid molecule comprises the nucleotide sequence set forth as nucleotides 937-1052 of SEQ ID NO: 32 and wherein
the forward turn-back primer comprises or consists of the nucleotide sequence set forth as SEQ ID NO: 27;
the reverse turn-back primer comprises or consists of the nucleotide sequence set forth as SEQ ID NO: 28;

the internal forward primer comprises or consists of the nucleotide sequence set forth as SEQ ID NO: 30;

the internal reverse primer comprises or consists of the nucleotide sequence set forth as SEQ ID NO: 29; or two or more thereof.

27. A method of identifying Viral DNA in a biological sample, comprising:

amplifying the target nucleic acid molecule according to claim 25, and detecting the amplified target nucleic acid molecule, wherein detecting the amplified target nucleic acid molecule identifies Viral DNA in the biological sample.

28. The method of claim 15, wherein:

amplifying the target nucleic acid molecule comprises contacting the target nucleic acid molecule with malachite green;

the target nucleic acid molecule and the malachite green are in a solution; and detecting the amplified target nucleic acid molecule comprises detecting the presence or absence of a visible color of the solution, wherein detecting the visible color of the solution detects the amplified target nucleic acid molecule and detecting the absence of the visible color of the solution detects the absence of the amplified target nucleic acid molecule.

29. The method of claim 1, wherein the target nucleic acid molecule is no more than 250 nucleotides in length.

* * * * *

SEQUENCE LISTING

```
<160> NUMBER OF SEQ ID NOS: 32

<210> SEQ ID NO 1
<211> LENGTH: 109
<212> TYPE: DNA
<213> ORGANISM: Escherichia coli

<400> SEQUENCE: 1
ctccatgaag tcggaatcgc tagtaatcgt ggatcagaat gccacggtga atacgttccc      60
gggccttgta cacaccgccc gtcacaccat gggagtgggt tgcaaaaga                109

<210> SEQ ID NO 2
<211> LENGTH: 41
<212> TYPE: DNA
<213> ORGANISM: Artificial Sequence
<220> FEATURE:
<223> OTHER INFORMATION: Primer

<400> SEQUENCE: 2
gcccgggaac gtattcaccc tccatgaagt cggaatcgct a                         41

<210> SEQ ID NO 3
<211> LENGTH: 39
<212> TYPE: DNA
<213> ORGANISM: Artificial Sequence
<220> FEATURE:
<223> OTHER INFORMATION: Primer

<400> SEQUENCE: 3
ggtgaatacg ttcccgggct cttttgcaac ccactccca                           39

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
gtggcattct gatccacgat ta                                             22

<210> SEQ ID NO 5
```

<211> LENGTH: 18
<212> TYPE: DNA
<213> ORGANISM: Artificial Sequence
<220> FEATURE:
<223> OTHER INFORMATION: Primer

<400> SEQUENCE: 5
tacacaccgc ccgtcaca                                                  18

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
ccatgaagtc ggaatcgcta                                                20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
cgcccttggt taccttgttc                                                20

<210> SEQ ID NO 8
<211> LENGTH: 40
<212> TYPE: DNA
<213> ORGANISM: Artificial Sequence
<220> FEATURE:
<223> OTHER INFORMATION: Primer

<400> SEQUENCE: 8
tgacgggcgg tgtgtacaag aatcgtggat cagaatgcca                          40

<210> SEQ ID NO 9
<211> LENGTH: 42
<212> TYPE: DNA
<213> ORGANISM: Artificial Sequence
<220> FEATURE:
<223> OTHER INFORMATION: Primer

<400> SEQUENCE: 9
accatgggag tgggttgcaa aacacccag tcatgaatca ca                        42

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
gcccgggaac gtattcacc                                                 19

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11

```
gtaggtagct taaccttcgg gaggg                                             25

<210> SEQ ID NO 12
<211> LENGTH: 777
<212> TYPE: DNA
<213> ORGANISM: Vibrio cholerae

<400> SEQUENCE: 12
aaaaacagaa aatgataaaa aaggactaaa tagtatattt tgatttttga tttttgattt       60
ttgatttcaa ataatacaaa tttatttact tatttaattg ttttgatcaa ttattttttct     120 gttaaacaaa gggagcatta tatggtaaag ataatatttg tgttttttat tttcttatca     180 tcatttttcat atgcaaatga tgataagtta tatcgggcag attctagacc tcctgatgaa    240
ataaagcagt caggtggtct tatgccaaga ggacagagtg agtactttga ccgaggtact     300
caaatgaata tcaacccttta tgatcatgca agaggaactc agacgggatt tgttaggcac    360
gatgatggat atgttttccac ctcaattagt ttgagaagtg cccacttagt gggtcaaact    420
atattgtctg gtcattctac ttattatata tatgttatag ccactgcacc caacatgttt    480
aacgttaatg atgtattagg ggcatacagt cctcatccag atgaacaaga agtttctgct   540
ttaggtggga ttccatactc ccaaatatat ggatggtatc gagttcattt tggggtgctt    600
gatgaacaat tacatcgtaa taggggctac agagatagat attacagtaa cttagatatt    660
gctccagcag cagatggtta tggattggca ggtttccctc cggagcatag agcttggagg    720
gaagagccgt ggattcatca tgcaccgccg ggttgtggga atgctccaag atcatcg       777

<210> SEQ ID NO 13
<211> LENGTH: 40
<212> TYPE: DNA
<213> ORGANISM: Artificial Sequence
<220> FEATURE:
<223> OTHER INFORMATION: Primer

<400> SEQUENCE: 13
tctgtcctct tggcataaga cgcagattct agacctcctg                            40

<210> SEQ ID NO 14
<211> LENGTH: 46
<212> TYPE: DNA
<213> ORGANISM: Artificial Sequence
<220> FEATURE:
<223> OTHER INFORMATION: Primer

<400> SEQUENCE: 14 tcaacccttta tgatcatgca agaggctcaa actaattgag gtggaa                    46

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
gcaaatgatg ataagttata tcgg                                             24

<210> SEQ ID NO 16
<211> LENGTH: 22
<212> TYPE: DNA
<213> ORGANISM: Artificial Sequence
<220> FEATURE:
```

<223> OTHER INFORMATION: Primer

<400> SEQUENCE: 16
gmccagacaa tatagtttga cc                                        22

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
cacctgactg ctttatttca                                           20

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
aactcagacg ggatttgtta gg                                        22

<210> SEQ ID NO 19
<211> LENGTH: 49
<212> TYPE: DNA
<213> ORGANISM: Artificial Sequence
<220> FEATURE:
<223> OTHER INFORMATION: Primer

<400> SEQUENCE: 19
tggcataaga ccacctgact gctgcaaatg atgataagtt atatcgggc            49

<210> SEQ ID NO 20
<211> LENGTH: 51
<212> TYPE: DNA
<213> ORGANISM: Artificial Sequence
<220> FEATURE:
<223> OTHER INFORMATION: Primer

<400> SEQUENCE: 20
agcagtcagg tggtcttatg ccaaaaggtt gatattcatt tgagtacctc g         51

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
tatttcatca ggaggtctag aatc                                      24

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
gaggacagag tgagtacttt ga                                        22

```
<210> SEQ ID NO 23
<211> LENGTH: 45
<212> TYPE: DNA
<213> ORGANISM: Artificial Sequence
<220> FEATURE:
<223> OTHER INFORMATION: Primer

<400> SEQUENCE: 23
gctcactgtt caccacatag aactggctct tcctctgatg gcgct            45

<210> SEQ ID NO 24
<211> LENGTH: 45
<212> TYPE: DNA
<213> ORGANISM: Artificial Sequence
<220> FEATURE:
<223> OTHER INFORMATION: Primer

<400> SEQUENCE: 24
gccagttcta tgtggtgaac agtgagcccc atgtctcccg atctc            45

<210> SEQ ID NO 25
<211> LENGTH: 17
<212> TYPE: DNA
<213> ORGANISM: Artificial Sequence
<220> FEATURE:
<223> OTHER INFORMATION: Primer

<400> SEQUENCE: 25
gagggcatgg catggag                                           17

<210> SEQ ID NO 26
<211> LENGTH: 17
<212> TYPE: DNA
<213> ORGANISM: Artificial Sequence
<220> FEATURE:
<223> OTHER INFORMATION: Primer

<400> SEQUENCE: 26
gtcctgccag ctgtacc                                           17

<210> SEQ ID NO 27
<211> LENGTH: 43
<212> TYPE: DNA
<213> ORGANISM: Artificial Sequence
<220> FEATURE:
<223> OTHER INFORMATION: Primer

<400> SEQUENCE: 27 ggcaccttttt cccacactat accgcacgtt tggcatggtt gtc             43

<210> SEQ ID NO 28
<211> LENGTH: 44
<212> TYPE: DNA
<213> ORGANISM: Artificial Sequence
<220> FEATURE:
<223> OTHER INFORMATION: Primer

<400> SEQUENCE: 28
ggtatagtgt gggaaaaggt gcctcgagca tgttacctac aggt             44

<210> SEQ ID NO 29
<211> LENGTH: 22
<212> TYPE: DNA
<213> ORGANISM: Artificial Sequence
<220> FEATURE:
<223> OTHER INFORMATION: Primer
```

-continued

<400> SEQUENCE: 29
agtgggttca agatacctag ag                                              22

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
tcattcgttg tcgactggct c                                               21

<210> SEQ ID NO 31
<211> LENGTH: 942
<212> TYPE: DNA
<213> ORGANISM: Homo Sapiens

<400> SEQUENCE: 31
atgcctgtgg ccggctcgga gctgccgcgc cggcccttgc cccccgccgc acaggagcgg     60
gacgccgagc cgcgtccgcc gcacggggag ctgcagtacc tggggcagat ccaacacatc    120
ctccgctgcg gcgtcaggaa ggacgaccgc acgggcaccg gcaccctgtc ggtattcggc    180
atgcaggcgc gctacagcct gagagatgaa ttccctctgc tgacaaccaa acgtgtgttc    240
tggaagggtg ttttggagga gttgctgtgg tttatcaagg gatccacaaa tgctaaagag    300
ctgtcttcca agggagtgaa aatctgggat gccaatggat cccgagactt tttggacagc    360
ctgggattct ccaccagaga agaagggac ttgggcccag tttatggctt ccagtggagg    420
cattttgggg cagaatacag agatatggaa tcagattatt caggacaggg agttgaccaa    480
ctgcaaagag tgattgacac catcaaaacc aaccctgacg acagaagaat catcatgtgc    540
gcttggaatc caagagatct tcctctgatg gcgctgcctc catgccatgc cctctgccag    600
ttctatgtgg tgaacagtga gctgtcctgc agctgtacc agagatcggg agacatgggc    660
ctcggtgtgc ctttcaacat cgccagctac gccctgctca cgtacatgat gcgcacatc    720 acgggcctga agccaggtga ctttatacac actttgggag atgcacatat ttacctgaat    780
cacatcgagc cactgaaaat tcagcttcag cgagaaccca gacctttccc aaagctcagg    840
attcttcgaa aagttgagaa aattgatgac ttcaaagctg aagactttca gattgaaggg    900
tacaatccgc atccaactat taaaatggaa atggctgttt tg                       942

<210> SEQ ID NO 32
<211> LENGTH: 3569
<212> TYPE: DNA
<213> ORGANISM: Enterobacterio phage MS2

<400> SEQUENCE: 32
gggtgggacc cctttcgggg tcctgctcaa cttcctgtcg agctaatgcc atttttaatg     60
tctttagcga gacgctacca tggctatcgc tgtaggtagc cggaattcca ttcctaggag    120
gtttgacctg tgcgagcttt tagtaccctt gataggagag acgagacctt cgtcccctcc    180
gttcgcgttt acgcggacgg tgagactgaa gataactcat tctctttaaa atatcgttcg    240
aactggactc ccggtcgttt taactcgact ggggccaaaa cgaaacagtg gcactacccc    300
tctccgtatt cacgggggc gttaagtgtc acatcgatag atcaaggtgc ctacaagcga    360
agtgggtcat cgtgggtcg cccgtacgag gagaaagccg gtttcggctt ctccctcgac    420
gcacgctcct gctacagcct cttccctgta agccaaaact tgacttacat cgaagtgccg    480

```
cagaacgttg cgaaccgggc gtcgaccgaa gtcctgcaaa aggtcaccca gggtgatttt    540
aaccttggtg ttgctttagc agaggccagg tcgacagcct cacaactcgc gacgcaaacc    600
attgcgctcg tgaaggcgta cactgccgct cgtcgcggta attggcgcca ggcgctccgc    660
taccttgccc taaacgaaga tcgaaagttt cgatcaaaac acgtggccgg caggtggttg    720
gagttgcagt tcggttggtt accactaatg agtgatatcc agggtgcata tgagatgctt    780
acgaaggttc accttcaaga gtttcttcct atgagagccg tacgtcaggt cggtactaac    840
atcaagttag atggccgtct gccgtatcca gctgcaaact ccagacaac gtgcaacata     900 tcgcgacgta tcgtgatatg gttttacata aacgatgcac gtttggcatg gttgtcgtct    960
ctaggtatct tgaacccact aggtatagtg tgggaaaagg tgcctttctc attcgttgtc   1020
gactggctcc tacctgtagg taacatgctc gagggcctta cggcccccgt gggatgctcc   1080
tacatgtcag gaacagttac tgacgtaata acgggtgagt ccatcataag cgttgacgct   1140
ccctacgggt ggactgtgga gagacagggc actgctaagg cccaaatctc agccatgcat   1200
cgaggggtac aatccgtatg ccaacaact ggcgcgtacg taaagtctcc tttctcgatg    1260
gtccatacct tagatgcgtt agcattaatc aggcaacggc tctctagata gagccctcaa   1320
ccggagtttg aagcatggct tctaaccttta ctcagttcgt tctcgtcgac aatggcggaa   1380
ctggcgacgt gactgtcgcc caagcaact tcgctaacgg ggtcgctgaa tggatcagct    1440
ctaactcgcg ttcacaggct tacaaagtaa cctgtagcgt tcgtcagagc tctgcgcaga   1500
atcgcaaata caccatcaaa gtcgaggtgc ctaaagtggc aacccagact gttggtggtg   1560
tagagcttcc tgtagccgca tggcgttcgt acttaaatct ggaactaacc attccaattt   1620 cgccacgaa ttccgactgc gagcttattg ttaaggcaat gcaaggtctc ctaaaagatg    1680
gaaacccgat tccctcagca atcgcagcaa actccggcat ctactaatag acgccggcca   1740
ttcaaacatg aggattaccc atgtcgaaga caacaaagaa gttcaactct ttatgtattg   1800
atcttcctcg cgatctctct ctcgaaattt accaatcaat tgcttctgtc gctactggaa   1860
gcggtgatcc gcacagtgac gactttacag caattgctta cttaagggac gaattgctca   1920
caaagcatcc gaccttaggt tctggtaatg acgaggcgac ccgtcgtacc ttagctatcg   1980
ctaagctacg ggaggcgaat gatcggtgcg gtcagataaa tagagaaggt ttcttacatg   2040
acaaatcctt gtcatgggat ccggatgttt tacaaaccag catccgtagc cttattggca   2100
acctcctctc tggctaccga tcgtcgttgt ttgggcaatg cacgttctcc aacggtgcct   2160
ctatggggca caagttgcag gatgcagcgc cttacaagaa gttcgctgaa caagcaaccg   2220 ttacccccg cgctctgaga gcggctctat tggtccgaga ccaatgtgcg ccgtggatca    2280
gacacgcggt ccgctataac gagtcatatg aatttaggct cgttgtaggg aacggagtgt   2340
ttacagttcc gaagaataat aaaatagatc gggctgcctg taaggagcct gatatgaata   2400
tgtacctcca gaaaggggtc ggtgcctta tcagacgccg gctcaaatcc gttggtatag    2460
acctgaatga tcaatcgatc aaccagcgtc tggctcagca gggcagcgta gatggttcgc   2520
ttgcgacgat agacttatcg tctgcatccg attccatctc cgatcgcctg gtgtggagtt   2580
ttctcccacc tgagctatat tcatatctcg atcgtatccg ctcacactac ggaatcgtag   2640
atggcgagac gatacgatgg gaactatttt ccacaatggg aaatgggttc acatttgagc   2700
tagagtccat gatattctgg gcaatagtca aagcgaccca aatccatttt ggtaacgccg   2760
gaaccatagg catctacggg gacgatatta tatgtcccag tgagattgca ccccgtgtgc   2820
```

```
-continued tagaggcact tgcctactac ggttttaaac cgaatcttcg taaaacgttc gtgtccgggc    2880
tctttcgcga gagctgcggc gcgcactttt accgtggtgt cgatgtcaaa ccgttttaca    2940
tcaagaaacc tgttgacaat ctcttcgccc tgatgctgat attaaatcgg ctacggggtt    3000
ggggagttgt cggaggtatg tcagatccac gcctctataa ggtgtgggta cggctctcct    3060
cccaggtgcc ttcgatgttc ttcggtggga cggacctcgc tgccgactac tacgtagtca    3120
gcccgcctac ggcagtctcg gtatacacca agactccgta cgggcggctg ctcgcggata    3180
cccgtacctc gggtttccgt cttgctcgta tcgctcgaga acgcaagttc ttcagcgaaa    3240
agcacgacag tggtcgctac atagcgtggt tccatactgg aggtgaaatc accgacagca    3300
tgaagtccgc cggcgtgcgc gttatacgca cttcggagtg gctaacgccg gttcccacat    3360
tccctcagga gtgtgggcca gcgagctctc ctcggtagct gaccgaggga cccccgtaaa    3420
cggggtgggt gtgctcgaaa gagcacgggt ccgcgaaagc ggtggctcca ccgaaaggtg    3480
ggcgggcttc ggcccaggga cctcccccta aagagaggac ccgggattct cccgatttgg    3540
taactagctg cttggctagt taccaccca                                      3569
```